United States Patent
Venkatraman et al.

(10) Patent No.: US 12,152,018 B2
(45) Date of Patent: Nov. 26, 2024

(54) COMPOUNDS AND COMPOSITIONS FOR TREATING CONDITIONS ASSOCIATED WITH STING ACTIVITY

(71) Applicant: IFM Due, Inc., Boston, MA (US)

(72) Inventors: Shankar Venkatraman, Lansdale, PA (US); Jason Katz, Newton, MA (US); William R. Roush, Boston, MA (US); Hans Martin Seidel, Concord, MA (US)

(73) Assignee: IFM Due, Inc., Boston, MA (US)

( * ) Notice: Subject to any disclaimer, the term of this patent is extended or adjusted under 35 U.S.C. 154(b) by 0 days.

(21) Appl. No.: 17/570,936

(22) Filed: Jan. 7, 2022

(65) Prior Publication Data
US 2022/0242852 A1    Aug. 4, 2022

Related U.S. Application Data

(60) Provisional application No. 63/135,336, filed on Jan. 8, 2021.

(51) Int. Cl.
*C07D 401/14* (2006.01)
*C07D 209/40* (2006.01)
*C07D 403/10* (2006.01)
*C07D 403/14* (2006.01)
*C07D 405/14* (2006.01)

(52) U.S. Cl.
CPC ......... *C07D 403/14* (2013.01); *C07D 209/40* (2013.01); *C07D 401/14* (2013.01); *C07D 403/10* (2013.01); *C07D 405/14* (2013.01)

(58) Field of Classification Search
CPC ... C07D 401/14; C07D 403/10; C07D 403/14
See application file for complete search history.

(56) References Cited

U.S. PATENT DOCUMENTS

| | | | |
|---|---|---|---|
| 7,927,613 | B2 | 4/2011 | Almarsson |
| 2004/0110956 | A1 | 6/2004 | Didier |
| 2004/0132794 | A1 | 7/2004 | Didier |
| 2012/0046290 | A1 | 2/2012 | Dumas |
| 2012/0202848 | A1 | 8/2012 | Greene |
| 2015/0056224 | A1 | 2/2015 | Dubensky |
| 2017/0146519 | A1 | 5/2017 | DeFilippis et al. |
| 2020/0172534 | A1 | 6/2020 | Roush |
| 2021/0236466 | A1 | 8/2021 | Roush |
| 2022/0024906 | A1 | 1/2022 | Venkatraman et al. |
| 2022/0024919 | A1 | 1/2022 | Venkatraman et al. |
| 2022/0227760 | A1 | 7/2022 | Venkatraman et al. |
| 2022/0242852 | A1 | 8/2022 | Venkatraman et al. |
| 2022/0388957 | A1 | 12/2022 | Seidel et al. |
| 2023/0002320 | A1 | 1/2023 | Seidel et al. |
| 2023/0002373 | A1 | 1/2023 | Seidel et al. |
| 2023/0021448 | A1 | 1/2023 | Seidal et al. |
| 2023/0047905 | A1 | 2/2023 | Venkatraman et al. |
| 2023/0092163 | A1 | 3/2023 | Katz et al. |
| 2023/0106899 | A1 | 4/2023 | Glick et al. |
| 2023/0115274 | A1 | 4/2023 | Roush et al. |
| 2023/0127839 | A1 | 4/2023 | Seidel et al. |
| 2023/0167057 | A1 | 6/2023 | Venkatraman et al. |
| 2023/0250060 | A1 | 8/2023 | Venkatraman et al. |
| 2023/0250088 | A1 | 8/2023 | Venkatraman et al. |
| 2023/0250106 | A1 | 8/2023 | Venkatraman et al. |
| 2023/0271941 | A1 | 8/2023 | Venkatraman et al. |
| 2023/0365553 | A1 | 11/2023 | Venkatraman et al. |
| 2024/0041843 | A1 | 2/2024 | Glick et al. |
| 2024/0051970 | A1 | 2/2024 | Venkatraman et al. |
| 2024/0060982 | A1 | 2/2024 | Glick et al. |

(Continued)

FOREIGN PATENT DOCUMENTS

| | | |
|---|---|---|
| CN | 109734677 | 5/2019 |
| EP | 1256578 | 11/2002 |

(Continued)

OTHER PUBLICATIONS

Bastin et al., "Salt selection and optimisation procedures for pharmaceutical new chemical entities," Organic Process Res. & Dev., 2000, 4:427-435.
Cheng et al., "Identification of Thiourea-Based Inhibitors of the B-Cell Lymphoma 6 BTB Domain via NMR-Based Fragment Screening and Computer-Aided Drug Design," Journal of Medicinal Chemistry, Jul. 2018, 61:17:7573-7588.
Denya et al., "Design, synthesis and evaluation of indole derivatives as multifunctional agents against Alzheimer's disease," Medchemcomm, Jan. 2018, 9:2:357-370.
Djung et al., "The synthesis and evaluation of indolylureas as PKCa inhibitors", Bioorganic & Medicinal Chemistry, 2011, 19(8):2742-2750.
Drizin et al., "Structure-activity studies of a novel series of 5,6-fused heteroaromatic ureas as TRPV1 antagonists," Bioorganic & Medicinal Chemistry Elsevier, NL., Jul. 2006, 14:4740-4749.

(Continued)

*Primary Examiner* — Brian E McDowell
(74) *Attorney, Agent, or Firm* — Fish & Richardson P.C.

(57) ABSTRACT

This disclosure features chemical entities (e.g., a compound or a pharmaceutically acceptable salt, and/or hydrate, and/or cocrystal, and/or drug combination of the compound) having formula (I) that inhibit (e.g., antagonize) Stimulator of Interferon Genes (STING). Said chemical entities are useful, e.g., for treating a condition, disease or disorder in which increased (e.g., excessive) STING activation (e.g., STING signaling) contributes to the pathology and/or symptoms and/or progression of the condition, disease or disorder (e.g., cancer) in a subject (e.g., a human). This disclosure also features compositions containing the same as well as methods of using and making the same.

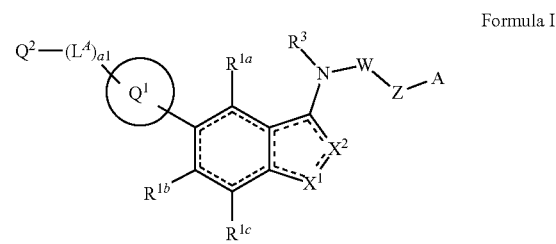

Formula I

36 Claims, No Drawings

(56) References Cited

U.S. PATENT DOCUMENTS

| | | |
|---|---|---|
| 2024/0076285 A1 | 3/2024 | Venkatraman |
| 2024/0083879 A1 | 3/2024 | Venkatraman et al. |
| 2024/0083895 A1 | 3/2024 | Roush et al. |
| 2024/0101556 A1 | 3/2024 | Venkatraman et al. |

FOREIGN PATENT DOCUMENTS

| | | |
|---|---|---|
| EP | 2226315 | 9/2010 |
| JP | 2015-098482 | 5/2015 |
| JP | 2020-524718 | 8/2020 |
| PT | 1599467 | 7/2010 |
| WO | WO 1995/014472 | 6/1995 |
| WO | WO 1999/000357 | 1/1999 |
| WO | WO 2000/047577 | 8/2000 |
| WO | WO 2001/012188 | 2/2001 |
| WO | WO 2002/050073 | 6/2002 |
| WO | WO 2003/028720 | 4/2003 |
| WO | WO 2003/028724 | 4/2003 |
| WO | WO 2003/055484 | 7/2003 |
| WO | WO 2003/068773 | 8/2003 |
| WO | WO 2003/097610 | 11/2003 |
| WO | WO 2004/022544 | 3/2004 |
| WO | WO 2005/073224 | 8/2005 |
| WO | WO 2007/024944 | 3/2007 |
| WO | WO 2007/090493 | 8/2007 |
| WO | WO 2008/116898 | 10/2008 |
| WO | WO 2008/154241 | 12/2008 |
| WO | WO 2008/156757 | 12/2008 |
| WO | WO 2009/102962 | 8/2009 |
| WO | WO 2009/112275 | 9/2009 |
| WO | WO 2009/140320 | 11/2009 |
| WO | WO 2000/026203 | 5/2011 |
| WO | WO 2011/133882 | 10/2011 |
| WO | WO 2011/133888 | 10/2011 |
| WO | WO 2012/077932 | 6/2012 |
| WO | WO 2012/129338 | 9/2012 |
| WO | WO 2012/158413 | 11/2012 |
| WO | WO 2012/178123 | 12/2012 |
| WO | WO 2013/114113 | 8/2013 |
| WO | WO 2014/078372 | 5/2014 |
| WO | WO 2015/061294 | 4/2015 |
| WO | WO 2015/112854 | 7/2015 |
| WO | WO 2016/049774 | 4/2016 |
| WO | WO 2017/020030 | 2/2017 |
| WO | WO 2017/034420 | 3/2017 |
| WO | WO 2017/035353 | 3/2017 |
| WO | WO 2017/175156 | 10/2017 |
| WO | WO 2017/189663 | 11/2017 |
| WO | WO 2018/132372 | 7/2018 |
| WO | WO 2018/234807 | 12/2018 |
| WO | WO 2018/234808 | 12/2018 |
| WO | WO 2019/012202 | 1/2019 |
| WO | WO 2019/122202 | 6/2019 |
| WO | WO 2019/034179 | 9/2019 |
| WO | WO 2019/185525 | 10/2019 |
| WO | WO 2019/201939 | 10/2019 |
| WO | WO 2020/010092 | 1/2020 |
| WO | WO 2020/010155 | 1/2020 |
| WO | WO 2020/150417 | 1/2020 |
| WO | WO 2020/106736 | 5/2020 |
| WO | WO 2020/106741 | 5/2020 |
| WO | WO 2020/150439 | 7/2020 |
| WO | WO 2020/191227 | 9/2020 |
| WO | WO 2020/236586 | 11/2020 |
| WO | WO 2020/243519 | 12/2020 |
| WO | WO 2020/252240 | 12/2020 |
| WO | WO 2020/257621 | 12/2020 |
| WO | WO 2021/067791 | 4/2021 |
| WO | WO 2021/067801 | 4/2021 |
| WO | WO 2021/067805 | 4/2021 |
| WO | WO 2021/138419 | 7/2021 |
| WO | WO 2021/138434 | 7/2021 |
| WO | WO 2022/015938 | 1/2022 |
| WO | WO 2022/015957 | 1/2022 |
| WO | WO 2022/015975 | 1/2022 |
| WO | WO 2022/015977 | 1/2022 |
| WO | WO 2022/015979 | 1/2022 |
| WO | WO 2022/133046 | 6/2022 |
| WO | WO 2022/133098 | 6/2022 |
| WO | WO 2022/140387 | 6/2022 |
| WO | WO 2022/140397 | 6/2022 |
| WO | WO 2022/140403 | 6/2022 |
| WO | WO 2022/140410 | 6/2022 |
| WO | WO 2022/150543 | 7/2022 |
| WO | WO 2022/150549 | 7/2022 |
| WO | WO 2022/150560 | 7/2022 |
| WO | WO 2022/150585 | 7/2022 |
| WO | WO 2023/018781 | 2/2023 |
| WO | WO 2023/137034 | 7/2023 |
| WO | WO 2023/137041 | 7/2023 |

OTHER PUBLICATIONS

Filipski et al., "Intestinal targeting of drugs: rational design approaches and challenges," Current Topics in Medicinal Chemistry, 2013, 13(7):776-802.
Haag et al., "Targeting STING with covalent small-molecule inhibitors", Nature, 2018, 559:269-273.
International Preliminary Report in Patentability in International Appln. No. PCTUS2020037403, dated Dec. 14, 2021, 11pages.
International Preliminary Report on Patentability in International Appln. No. PCT/US2020/054064, dated Apr. 5, 2022, 10 pages.
International Preliminary Report on Patentability in International Appln. No. PCT/US2020/067463, dated Jul. 5, 2022, 7 pages.
International Preliminary Report on Patentability in International Appln. No. PCT/US2020/067483, dated Jul. 5, 2022, 7 pages.
International Preliminary Report on Patentability in International Appln. No. PCT/US2019/040317, dated Jan. 5, 2021, 7 pages.
International Search Report and Written Opinion in International Appln. No. PCT/US2019/040317, dated Sep. 20, 2019, 16 pages.
International Search Report and Written Opinion in International Appln. No. PCT/US2020/067463, dated Feb. 25, 2021, 9 pages.
International Search Report and Written Opinion in International Appln. No. PCT/US2022/011542, dated Apr. 28, 2022, 12 pages.
International Search Report and Written Opinion in International Appln. No. PCT/US2020/037403, dated Sep. 3, 2020, 17 pages.
International Search Report and Written Opinion in International Appln. No. PCT/US2020/054064, dated Jan. 12, 2021, 18 pages.
International Search Report and Written Opinion in International Appln. No. PCT/US2020/067483, dated Apr. 9, 2021, 16 pages.
International Search Report and Written Opinion in International Appln. No. PCT/US2022/011571, dated Apr. 11, 2022, 15 pages.
International Search Report and Written Opinion in International Appln. No. PCT/US2022/011609, dated Mar. 22, 2022, 13 pages.
Kubinyi, "3D Qsar IN Drug Design: Ligand-protein interactions and molecular similarity," Springer, 1998, 2-3:243.
Kumaran et al., "Synthesis, Spectral Characterization and Antimicrobial Studies of New 3- and 4-substituted in 7-Aza Indole Derivatives", International Journal of PharmTech Research, 2012, 4(1):169-175.
Lammers et al., "Effect of intratumoral injection on the biodistribution and the therapeutic potential of HPMA copolymer-based drug delivery systems," Neoplasia, 2006, 10:788-795.
Minrovic et al., "Second-Generation Tryptamine Derivatives Potently Sensitize Colistin Resistant Bacteria to Colistin," ACS Medicinal Chemistry Letters, Apr. 2019, 10:5:828-833.
Mohamed et al., "Design, Synthesis and Cancer Cell Line Activities of Pyrazolo[3,4-Z^]pyridine Derivatives", Open Journal of Medicinal Chemistry, 2012, 2(3): 78-88.
Phuong-Thao et al., "Structure-activity relationship of human glutaminyl cyclase inhibitors having an N-(5-methyl-1 H-imidazol-1-yl)propyl thiourea template," Bioorganic & Medicinal chem., Jul. 1, 2013, 21(13):3821-3830.
Postow et al., "Immune Checkpoint Blockade in Cancer Therapy," J. Clin. Oncol., 2015, 33(17): 1974-1982.
Raffa et al., "Synthesis and antiproliferative activity of 3-amino-N-phenyl-1H-indazole-1-carbonxamides," European J. of Medicinal Chem., Jan. 2009, 165-178.

(56) References Cited

OTHER PUBLICATIONS

Serajuddin, "Salt formation to improve drug solubility," Advanced Drug Delivery Rev., 2007, 59:603-616.
Sheridan, "Drug developers switch gears to inhibit STING", Nat. Biotechnology, 2019, 37:3:199-201.
Sreenivasachary et al., "Discovery and characterization of novel indole and 7-azaindole derivatives as inhibitors of [beta]-amyloid-42 aggregation for the treatment of Alzheimer's disease," Bioorganic & Medicinal Chemistry Letters, Mar. 2017, 27:6:1405-1411.
Stahl et al., "Handbook of pharmaceuticals salts. Properties, selection and use," wiley-VCH, 2008, 265-327.
Swarbick et al., "Salt forms of drugs and absorption," Encyclopedia of Pharmaceutical Technology 13, 1996, 453-499.
Tran et al., "Structure-activity relationship of human glutaminyl cyclase inhibitors having an N-(5-methyl-1 H-imidazol-1-yl)propyl thiourea template," Bioorganic & medicinal Chemistry, Jul. 2013, 21:13:3821-3830.
Wermuth, "Electronic screening:Lead finding from database mining," The practice of Medicinal Chemistry, 2 ed, 2003,142.
Zhang et al., "Discovery of Azaindole Ureas as a Novel Class of Bacterial Gyrase B Inhibitors", Journal of Medicinal Chemistry, 2015, 58(21), 8503-8512.
Caballero et al., "Binding Studies and Quantitative Structure-Activity Relationship of 3-Amino-1H-Indazoles as Inhibitors of GSK3β," Chemical Biology & Drug Design, Jul. 2011, 78(4):631-641.
Gao et al., "Discovery of dual death-associated protein related apoptosis inducing protein kinase 1 and 2 inhibitors by a scaffold hopping approach.," Journal of Medicinal Chemistry, Sep. 11, 2014, 57(18):7624-7643.
Huang et al., "Identification of pyrazolopyridine derivatives as novel spleen tyrosine kinase inhibitors," Archiv Der Pharmazie, Jun. 27, 2018, 351(8):e1800083.
International Preliminary Report on Patentability in International Appln. No. PCT/US2021/041823, mailed on Jan. 26, 2023, 9 pages.
International Search Report and Written Opinion in International Appln. No. PCT/US2021/041823, mailed on Oct. 27, 2021, 15 pages.
Lesuisse et al., "Rational design of potent GSK3B inhibitors with selectivity for Cdk1 and Cdk2," Bioorganic & Medicinal Chemistry Letters, Mar. 15, 2010, 20(6):1985-1989.
Verdonck et al., "Synthesis and Structure-Activity Relationships of 3,5-Disubstituted-pyrrolo[2,3-b]pyridines as Inhibitors of Adaptor-Associated Kinase 1 with Antiviral Activity," Journal of Medicinal Chemistry, Jun. 27, 2019, 62(12):5810-5831.
Warren et al., "A Critical Assessment of Docking Programs and Scoring Functions," Journal of Medicinal Chemistry, Oct. 1, 2006, 49(20):5912-5931.
Bock et al., "Selective non-peptide ligands for an accommodating peptide receptor. lmidazobenzodiazepines as potent cholecystokinin type b receptor antagonists," Bioorganic & Medicinal Chemistry, Sep. 1994, 2(9):987-998.
CAS No. 1086057-08-0, "Methanesulfonamide, N-[5-[4-(4-pyridinyl)-6-quinolinyl]-1H-pyrazolo[3,4b]pyridin-3-yl]," dated Dec. 18, 2008, 3 pages.
CAS No. 1622882-49-8, "Benzenesulfonamide, N-[5-(2-amino-4 methylpyrido[2,3-d]pyrimidin-6-yl)pyrrolo[2,3-b]pyridin-3-yl]-2,4-difluoro," dated Sep. 12, 2014, 2 pages.
CAS No. 1791298-29-7, C10H13N3O2S, Sulfamide, N-1H-indol-6-yl-N,N-dimethyl-(ACI), CAS Sci Finder, available on or before Jun. 29, 2015, retrieved on Sep. 27, 2023, 6 pages.
Fournier et al., "Squaramides as novel class I and IIB histone deacetylase inhibitors for topical treatment of cutaneous t-cell lymphoma," Bioorganic & Medicinal Chemistry Letters, Elsevier, Jun. 2018, 28(17):2985-2992.
International Preliminary Report in Patentability Appl. No. PCT/US2022/011609, mailed on Jul. 20, 2023, 10 pages.
International Preliminary Report on Patentability in International Appln. No PCT/US2022/011571, mailed on Jul. 20, 2023, 11 pages.
International Preliminary Report on Patentability in International Appln. No. PCT/US2022/011551, mailed on Jul. 20, 2023, 9 pages.
International Preliminary Report on Patentability in International Appln. No. PCT/US2022/011542, mailed on Jul. 20, 2023, 10 pages.
International Search Report and Written Opinion in International Appln. No. PCT/US2022/011551, mailed on Mar. 18, 2022, 10 pages.
Ried, et al., "Synthese von Thieno[2,3-d]pyrimidinen und Pyrrolo[2,3d]pyrimidinen," Liebigs Ann. Chem., Jan. 1988, pp. 633-642 (with English abstract).

COMPOUNDS AND COMPOSITIONS FOR TREATING CONDITIONS ASSOCIATED WITH STING ACTIVITY

CROSS REFERENCE TO RELATED APPLICATION

This application claims the benefit of U.S. Provisional Application Ser. No. 63/135,336, filed on Jan. 8, 2021, which is incorporated herein by reference in its entirety.

TECHNICAL FIELD

This disclosure features chemical entities (e.g., a compound or a pharmaceutically acceptable salt, and/or hydrate, and/or cocrystal, and/or drug combination of the compound) that inhibit (e.g., antagonize) Stimulator of Interferon Genes (STING). Said chemical entities are useful, e.g., for treating a condition, disease or disorder in which increased (e.g., excessive) STING activation (e.g., STING signaling) contributes to the pathology and/or symptoms and/or progression of the condition, disease or disorder (e.g., cancer) in a subject (e.g., a human). This disclosure also features compositions containing the same as well as methods of using and making the same.

BACKGROUND

STING, also known as transmembrane protein 173 (TMEM173) and MPYS/MITA/ERIS, is a protein that in humans is encoded by the TMEM173 gene. STING has been shown to play a role in innate immunity. STING induces type I interferon production when cells are infected with intracellular pathogens, such as viruses, mycobacteria and intracellular parasites. Type I interferon, mediated by STING, protects infected cells and nearby cells from local infection in an autocrine and paracrine manner.

The STING pathway is pivotal in mediating the recognition of cytosolic DNA. In this context, STING, a transmembrane protein localized to the endoplasmic reticulum (ER), acts as a second messenger receptor for 2', 3' cyclic GMP-AMP (hereafter cGAMP), which is produced by cGAS after dsDNA binding. In addition, STING can also function as a primary pattern recognition receptor for bacterial cyclic dinucleotides (CDNs) and small molecule agonists. The recognition of endogenous or prokaryotic CDNs proceeds through the carboxy-terminal domain of STING, which faces into the cytosol and creates a V-shaped binding pocket formed by a STING homodimer. Ligand-induced activation of STING triggers its re-localization to the Golgi, a process essential to promote the interaction of STING with TBK1. This protein complex, in turn, signals through the transcription factors IRF-3 to induce type I interferons (IFNs) and other co-regulated antiviral factors. In addition, STING was shown to trigger NF-κB and MAP kinase activation. Following the initiation of signal transduction, STING is rapidly degraded, a step considered important in terminating the inflammatory response.

Excessive activation of STING is associated with a subset of monogenic autoinflammatory conditions, the so-called type I interferonopathies. Examples of these diseases include a clinical syndrome referred to as STING-associated vasculopathy with onset in infancy (SAVI), which is caused by gain-of-function mutations in TMEM173 (the gene name of STING). Moreover, STING is implicated in the pathogenesis of Aicardi-Goutières Syndrome (AGS) and genetic forms of lupus. As opposed to SAVI, it is the dysregulation of nucleic acid metabolism that underlies continuous innate immune activation in AGS. Apart from these genetic disorders, emerging evidence points to a more general pathogenic role for STING in a range of inflammation-associated disorders such as systemic lupus erythematosus, rheumatoid arthritis and cancer. Thus, small molecule-based pharmacological interventions into the STING signaling pathway hold significant potential for the treatment of a wide spectrum of diseases.

SUMMARY

This disclosure features chemical entities (e.g., a compound or a pharmaceutically acceptable salt, and/or hydrate, and/or cocrystal, and/or drug combination of the compound) that inhibit (e.g., antagonize) Stimulator of Interferon Genes (STING). Said chemical entities are useful, e.g., for treating a condition, disease or disorder in which increased (e.g., excessive) STING activation (e.g., STING signaling) contributes to the pathology and/or symptoms and/or progression of the condition, disease or disorder (e.g., cancer) in a subject (e.g., a human). This disclosure also features compositions containing the same as well as methods of using and making the same.

An "antagonist" of STING includes compounds that, at the protein level, directly bind or modify STING such that an activity of STING is decreased, e.g., by inhibition, blocking or dampening agonist-mediated responses, altered distribution, or otherwise. STING antagonists include chemical entities, which interfere or inhibit STING signaling.

In one aspect, compounds of Formula (I), or a pharmaceutically acceptable salt thereof, are featured:

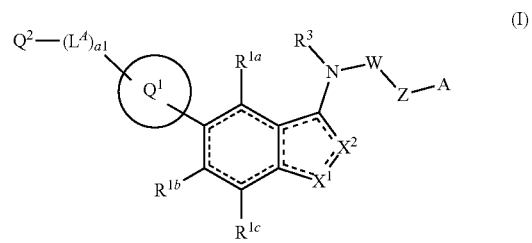

in which $Q^1$, $L^A$, a1, $Q^2$, $R^{1a}$, $R^{1b}$, $R^{1c}$, $R^3$, $X^1$, $X^2$, W, Z, and A can be as defined anywhere herein.

In one aspect, pharmaceutical compositions are featured that include a chemical entity described herein (e.g., a compound described generically or specifically herein or a pharmaceutically acceptable salt thereof or compositions containing the same) and one or more pharmaceutically acceptable excipients.

In one aspect, methods for inhibiting (e.g., antagonizing) STING activity are featured that include contacting STING with a chemical entity described herein (e.g., a compound described generically or specifically herein or a pharmaceutically acceptable salt thereof or compositions containing the same). Methods include in vitro methods, e.g., contacting a sample that includes one or more cells comprising STING (e.g., innate immune cells, e.g., mast cells, macrophages, dendritic cells (DCs), and natural killer cells) with the chemical entity. Methods can also include in vivo methods; e.g., administering the chemical entity to a subject (e.g., a human) having a disease in which increased (e.g., excessive)

STING signaling contributes to the pathology and/or symptoms and/or progression of the disease.

In one aspect, methods of treating a condition, disease or disorder ameliorated by antagonizing STING are featured, e.g., treating a condition, disease or disorder in which increased (e.g., excessive) STING activation (e.g., STING signaling) contributes to the pathology and/or symptoms and/or progression of the condition, disease or disorder (e.g., cancer) in a subject (e.g., a human). The methods include administering to a subject in need of such treatment an effective amount of a chemical entity described herein (e.g., a compound described generically or specifically herein or a pharmaceutically acceptable salt thereof or compositions containing the same).

In another aspect, methods of treating cancer are featured that include administering to a subject in need of such treatment an effective amount of a chemical entity described herein (e.g., a compound described generically or specifically herein or a pharmaceutically acceptable salt thereof or compositions containing the same).

In a further aspect, methods of treating other STING-associated conditions are featured, e.g., type I interferonopathies (e.g., STING-associated vasculopathy with onset in infancy (SAVI)), Aicardi-Goutières Syndrome (AGS), genetic forms of lupus, and inflammation-associated disorders such as systemic lupus erythematosus, and rheumatoid arthritis. The methods include administering to a subject in need of such treatment an effective amount of a chemical entity described herein (e.g., a compound described generically or specifically herein or a pharmaceutically acceptable salt thereof or compositions containing the same).

In another aspect, methods of suppressing STING-dependent type I interferon production in a subject in need thereof are featured that include administering to the subject an effective amount of a chemical entity described herein (e.g., a compound described generically or specifically herein or a pharmaceutically acceptable salt thereof or compositions containing the same).

In a further aspect, methods of treating a disease in which increased (e.g., excessive) STING activation (e.g., STING signaling) contributes to the pathology and/or symptoms and/or progression of the disease are featured. The methods include administering to a subject in need of such treatment an effective amount of a chemical entity described herein (e.g., a compound described generically or specifically herein or a pharmaceutically acceptable salt thereof or compositions containing the same).

In another aspect, methods of treatment are featured that include administering an effective amount of a chemical entity described herein (e.g., a compound described generically or specifically herein or a pharmaceutically acceptable salt thereof or compositions containing the same) to a subject; wherein the subject has (or is predisposed to have) a disease in which increased (e.g., excessive) STING activation (e.g., STING signaling) contributes to the pathology and/or symptoms and/or progression of the disease.

In a further aspect, methods of treatment that include administering to a subject a chemical entity described herein (e.g., a compound described generically or specifically herein or a pharmaceutically acceptable salt thereof or compositions containing the same), wherein the chemical entity is administered in an amount effective to treat a disease in which increased (e.g., excessive) STING activation (e.g., STING signaling) contributes to the pathology and/or symptoms and/or progression of the disease, thereby treating the disease.

In another aspect, is a compound, or a pharmaceutically acceptable salt or tautomer thereof, described herein, for use in the treatment of a disease, condition or disorder modulated by STING inhibition.

In another aspect, is a compound, or a pharmaceutically acceptable salt or tautomer thereof, described herein for use in the treatment of a condition, disease or disorder associated with increased (e.g., excessive) STING activation.

In another aspect, is a compound, or a pharmaceutically acceptable salt or tautomer thereof, described herein for use in the treatment of cancer.

In another aspect, is a compound, or a pharmaceutically acceptable salt or tautomer thereof, described herein for use in the treatment of cancer selected from the group consisting of melanoma, cervical cancer, breast cancer, ovarian cancer, prostate cancer, testicular cancer, urothelial carcinoma, bladder cancer, non-small cell lung cancer, small cell lung cancer, sarcoma, colorectal adenocarcinoma, gastrointestinal stromal tumors, gastroesophageal carcinoma, colorectal cancer, pancreatic cancer, kidney cancer, hepatocellular cancer, malignant mesothelioma, leukemia, lymphoma, myelodysplasia syndrome, multiple myeloma, transitional cell carcinoma, neuroblastoma, plasma cell neoplasms, Wilm's tumor, or hepatocellular carcinoma.

In another aspect, is a compound, or a pharmaceutically acceptable salt or tautomer thereof, described herein for use in the treatment of type I interferonopathies.

In another aspect, is a compound, or a pharmaceutically acceptable salt or tautomer thereof, described herein for use in the treatment of type I interferonopathies selected from STING-associated vasculopathy with onset in infancy (SAVI)), Aicardi-Goutières Syndrome (AGS), genetic forms of lupus, and inflammation-associated disorders such as systemic lupus erythematosus, and rheumatoid arthritis.

In another aspect, is the use of a compound, or a pharmaceutically acceptable salt or tautomer thereof, described herein for use in the manufacture of a medicament for the treatment of a condition, disease or disorder associated with increased (e.g., excessive) STING activation.

In another aspect, is the use of a compound, or a pharmaceutically acceptable salt or tautomer thereof, described herein for use in the manufacture of a medicament for the treatment of cancer.

In another aspect, is the use of a compound, or a pharmaceutically acceptable salt or tautomer thereof, described herein for use in the manufacture of a medicament for the treatment of cancer selected from the group consisting of melanoma, cervical cancer, breast cancer, ovarian cancer, prostate cancer, testicular cancer, urothelial carcinoma, bladder cancer, non-small cell lung cancer, small cell lung cancer, sarcoma, colorectal adenocarcinoma, gastrointestinal stromal tumors, gastroesophageal carcinoma, colorectal cancer, pancreatic cancer, kidney cancer, hepatocellular cancer, malignant mesothelioma, leukemia, lymphoma, myelodysplasia syndrome, multiple myeloma, transitional cell carcinoma, neuroblastoma, plasma cell neoplasms, Wilm's tumor, or hepatocellular carcinoma.

In another aspect, is the use of a compound, or a pharmaceutically acceptable salt or tautomer thereof, described herein for use in the manufacture of a medicament for the treatment of type I interferonopathies.

In another aspect, is the use of a compound, or a pharmaceutically acceptable salt or tautomer thereof, described herein for use in the manufacture of a medicament for the treatment of type I interferonopathies selected from STING-associated vasculopathy with onset in infancy (SAVI)), Aicardi-Goutières Syndrome (AGS), genetic forms of lupus, and inflammation-associated disorders such as systemic lupus erythematosus, and rheumatoid arthritis.

In another aspect, is the use of a compound, or a pharmaceutically acceptable salt or tautomer thereof, described herein, for the treatment of a disease, condition or disorder modulated by STING inhibition.

In another aspect, is the use of a compound, or a pharmaceutically acceptable salt or tautomer thereof, described herein for the treatment of a condition, disease or disorder associated with increased (e.g., excessive) STING activation.

In another aspect, is the use of a compound, or a pharmaceutically acceptable salt or tautomer thereof, described herein for the treatment of cancer.

In another aspect, is the use of a compound, or a pharmaceutically acceptable salt or tautomer thereof, described herein for the treatment of cancer selected from the group consisting of melanoma, cervical cancer, breast cancer, ovarian cancer, prostate cancer, testicular cancer, urothelial carcinoma, bladder cancer, non-small cell lung cancer, small cell lung cancer, sarcoma, colorectal adenocarcinoma, gastrointestinal stromal tumors, gastroesophageal carcinoma, colorectal cancer, pancreatic cancer, kidney cancer, hepatocellular cancer, malignant mesothelioma, leukemia, lymphoma, myelodysplasia syndrome, multiple myeloma, transitional cell carcinoma, neuroblastoma, plasma cell neoplasms, Wilm's tumor, or hepatocellular carcinoma.

In another aspect, is the use of a compound, or a pharmaceutically acceptable salt or tautomer thereof, described herein for the treatment of type I interferonopathies.

In another aspect, is the use of a compound, or a pharmaceutically acceptable salt or tautomer thereof, described herein for the treatment of type I interferonopathies selected from STING-associated vasculopathy with onset in infancy (SAVI)), Aicardi-Goutières Syndrome (AGS), genetic forms of lupus, and inflammation-associated disorders such as systemic lupus erythematosus, and rheumatoid arthritis.

Embodiments can include one or more of the following features.

The chemical entity can be administered in combination with one or more additional therapeutic agents and/or regimens. For examples, methods can further include administering one or more (e.g., two, three, four, five, six, or more) additional agents.

The chemical entity can be administered in combination with one or more additional therapeutic agents and/or regimens that are useful for treating other STING-associated conditions, e.g., type I interferonopathies (e.g., STING-associated vasculopathy with onset in infancy (SAVI)), Aicardi-Goutières Syndrome (AGS), genetic forms of lupus, and inflammation-associated disorders such as systemic lupus erythematosus, and rheumatoid arthritis.

The chemical entity can be administered in combination with one or more additional cancer therapies (e.g., surgery, radiotherapy, chemotherapy, toxin therapy, immunotherapy, cryotherapy or gene therapy, or a combination thereof, e.g., chemotherapy that includes administering one or more (e.g., two, three, four, five, six, or more) additional chemotherapeutic agents. Non-limiting examples of additional chemotherapeutic agents is selected from an alkylating agent (e.g., cisplatin, carboplatin, mechlorethamine, cyclophosphamide, chlorambucil, ifosfamide and/or oxaliplatin); an anti-metabolite (e.g., azathioprine and/or mercaptopurine); a terpenoid (e.g., a vinca alkaloid and/or a taxane; e.g., Vincristine, Vinblastine, Vinorelbine and/or Vindesine Taxol, Paclitaxel and/or Docetaxel); a topoisomerase (e.g., a type I topoisomerase and/or a type 2 topoisomerase; e.g., camptothecins, such as irinotecan and/or topotecan; amsacrine, etoposide, etoposide phosphate and/or teniposide); a cytotoxic antibiotic (e.g., actinomycin, anthracyclines, doxorubicin, daunorubicin, valrubicin, idarubicin, epirubicin, bleomycin, plicamycin and/or mitomycin); a hormone (e.g., a luteinizing hormone releasing hormone agonist; e.g., leuprolidine, goserelin, triptorelin, histrelin, bicalutamide, flutamide and/or nilutamide); an antibody (e.g., Abciximab, Adalimumab, Alemtuzumab, Atlizumab, Basiliximab, Belimumab, Bevacizumab, Brentuximab vedotin, Canakinumab, Cetuximab, Certolizumab pegol, Daclizumab, Denosumab, Eculizumab, Efalizumab, Gemtuzumab, Golimumab, Golimumab, Ibritumomab tiuxetan, Infliximab, Ipilimumab, Muromonab-CD3, Natalizumab, Ofatumumab, Omalizumab, Palivizumab, Panitumumab, Ranibizumab, Rituximab, Tocilizumab, Tositumomab and/or Trastuzumab); an anti-angiogenic agent; a cytokine; a thrombotic agent; a growth inhibitory agent; an anti-helminthic agent; and an immune checkpoint inhibitor that targets an immune checkpoint receptor selected from the group consisting of CTLA-4, PD-1, PD-L1, PD-1-PD-L1, PD-1-PD-L2, interleukin-2 (IL-2), indoleamine 2,3-dioxygenase (IDO), IL-10, transforming growth factor-$\beta$ (TGF$\beta$), T cell immunoglobulin and mucin 3 (TIM3 or HAVCR2), Galectin 9-TIM3, Phosphatidylserine-TIM3, lymphocyte activation gene 3 protein (LAG3), MHC class II-LAG3, 4-1BB-4-1BB ligand, OX40-OX40 ligand, GITR, GITR ligand-GITR, CD27, CD70-CD27, TNFRSF25, TNFRSF25-TL1A, CD40L, CD40-CD40 ligand, HVEM-LIGHT-LTA, HVEM, HVEM-BTLA, HVEM-CD160, HVEM-LIGHT, HVEM-BTLA-CD160, CD80, CD80-PDL-1, PDL2-CD80, CD244, CD48-CD244, CD244, ICOS, ICOS-ICOS ligand, B7-H3, B7-H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86-CD28, CD86-CTLA, CD80-CD28, CD39, CD73 Adenosine-CD39-CD73, CXCR4-CXCL12, Phosphatidylserine, TIM3, Phosphatidylserine-TIM3, SIRPA-CD47, VEGF, Neuropilin, CD160, CD30, and CD155 (e.g., CTLA-4 or PD1 or PD-L1).

The subject can have cancer; e.g., the subject has undergone and/or is undergoing and/or will undergo one or more cancer therapies.

Non-limiting examples of cancer include melanoma, cervical cancer, breast cancer, ovarian cancer, prostate cancer, testicular cancer, urothelial carcinoma, bladder cancer, non-small cell lung cancer, small cell lung cancer, sarcoma, colorectal adenocarcinoma, gastrointestinal stromal tumors, gastroesophageal carcinoma, colorectal cancer, pancreatic cancer, kidney cancer, hepatocellular cancer, malignant mesothelioma, leukemia, lymphoma, myelodysplasia syndrome, multiple myeloma, transitional cell carcinoma, neuroblastoma, plasma cell neoplasms, Wilm's tumor, or hepatocellular carcinoma. In certain embodiments, the cancer can be a refractory cancer.

The chemical entity can be administered intratumorally.

The methods can further include identifying the subject.

Other embodiments include those described in the Detailed Description and/or in the claims.

Additional Definitions

To facilitate understanding of the disclosure set forth herein, a number of additional terms are defined below. Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs. Each of the patents, applications, published applications, and other publications that are mentioned throughout the specification and the attached appendices are incorporated herein by reference in their entireties.

As used herein, the term "STING" is meant to include, without limitation, nucleic acids, polynucleotides, oligonucleotides, sense and antisense polynucleotide strands, complementary sequences, peptides, polypeptides, proteins, homologous and/or orthologous STING molecules, isoforms, precursors, mutants, variants, derivatives, splice variants, alleles, different species, and active fragments thereof.

The term "acceptable" with respect to a formulation, composition or ingredient, as used herein, means having no persistent detrimental effect on the general health of the subject being treated.

"API" refers to an active pharmaceutical ingredient.

The terms "effective amount" or "therapeutically effective amount," as used herein, refer to a sufficient amount of a chemical entity being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

The term "excipient" or "pharmaceutically acceptable excipient" means a pharmaceutically-acceptable material, composition, or vehicle, such as a liquid or solid filler, diluent, carrier, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington: The Science and Practice of Pharmacy, 21st ed.*; Lippincott Williams & Wilkins: Philadelphia, PA, 2005; *Handbook of Pharmaceutical Excipients, 6th ed.*; Rowe et al., Eds.; The Pharmaceutical Press and the American Pharmaceutical Association: 2009; *Handbook of Pharmaceutical Additives, 3rd ed.*; Ash and Ash Eds.; Gower Publishing Company: 2007; *Pharmaceutical Preformulation and Formulation, 2nd ed.*; Gibson Ed.; CRC Press LLC: Boca Raton, FL, 2009.

The term "pharmaceutically acceptable salt" refers to a formulation of a compound that does not cause significant irritation to an organism to which it is administered and does not abrogate the biological activity and properties of the compound. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. In some instances, pharmaceutically acceptable salts are obtained by reacting a compound having acidic group described herein with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods previously determined. The pharmacologically acceptable salt s not specifically limited as far as it can be used in medicaments. Examples of a salt that the compounds described herein form with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid:organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

The term "pharmaceutical composition" refers to a mixture of a compound described herein with other chemical components (referred to collectively herein as "excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to: rectal, oral, intravenous, aerosol, parenteral, ophthalmic, pulmonary, and topical administration.

The term "subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

The terms "treat," "treating," and "treatment," in the context of treating a disease or disorder, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof. The "treatment of cancer", refers to one or more of the following effects: (1) inhibition, to some extent, of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion and/or (8) relief, to some extent, of the severity or number of one or more symptoms associated with the disorder.

The term "halo" refers to fluoro (F), chloro (Cl), bromo (Br), or iodo (I).

The term "alkyl" refers to a saturated acyclic hydrocarbon radical that may be a straight chain or branched chain, containing the indicated number of carbon atoms. For example, $C_{1-10}$ indicates that the group may have from 1 to 10 (inclusive) carbon atoms in it. Alkyl groups can either be unsubstituted or substituted with one or more substituents.

Non-limiting examples include methyl, ethyl, iso-propyl, tert-butyl, n-hexyl. The term "saturated" as used in this context means only single bonds present between constituent carbon atoms and other available valences occupied by hydrogen and/or other substituents as defined herein.

The term "haloalkyl" refers to an alkyl, in which one or more hydrogen atoms is/are replaced with an independently selected halo.

The term "alkoxy" refers to an —O-alkyl radical (e.g., —OCH$_3$).

The term "alkylene" refers to a divalent alkyl (e.g., —CH$_2$—).

The term "alkenyl" refers to an acyclic hydrocarbon chain that may be a straight chain or branched chain having one or more carbon-carbon double bonds. The alkenyl moiety contains the indicated number of carbon atoms. For example, C$_{2-6}$ indicates that the group may have from 2 to 6 (inclusive) carbon atoms in it. Alkenyl groups can either be unsubstituted or substituted with one or more substituents.

The term "alkynyl" refers to an acyclic hydrocarbon chain that may be a straight chain or branched chain having one or more carbon-carbon triple bonds. The alkynyl moiety contains the indicated number of carbon atoms. For example, C$_{2-6}$ indicates that the group may have from 2 to 6 (inclusive) carbon atoms in it. Alkynyl groups can either be unsubstituted or substituted with one or more substituents.

The term "aryl" refers to a 6-20 carbon mono-, bi-, tri- or polycyclic group wherein at least one ring in the system is aromatic (e.g., 6-carbon monocyclic, 10-carbon bicyclic, or 14-carbon tricyclic aromatic ring system); and wherein 0, 1, 2, 3, or 4 atoms of each ring may be substituted by a substituent. Examples of aryl groups include phenyl, naphthyl, tetrahydronaphthyl, dihydro-1H-indenyl, and the like.

The term "cycloalkyl" as used herein refers to cyclic saturated hydrocarbon groups having, e.g., 3 to 20 ring carbons, preferably 3 to 16 ring carbons, and more preferably 3 to 12 ring carbons or 3-10 ring carbons or 3-6 ring carbons, wherein the cycloalkyl group may be optionally substituted. Examples of cycloalkyl groups include, without limitation, cyclopropyl, cyclobutyl, cyclopentyl, cyclohexyl, cycloheptyl, and cyclooctyl. Cycloalkyl may include multiple fused and/or bridged rings. Non-limiting examples of fused/bridged cycloalkyl includes: bicyclo[1.1.0]butanyl, bicyclo[2.1.0]pentanyl, bicyclo[1.1.1]pentanyl, bicyclo[3.1.0]hexanyl, bicyclo[2.1.1]hexanyl, bicyclo[3.2.0]heptanyl, bicyclo[4.1.0]heptanyl, bicyclo[2.2.1]heptanyl, bicyclo[3.1.1]heptanyl, bicyclo[4.2.0]octanyl, bicyclo[3.2.1]octanyl, bicyclo[2.2.2]octanyl, and the like. Cycloalkyl also includes spirocyclic rings (e.g., spirocyclic bicycle wherein two rings are connected through just one atom). Non-limiting examples of spirocyclic cycloalkyls include spiro[2.2]pentanyl, spiro[2.5]octanyl, spiro[3.5]nonanyl, spiro[3.5]nonanyl, spiro[3.5]nonanyl, spiro[4.4]nonanyl, spiro[2.6]nonanyl, spiro[4.5]decanyl, spiro[3.6]decanyl, spiro[5.5]undecanyl, and the like. The term "saturated" as used in this context means only single bonds present between constituent carbon atoms.

The term "cycloalkenyl" as used herein means partially unsaturated cyclic hydrocarbon groups having 3 to 20 ring carbons, preferably 3 to 16 ring carbons, and more preferably 3 to 12 ring carbons or 3-10 ring carbons or 3-6 ring carbons, wherein the cycloalkenyl group may be optionally substituted. Examples of cycloalkenyl groups include, without limitation, cyclopentenyl, cyclohexenyl, cycloheptenyl, and cyclooctenyl. As partially unsaturated cyclic hydrocarbon groups, cycloalkenyl groups may have any degree of unsaturation provided that one or more double bonds is present in the ring, none of the rings in the ring system are aromatic, and the cycloalkenyl group is not fully saturated overall. Cycloalkenyl may include multiple fused and/or bridged and/or spirocyclic rings.

The term "heteroaryl", as used herein, means a mono-, bi-, tri- or polycyclic group having 5 to 20 ring atoms, alternatively 5, 6, 9, 10, or 14 ring atoms; and having 6, 10, or 14 pi electrons shared in a cyclic array; wherein at least one ring in the system is aromatic, and at least one ring in the system contains one or more heteroatoms independently selected from the group consisting of N, O, and S (but does not have to be a ring which contains a heteroatom, e.g. tetrahydroisoquinolinyl, e.g., tetrahydroquinolinyl). Heteroaryl groups can either be unsubstituted or substituted with one or more substituents. Examples of heteroaryl include thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridinyl, pyrazolo[4,3-b]pyridinyl, tetrazolyl, chromanyl, 2,3-dihydrobenzo[b][1,4]dioxinyl, benzo[d][1,3]dioxolyl, benzo[d]thiazolyl, 2,3-dihydrobenzofuranyl, tetrahydroquinolinyl, 2,3-dihydrobenzo[b][1,4]oxathiinyl, isoindolinyl, and others. In some embodiments, the heteroaryl is selected from thienyl, pyridinyl, furyl, pyrazolyl, imidazolyl, isoindolinyl, pyranyl, pyrazinyl, and pyrimidinyl.

The term "heterocyclyl" refers to a mon-, bi-, tri-, or polycyclic saturated ring system with 3-16 ring atoms (e.g., 5-8 membered monocyclic, 8-12 membered bicyclic, or 11-14 membered tricyclic ring system) having 1-3 heteroatoms if monocyclic, 1-6 heteroatoms if bicyclic, or 1-9 heteroatoms if tricyclic or polycyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like. Heterocyclyl may include multiple fused and bridged rings. Non-limiting examples of fused/bridged heterocyclyl includes: 2-azabicyclo[1.1.0]butanyl, 2-azabicyclo[2.1.0]pentanyl, 2-azabicyclo[1.1.1]pentanyl, 3-azabicyclo[3.1.0]hexanyl, 5-azabicyclo[2.1.1]hexanyl, 3-azabicyclo[3.2.0]heptanyl, octahydrocyclopenta[c]pyrrolyl, 3-azabicyclo[4.1.0]heptanyl, 7-azabicyclo[2.2.1]heptanyl, 6-azabicyclo[3.1.1]heptanyl, 7-azabicyclo[4.2.0]octanyl, 2-azabicyclo[2.2.2]octanyl, 3-azabicyclo[3.2.1]octanyl, 2-oxabicyclo[1.1.0]butanyl, 2-oxabicyclo[2.1.0]pentanyl, 2-oxabicyclo[1.1.1]pentanyl, 3-oxabicyclo[3.1.0]hexanyl, 5-oxabicyclo[2.1.1]hexanyl, 3-oxabicyclo[3.2.0]heptanyl, 3-oxabicyclo[4.1.0]heptanyl, 7-oxabicyclo[2.2.1]heptanyl, 6-oxabicyclo[3.1.1]heptanyl, 7-oxabicyclo[4.2.0]octanyl, 2-oxabicyclo[2.2.2]octanyl, 3-oxabicyclo[3.2.1]octanyl, and the like. Heterocyclyl also includes spirocyclic rings (e.g., spirocyclic bicycle wherein two rings are connected through just one atom). Non-limiting examples of spirocyclic heterocyclyls include 2-azaspiro[2.2]pentanyl, 4-azaspiro[2.5]octanyl, 1-azaspiro[3.5]nonanyl, 2-azaspiro[3.5]nonanyl, 7-azaspiro[3.5]nonanyl, 2-azaspiro[4.4]nonanyl, 6-azaspiro[2.6]nonanyl, 1,7-diazaspiro[4.5]decanyl, 7-azaspiro[4.5]decanyl, 2,5-diazaspiro[3.6]decanyl, 3-azaspiro[5.5]undecanyl, 2-oxaspiro[2.2]pentanyl, 4-oxaspiro[2.5]octanyl, 1-oxaspiro[3.5]nonanyl, 2-oxaspiro[3.5]nonanyl, 7-oxaspiro[3.5]nonanyl, 2-oxaspiro[4.4]nonanyl, 6-oxaspiro[2.6]nonanyl, 1,7-dioxaspiro[4.5]decanyl, 2,5-dioxaspiro[3.6]decanyl, 1-oxaspiro[5.5]undecanyl, 3-oxaspiro[5.5]undecanyl, 3-oxa-9-azaspiro[5.5]undecanyl and the like. The term "saturated" as used in this context means only single bonds present between constituent ring atoms and other available valences occupied by hydrogen and/or other substituents as defined herein.

The term "heterocycloalkenyl" as used herein means partially unsaturated cyclic ring system with 3-16 ring atoms (e.g., 5-8 membered monocyclic, 8-12 membered bicyclic, or 11-14 membered tricyclic ring system) having 1-3 heteroatoms if monocyclic, 1-6 heteroatoms if bicyclic, or 1-9 heteroatoms if tricyclic or polycyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocycloalkenyl groups include, without limitation, tetrahydropyridyl, dihydropyrazinyl, dihydropyridyl, dihydropyrrolyl, dihydrofuranyl, dihydrothiophenyl. As partially unsaturated cyclic groups, heterocycloalkenyl groups may have any degree of unsaturation provided that one or more double bonds is present in the ring, none of the rings in the ring system are aromatic, and the heterocycloalkenyl group is not fully saturated overall. Heterocycloalkenyl may include multiple fused and/or bridged and/or spirocyclic rings.

As used herein, when a ring is described as being "aromatic", it means said ring has a continuous, delocalized π-electron system. Typically, the number of out of plane π-electrons corresponds to the Hückel rule (4n+2). Examples of such rings include: benzene, pyridine, pyrimidine, pyrazine, pyridazine, pyridone, pyrrole, pyrazole, oxazole, thioazole, isoxazole, isothiazole, and the like.

As used herein, when a ring is described as being "partially unsaturated", it means said ring has one or more additional degrees of unsaturation (in addition to the degree of unsaturation attributed to the ring itself, e.g., one or more double or triple bonds between constituent ring atoms), provided that the ring is not aromatic. Examples of such rings include: cyclopentene, cyclohexene, cycloheptene, dihydropyridine, tetrahydropyridine, dihydropyrrole, dihydrofuran, dihydrothiophene, and the like.

For the avoidance of doubt, and unless otherwise specified, for rings and cyclic groups (e.g., aryl, heteroaryl, heterocyclyl, heterocycloalkenyl, cycloalkenyl, cycloalkyl, and the like described herein) containing a sufficient number of ring atoms to form bicyclic or higher order ring systems (e.g., tricyclic, polycyclic ring systems), it is understood that such rings and cyclic groups encompass those having fused rings, including those in which the points of fusion are located (i) on adjacent ring atoms (e.g., [x.x.0] ring systems, in which 0 represents a zero atom bridge (e.g., 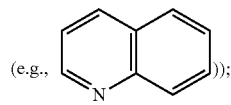));

(ii) a single ring atom (spiro-fused ring systems)

(e.g., 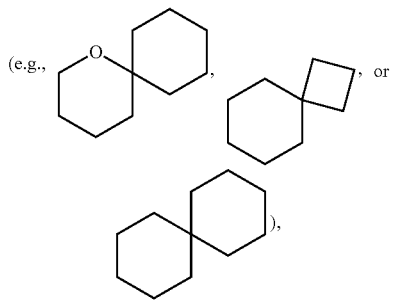), or (iii) a contiguous array of ring atoms (bridged ring systems having all bridge lengths >0)

(e.g., 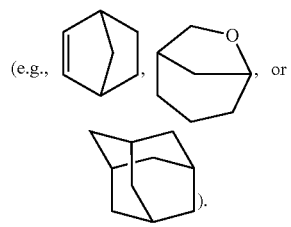).

In addition, atoms making up the compounds of the present embodiments are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C.

In addition, the compounds generically or specifically disclosed herein are intended to include all tautomeric forms. Thus, by way of example, a compound containing the moiety:

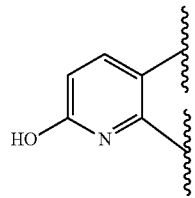 [SMILES: *c1ccc(O)nc1*]

encompasses the tautomeric form containing the moiety:

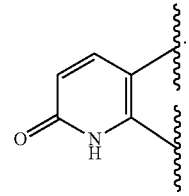 [SMILES: *c1ccc(=O)[nH]c1*]

Similarly, a pyridinyl or pyrimidinyl moiety that is described to be optionally substituted with hydroxyl encompasses pyridone or pyrimidone tautomeric forms.

The details of one or more embodiments of the invention are set forth in the accompanying drawings and the description below. Other features and advantages of the invention will be apparent from the description and drawings, and from the claims.

DETAILED DESCRIPTION

This disclosure features chemical entities (e.g., a compound or a pharmaceutically acceptable salt, and/or hydrate, and/or cocrystal, and/or drug combination of the compound) that inhibit (e.g., antagonize) Stimulator of Interferon Genes (STING). Said chemical entities are useful, e.g., for treating a condition, disease or disorder in which increased (e.g., excessive) STING activation (e.g., STING signaling) contributes to the pathology and/or symptoms and/or progression of the condition, disease or disorder (e.g., cancer) in a subject (e.g., a human). This disclosure also features compositions containing the same as well as methods of using and making the same.

Formula I Compounds

In one aspect, this disclosure features compounds of Formula (I):

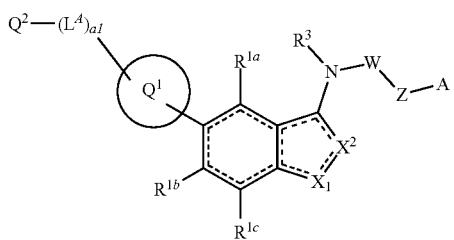

Formula I or a pharmaceutically acceptable salt thereof or a tautomer thereof, wherein:

$X^1$ is selected from the group consisting of O, S, N, $NR^2$, and $CR^5$;

$X^2$ is selected from the group consisting of O, S, N, $NR^4$, and $CR^5$;

each ═ is independently a single bond or a double bond, provided that the five-membered ring comprising $X^1$ and $X^2$ is heteroaryl, and the 6-membered ring

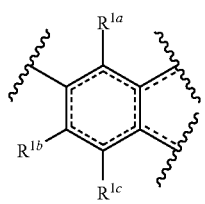

is aromatic;

$R^{1a}$, $R^{1b}$, $R^{1c}$, and $R^5$ are each independently selected from the group consisting of: H; $R^c$; $R^h$; and $-(L^1)_{n1}-R^h$;

each occurrence of $R^2$ and $R^4$ is independently selected from the group consisting of: H; $R^d$; $R^g$; and $-(L^2)_{b2}-R^g$;

$Q^1$ is selected from the group consisting of:

$C_{3-12}$ cycloalkylene or $C_{3-12}$ cycloalkenylene, each optionally substituted with 1-4 substituents independently selected from the group consisting of oxo, $R^c$, and $R^h$;

heterocyclylene or heterocycloalkenylene of 3-12 ring atoms, wherein 1-3 ring atoms are heteroatoms, each independently selected from the group consisting of N, N(H), $N(R^d)$, O, and $S(O)_{0-2}$, and wherein the heterocyclylene or heterocycloalkenylene is optionally substituted with 1-4 substituents independently selected from the group consisting of oxo, $R^c$, and $R^h$;

heteroarylene of 5-12 ring atoms, wherein 1-3 ring atoms are heteroatoms, each independently selected from the group consisting of N, N(H), $N(R^d)$, O, and $S(O)_{0-2}$, and wherein the heteroarylene is optionally substituted with 1-4 substituents independently selected from the group consisting of $R^c$ and $R^h$; and $C_{6-10}$ arylene optionally substituted with 1-4 substituents independently selected from the group consisting of $R^c$ and $R^h$;

each $L^A$ is independently selected from the group consisting of: $C_{1-3}$ alkylene optionally substituted with 1-2 $R^a$; —O—; —NH—; —$NR^d$; —$S(O)_{0-2}$; and C(O);

a1 is 0, 1, 2, 3, or 4;

provided that -$(L^A)_{a1}$- cannot contain bond(s) between O, N, or $S(O)_0$ atoms, unless an N—N bond is further attached to C(O);

$Q^2$ is $R^g$;

$R^3$ is selected from the group consisting of: H; $R^d$; and $R^h$;

W is selected from the group consisting of:

(i) C(═O); (ii) C(═S); (iii) $S(O)_{1-2}$; (iv) C(═$NR^d$) or C(═N—CN); (v) C(═NH); (vi) C(═CH—$NO_2$); (vii) S(═O)(═$N(R^d)$); and (viii) S(═O)(═NH);

Z and A are defined according to (AA) or (BB) below:

(AA)

Z is —N(H)— or —$N(R^d)$—;

A is selected from the group consisting of:

H;

$C_{1-10}$ alkyl which is optionally substituted with 1-6 $R^b$; and

—$(Y^{A1})_{nA}$—$Y^{A2}$, wherein:

nA is 0 or 1;

$Y^{A1}$ is $C_{1-6}$ alkylene optionally substituted with 1-3 $R^b$; and $Y^{A2}$ is selected from the group consisting of:

monocyclic $C_{3-8}$ cycloalkyl or $C_{3-8}$ cycloalkenyl, each of which is optionally substituted with 1-4 substituents independently selected from the group consisting of oxo and $R^c$; and monocyclic heterocyclyl or heterocycloalkenyl of 3-8 ring atoms, wherein 1-3 ring atoms are heteroatoms, each independently selected from the group consisting of N, N(H), $N(R^d)$, O, and $S(O)_{0-2}$, and wherein the heterocyclyl or heterocycloalkenyl is optionally substituted with 1-4 substituents independently selected from the group consisting of oxo and $R^c$; or Z and A, taken together, form:

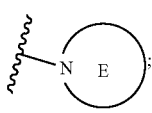

(BB)

and

Ring E is a saturated or partially unsaturated ring of 3-16 ring atoms, wherein 0-3 ring atoms are heteroatoms (in addition to the nitrogen atom already present), each independently selected from the group consisting of N, N(H), N($R^d$), O, and S(O)$_{0-2}$, and wherein the ring is optionally substituted with 1-4 substituents independently selected from the group consisting of: oxo, $R^c$, $R^h$, and -($L^g$)$_{bg}$-$R^h$;

each occurrence of $R^a$ and $R^b$ is independently selected from the group consisting of: —OH; -halo; —NR$^e$R$^f$; $C_{1-4}$ alkoxy; $C_{1-4}$ haloalkoxy; —C(=O)O($C_{1-4}$ alkyl); —C(=O)($C_{1-4}$ alkyl); —C(=O)OH; —CONR'R''; —S(O)$_{1-2}$NR'R''; —S(O)$_{1-2}$($C_{1-4}$ alkyl); and cyano;

each occurrence of $R^c$ is independently selected from the group consisting of: halo; cyano; $C_{1-10}$ alkyl which is optionally substituted with 1-6 independently selected $R^a$; $C_{2-6}$ alkenyl; $C_{2-6}$ alkynyl; $C_{1-4}$ alkoxy; $C_{1-4}$ haloalkoxy; —S(O)$_{1-2}$($C_{1-4}$ alkyl); —S(O)(=NH)($C_{1-4}$ alkyl); —NR$^e$R$^f$; —OH; —S(O)$_{1-2}$NR'R''; —$C_{1-4}$ thioalkoxy; —NO$_2$; —C(=O)($C_{1-10}$ alkyl); —C(=O)O($C_{1-4}$ alkyl); —C(=O)OH; —C(=O)NR'R''; and —SF$_5$;

each occurrence of $R^d$ is independently selected from the group consisting of: $C_{1-6}$ alkyl optionally substituted with 1-3 independently selected $R^a$; —C(O)($C_{1-4}$ alkyl); —C(O)O($C_{1-4}$ alkyl); —CONR'R''; —S(O)$_{1-2}$NR'R''; —S(O)$_{1-2}$($C_{1-4}$ alkyl); —OH; and $C_{1-4}$ alkoxy;

each occurrence of $R^e$ and $R^f$ is independently selected from the group consisting of: H; $C_{1-6}$ alkyl optionally substituted with 1-3 substituents each independently selected from the group consisting of NR'R'', —OH, and $R^i$; —C(O)($C_{1-4}$ alkyl); —C(O)O($C_{1-4}$ alkyl); —CONR'R''; —S(O)$_{1-2}$NR'R''; —S(O)$_{1-2}$($C_{1-4}$ alkyl); —OH; and $C_{1-4}$ alkoxy;

each occurrence of $R^g$ is independently selected from the group consisting of:
  $C_{3-12}$ cycloalkyl or $C_{3-12}$ cycloalkenyl, each of which is optionally substituted with 1-4 substituents independently selected from the group consisting of oxo, $R^c$, $R^h$, and -($L^g$)$_{bg}$-$R^h$;
  heterocyclyl or heterocycloalkenyl of 3-12 ring atoms, wherein 1-3 ring atoms are heteroatoms, each independently selected from the group consisting of N, N(H), N($R^d$), O, and S(O)$_{0-2}$, and wherein the heterocyclyl or heterocycloalkenyl is optionally substituted with 1-4 substituents independently selected from the group consisting of: oxo, $R^c$, $R^h$, and -($L^g$)$_{bg}$-$R^h$;
  heteroaryl of 5-12 ring atoms, wherein 1-3 ring atoms are heteroatoms, each independently selected from the group consisting of N, N(H), N($R^d$), O, and S(O)$_{0-2}$, and wherein the heteroaryl is optionally substituted with 1-4 substituents independently selected from the group consisting of $R^c$, $R^h$, and -($L^g$)$_{bg}$-$R^h$; and
  $C_{6-10}$ aryl optionally substituted with 1-4 substituents independently selected from the group consisting of $R^c$, $R^h$, and -($L^g$)$_{bg}$-$R^h$;

each occurrence of $R^h$ is independently selected from the group consisting of:
  $C_{3-8}$ cycloalkyl or $C_{3-8}$ cycloalkenyl, each of which is optionally substituted with 1-4 $R^i$;
  heterocyclyl or heterocycloalkenyl of 3-8 ring atoms, wherein 1-3 ring atoms are heteroatoms, each independently selected from the group consisting of N, N(H), N($R^d$), O, and S(O)$_{0-2}$, and wherein the heterocyclyl or heterocycloalkenyl is optionally substituted with 1-4 $R^i$;
  heteroaryl of 5-6 ring atoms, wherein 1-3 ring atoms are heteroatoms, each independently selected from the group consisting of N, N(H), N($R^d$), O, and S, and wherein the heteroaryl is optionally substituted with 1-4 $R^i$; and
  $C_6$ aryl optionally substituted with 1-4 $R^i$;

each occurrence of $R^i$ is independently selected from the group consisting of: $C_{1-6}$ alkyl; $C_{1-4}$ haloalkyl; $C_{1-4}$ alkoxy; $C_{1-4}$ haloalkoxy; and halo;

each occurrence of $L^1$, $L^2$, and $L^g$ is selected from the group consisting of: —O—, —NH—, —NR$^d$—, —S(O)$_{0-2}$, C(O), and $C_{1-3}$ alkylene optionally substituted with 1-3 $R^a$;

b1, b2, and bg are each independently 1, 2, or 3; and each occurrence of R' and R'' is independently selected from the group consisting of: H; —OH; and $C_{1-4}$ alkyl.

For avoidance of doubt, when -($L^A$)$_{a1}$- is described as not containing "bond(s) between O, N, or S(O)$_0$ atoms, unless an N—N bond is further attached to C(O)", -($L^A$)$_{a1}$-cannot comprise divalent moieties such as —N(H)—O—, —N($R^d$)—O, —O—O—, —S(O)$_0$—O—, —S(O)$_0$—N(H)—, S(O)$_0$—N($R^d$), or —S(O)$_0$—S(O)$_0$—; and -($L^A$)$_{a1}$-cannot comprise divalent moieties such as —N(H)—N(H)— or —N(H)—N($C_{1-3}$ alkyl)-, unless they are further attached to C(O).

Variable $Q^1$

In some embodiments, $Q^1$ is heteroarylene of 5-12 ring atoms, wherein 1-3 ring atoms are heteroatoms, each independently selected from the group consisting of N, N(H), N($R^d$), O, and S(O)$_{0-2}$, and wherein the heteroarylene is optionally substituted with 1-4 substituents independently selected from the group consisting of $R^c$ and $R^h$.

In certain of these embodiments, $Q^1$ is heteroarylene of 5-6 ring atoms, wherein 1-3 ring atoms are heteroatoms, each independently selected from the group consisting of N, N(H), N($R^d$), O, and S, and wherein the heteroarylene is optionally substituted with 1-3 substituents independently selected from the group consisting of $R^c$ and $R^h$.

In certain of the foregoing embodiments, $Q^1$ is heteroarylene of 5-6 ring atoms, wherein 1-3 ring atoms are heteroatoms, each independently selected from the group consisting of N, N(H), N($R^d$), O, and S, and wherein the heteroarylene is optionally substituted with 1-3 $R^c$.

In certain embodiments, $Q^1$ is heteroarylene of 5 ring atoms, wherein 1-3 ring atoms are heteroatoms, each independently selected from the group consisting of N, N(H), N($R^d$), O, and S, and wherein the heteroarylene is optionally substituted with 1-2 $R^c$.

In certain of these embodiments, $Q^1$ is pyrazolylene which is optionally substituted with 1-2 $R^c$.

As a non-limiting example of the foregoing embodiments, $Q^1$ is

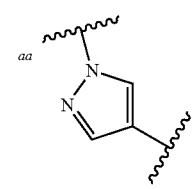 [SMILES: *c1cnn(*)c1]

which is optionally substituted with 1-2 $R^c$, wherein aa represents point of attachment to -($L^A$)$_{a1}$-$Q^2$. For example, $Q^1$ can be.

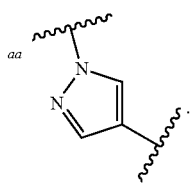 [SMILES: *c1cnn(*)c1]

As another non-limiting example, $Q^1$ can be

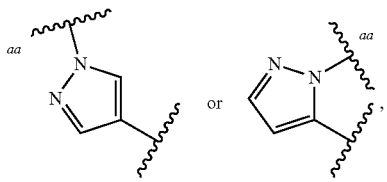 [SMILES: *c1cnn(*)c1 ; *c1ccnn1*]

each of which is optionally substituted with 1-2 $R^c$, wherein aa represents point of attachment to $-(L^A)_{a1}$-$Q^2$.

In certain embodiments, $Q^1$ is heteroarylene of 6 ring atoms, wherein 1-3 ring atoms are ring nitrogen atoms, and wherein the heteroarylene is optionally substituted with 1-3 substituents independently selected from the group consisting of $R^c$ and $R^h$.

In certain of these embodiments, $Q^1$ is pyridylene optionally substituted with 1-3 $R^c$.

As non-limiting examples of the foregoing embodiments, $Q^1$ can be

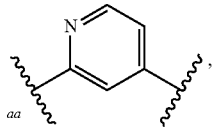 [SMILES: *c1ccnc(*)c1]

which is optionally substituted with 1-2 $R^c$, wherein aa represents point of attachment to $-(L^A)_{a1}$-$Q^2$.

In some embodiments, $Q^1$ is $C_{6-10}$ arylene optionally substituted with 1-4 substituents independently selected from the group consisting of $R^c$ and $R^h$.

In certain of these embodiments, $Q^1$ is phenylene which is optionally substituted with 1-3 substituents independently selected from the group consisting of $R^c$ and $R^h$.

As a non-limiting example of the foregoing embodiments, $Q^1$ can be

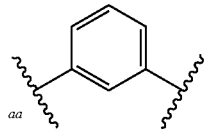

wherein aa represents point of attachment to $-(L^A)_{a1}$-$Q^2$.

Variables a1 and $L^A$

In some embodiments, a1 is 0. In certain embodiments, a1 is 1.

In some embodiments, $L^A$ is $CH_2$.

In certain embodiments, $-(L^A)_{a1}$- is $CH_2$.

Variable $Q^2$

In some embodiments, $Q^2$ is selected from the group consisting of:

heteroaryl of 5-12 ring atoms, wherein 1-3 ring atoms are heteroatoms, each independently selected from the group consisting of N, N(H), N($R^d$), O, and $S(O)_{0-2}$, and wherein the heteroaryl is optionally substituted with 1-4 substituents independently selected from the group consisting of $R^c$, $R^h$, and $-(L^g)_{bg}$-$R^h$; and $C_{6-10}$ aryl optionally substituted with 1-4 substituents independently selected from the group consisting of $R^c$, $R^h$, and $-(L)_{bg}$-$R^h$.

In certain of these embodiments, $Q^2$ is selected from the group consisting of:

heteroaryl of 5-6 ring atoms, wherein 1-3 ring atoms are heteroatoms, each independently selected from the group consisting of N, N(H), N($R^d$), O, and S, and wherein the heteroaryl is optionally substituted with 1-4 $R^{cq2}$; and $C_{6-10}$ aryl optionally substituted with 1-4 $R^{cq2}$, wherein each $R^{cq2}$ is an independently selected $R^c$.

In certain of the foregoing embodiments, $Q^2$ is selected from the group consisting of:

phenyl optionally substituted with 1-4 $R^{cq2}$; and heteroaryl of 6 ring atoms, wherein 1-3 ring atoms are ring nitrogen atoms, and wherein the heteroaryl is optionally substituted with 1-4 $R^{cq2}$, wherein each $R^{cq2}$ is an independently selected $R^c$.

For example, $Q^2$ can be phenyl or pyridyl, each optionally substituted with 1-2 $R^{cq2}$ wherein each $R^{cq2}$ is an independently selected $R^c$.

In certain embodiments, $Q^2$ has the following formula:

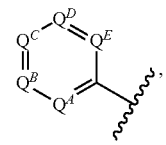

wherein $Q^A$, $Q^B$, $Q^C$, $Q^D$, and $Q^E$ are each independently selected from the group consisting of CH, $CR^{cq2}$, and N, provided that no more than 2 of $Q^A$-$Q^E$ are N, and no more than 2 of $Q^A$-$Q^E$ are $CR^{cq2}$, wherein each $R^{cq2}$ is an independently selected $R^c$.

In certain of these embodiments, $Q^A$, $Q^B$, $Q^C$, $Q^D$, and $Q^E$ are independently CH or $CR^{cq2}$, provided that no more than 2 of $Q^A$-$Q^E$ are $CR^{cq2}$.

In certain embodiments (when $Q^2$ has the following formula:

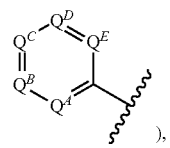

), $Q^A$ and $Q^E$ are CH; and $Q^B$, $Q^C$, and $Q^D$ are independently CH or $CR^{cq2}$, provided that no more than 2 of $Q^A$-$Q^E$ are $CR^{cq2}$.

In certain of these embodiments, $Q^B$ and $Q^D$ are CH; and $Q^C$ is $CR^{cq2}$.

In certain embodiments, $Q^B$ and $Q^C$ are CH; and $Q^D$ is $CR^{cq2}$.

In certain embodiments, $Q^B$, $Q^C$, and $Q^D$ are each CH.

In certain embodiments (when $Q^2$ has the following formula:

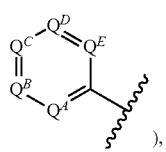

$Q^A$ is $CR^{cq2}$; and $Q^B$, $Q^C$, $Q^D$, and $Q^E$ are each CH.

As non-limiting examples, $Q^2$ can be selected from the group consisting of: unsubstituted phenyl,

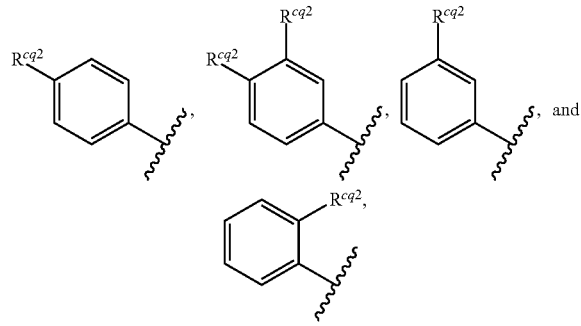

wherein each $R^{cq2}$ is an independently selected $R^c$.

In certain embodiments (when $Q^2$ has the following formula:

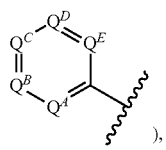

1-2 (e.g., 1) of $Q^A$-$Q^E$ is N; and each remaining one of $Q^A$-$Q^E$ is CH or $CR^{cq2}$ provided that no more than 2 of $Q^A$-$Q^E$ are $CR^{cq2}$.

In certain of these embodiments, $Q^A$ is N; each of $Q^B$, $Q^C$, $Q^D$, and $Q^E$ is independently CH or $CR^{cq2}$, provided that no more than 2 of $Q^B$-$Q^E$ are $CR^{cq2}$.

For example, $Q^2$ can be

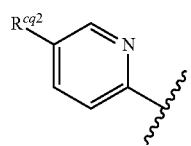

In some embodiments, $Q^2$ is $C_{3-12}$ cycloalkyl or $C_{3-12}$ cycloalkenyl, each of which is optionally substituted with 1-4 substituents independently selected from the group consisting of oxo and $R^{cq2}$, wherein each $R^{cq2}$ is an independently selected $R^c$.

In certain embodiments, $Q^2$ is:
(i) $C_{3-6}$ (e.g. $C_3$, $C_4$, $C_5$, or $C_6$) cycloalkyl, which is optionally substituted with 1-4 substituents independently selected from the group consisting of oxo and $R^{cq2}$; or
(ii) cyclopropyl or cyclopentyl each of which is optionally substituted with 1-2 $R^{cq2}$; or (iii)

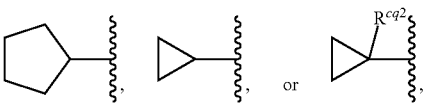

wherein each $R^{cq2}$ in (i), (ii), or (iii) is an independently selected $R^c$.

In certain embodiments, $Q^2$ is:
(i) heterocyclyl or heterocycloalkenyl of 3-12 ring atoms, wherein 1-3 ring atoms are heteroatoms, each independently selected from the group consisting of N, N(H), N($R^d$), O, and S(O)$_{0-2}$, and wherein the heterocyclyl or heterocycloalkenyl is optionally substituted with 1-4 substituents independently selected from the group consisting of oxo and $R^{cq2}$;
(ii) heterocyclyl of 4-8 ring atoms, wherein 1-3 ring atoms are heteroatoms, each independently selected from the group consisting of N, N(H), N($R^d$), O, and S(O)$_{0-2}$, and wherein the heterocyclyl is optionally substituted with 1-4 substituents independently selected from the group consisting of oxo and $R^{cq2}$; or
(iii)

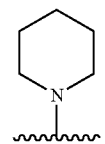 [SMILES: *N1CCCCC1]

optionally substituted with 1-2 $R^{cq2}$,
wherein each $R^{cq2}$ in (i), (ii), or (iii) is an independently selected $R^c$.

In certain embodiments, each $R^{cq2}$ is independently selected from the group consisting of: halo; cyano; $C_{1-6}$ alkyl which is optionally substituted with 1-6 independently selected $R^a$; $C_{1-4}$ alkoxy; $C_{1-4}$ haloalkoxy; and —$C_{1-4}$ thioalkoxy.

In certain embodiments, each $R^{cq2}$ is independently selected from the group consisting of: halo; cyano; $C_{1-6}$ alkyl (e.g., $C_{1-3}$ alkyl, e.g., ethyl); $C_{1-6}$ alkyl substituted with 1-6 independently selected $R^a$; $C_{1-4}$ alkoxy; $C_{1-4}$ haloalkoxy (e.g., —OCF$_3$ or —OCH$_2$CF$_3$); and —$C_{1-4}$ thioalkoxy.

In certain embodiments, each $R^{cq2}$ is independently selected from the group consisting of: halo; cyano; $C_{1-3}$ alkyl; $C_{1-3}$ alkyl substituted with 1-6 substituents each independently selected from the group consisting of -halo, $C_{1-3}$ alkoxy, and —OH (e.g., —CF$_3$, —CH$_2$CF$_3$, or —CH$_2$OMe); $C_{1-4}$ alkoxy; and $C_{1-4}$ haloalkoxy (e.g., —OCF$_3$ or —OCH$_2$CF$_3$).

Variables $R^{1a}$, $R^{1b}$, and $R^{1c}$
In some embodiments, $R^{1a}$ is —H.
In some embodiments, $R^{1b}$ is —H.
In some embodiments, $R^{1c}$ is —H.
In certain embodiments, $R^{1a}$ is —H; $R^{1b}$ is —H; and $R^{1c}$ is —H.

Variables $X^1$ and $X^2$
In some embodiments, $X^1$ is $NR^2$. In certain of these embodiments, $X^1$ is NH.
In some embodiments, $X^2$ is $CR^5$. In certain of these embodiments, $X^2$ is CH.
In certain embodiments, $X^1$ is NR; and $X^2$ is $CR^5$. In certain of these embodiments, $X^1$ is NH; and $X^2$ is CH.

Variable $R^3$

In some embodiments, $R^3$ is —H.

Variable W

In some embodiments, W is C(=O).

Variables Z and A

In some embodiments, Z and A are defined according to (AA).

In certain of these embodiments, Z is —N(H)—.

In certain embodiments, Z is —N($R^d$)—. As non-limiting examples of the foregoing embodiments, Z can be —N($C_{1-3}$ alkyl)- (e.g., —N(Me)-).

In certain embodiments, A is H.

In certain embodiments, A is $C_{1-10}$ alkyl which is optionally substituted with 1-6 $R^b$.

In certain of these embodiments, A is $C_{1-6}$ (e.g., C1, C2, C3, or $C_4$) alkyl, which is optionally substituted with 1-6 $R^b$.

In certain of the foregoing embodiments, A is $C_{1-6}$ alkyl. As non-limiting examples of the foregoing embodiments, A can be methyl, ethyl, propyl, isopropyl, or isobutyl. For example, A can be methyl.

In certain embodiments, A is $C_{1-6}$ alkyl which is substituted with 1-6 substituents each independently selected from the group consisting of: —OH; -halo; —N$R^e R^f$, optionally —N($C_{1-3}$ alkyl)$_2$ or NHC(O)O($C_{1-4}$ alkyl); $C_{1-4}$ alkoxy, optionally —OMe; $C_{1-4}$ haloalkoxy; —C(=O)O($C_{1-4}$ alkyl); —C(=O)($C_{1-4}$ alkyl); and cyano.

In certain of the foregoing embodiments, A is $C_{1-6}$ alkyl substituted with 1-6 independently selected halo (e.g., —F). As non-limiting examples of the foregoing embodiments, A can be —CH$_2$CF$_3$, —CH$_2$CH$_2$CF$_3$, or —CH$_2$CHF$_2$.

In certain embodiments, A is $C_{1-6}$ alkyl substituted with —OH, $C_{1-4}$ alkoxy, or $C_{1-4}$ haloalkoxy. As non-limiting examples of the foregoing embodiments, A can be

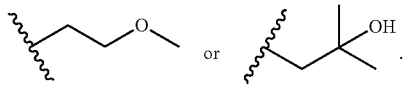

In certain embodiments, A is —($Y^{A1}$)$_{nA}$—$Y^{A2}$. In certain of these embodiments, nA is 0. In other embodiments, nA is 1.

In certain embodiments, $Y^{A1}$ is $C_{1-3}$ alkylene optionally substituted with 1-3 $R^b$. For example, $Y^{A1}$ can be —CH$_2$—.

In certain embodiments, $Y^{A2}$ is monocyclic $C_{3-8}$ cycloalkyl or $C_{3-8}$ cycloalkenyl, each of which is optionally substituted with 1-4 substituents independently selected from the group consisting of oxo and $R^c$.

In certain of these embodiments, $Y^{A2}$ is monocyclic $C_{3-8}$ cycloalkyl which is optionally substituted with 1-2 substituents independently selected from the group consisting of oxo and $R^c$.

In certain of the foregoing embodiments, $Y^{A2}$ is monocyclic $C_{3-6}$ cycloalkyl which is optionally substituted with 1-2 $R^c$.

As non-limiting examples of the foregoing embodiments, $Y^{A2}$ can be selected from the group consisting of cyclopropyl; cyclobutyl; and cyclopentyl, each of which is optionally substituted with 1-2 $R^c$.

In certain embodiments, $Y^{A2}$ is monocyclic heterocyclyl or heterocycloalkenyl of 3-8 ring atoms, wherein 1-3 ring atoms are heteroatoms, each independently selected from the group consisting of N, N(H), N($R^d$), O, and S(O)$_{0-2}$, and wherein the heterocyclyl or heterocycloalkenyl is optionally substituted with 1-4 substituents independently selected from the group consisting of oxo and $R^c$.

In certain of these embodiments, $Y^{A2}$ is monocyclic heterocyclyl of 4-6 ring atoms, wherein 1-2 ring atoms are heteroatoms, each independently selected from the group consisting of N, N(H), N($R^d$), O, and S(O)$_{0-2}$, and wherein the heterocyclyl is optionally substituted with 1-2 substituents independently selected from the group consisting of oxo and $R^c$.

As non-limiting examples of the foregoing embodiments, $Y^{A2}$ can be oxetanyl, tetrahydrofuranyl, or pyrrolidinyl, each of which is optionally substituted with 1-2 $R^c$, and the pyrrolidinyl is optionally substituted with $R^d$ at a ring nitrogen atom.

In some embodiments, Z and A are defined according to (BB).

In certain of these embodiments, Z and A, taken together, form:

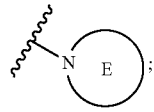

and

Ring E is a saturated or partially unsaturated ring of 3-8 ring atoms, wherein 0-2 ring atoms are heteroatoms (in addition to the ring nitrogen atom already present), each independently selected from the group consisting of N, N(H), N($R^d$), O, and S(O)$_{0-2}$, and wherein the ring is optionally substituted with 1-4 substituents independently selected from the group consisting of: oxo, $R^c$, $R^h$, and -($L^g$)$_{bg}$-$R^h$.

In certain of the foregoing embodiments, Z and A, taken together, form:

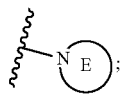

and

Ring E is a saturated ring of 3-8 ring atoms, wherein 0-2 ring atoms are heteroatoms (in addition to the ring nitrogen atom already present), each independently selected from the group consisting of N, N(H), N($R^d$), O, and S(O)$_{0-2}$, and wherein the ring is optionally substituted with 1-4 substituents independently selected from the group consisting of: oxo and $R^c$.

In certain embodiments, Z and A, taken together, form:

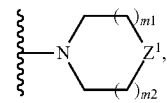

wherein m1 and m2 are independently 0, 1, or 2, wherein $Z^1$ is CH$_2$, CH($R^c$), C($R^c$)$_2$, NH, or N($R^d$).

In certain of these embodiments, m1 and m2 are independently 0 or 1.

In certain embodiments, $Z^1$ is CH$_2$ or N($R^d$); or $Z^1$ is CH$_2$ or NC(=O)($C_{1-3}$ alkyl).

Non-Limiting Combinations

In certain embodiments, the compound is a compound of Formula (Ia):

Formula Ia

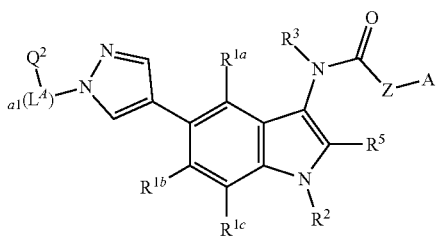

or a pharmaceutically acceptable salt thereof, wherein:
$L^A$ is —CH$_2$—; and
a1 is 0 or 1.
In certain embodiments of Formula (Ia), a1 is 0.
In certain embodiments of Formula (Ia), a1 is 1.
In certain embodiments of Formula (Ia), $Q^2$ has the following formula:

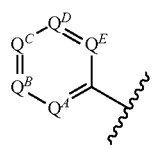

wherein $Q^A$, $Q^B$, $Q^C$, $Q^D$, and $Q^E$ are each independently selected from the group consisting of CH, CR$^{cq2}$, and N, provided that no more than 2 of $Q^A$-$Q^E$ are N, and no more than 2 of $Q^A$-$Q^E$ are CR$^{cq2}$, wherein each R$^{cq2}$ is an independently selected R$^c$.

In certain of these embodiments, $Q^A$, $Q^B$, $Q^C$, $Q^D$, and $Q^E$ are independently CH or CR$^{cq2}$, provided that no more than 2 of $Q^A$-$Q^E$ are CR$^{cq2}$.

In certain embodiments of Formula (Ia) (when $Q^2$ has the following formula:

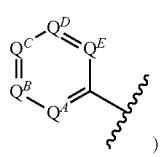

$Q^A$ and $Q^E$ are CH; and $Q^B$, $Q^C$, and $Q^D$ are independently CH or CR$^{cq2}$, provided that no more than 2 of $Q^A$-$Q^E$ are CR$^{cq2}$.

In certain of these embodiments, $Q^B$ and $Q^D$ are CH; and $Q^C$ is CR$^{cq2}$.

In certain embodiments, $Q^B$ and $Q^C$ are CH; and $Q^D$ is CR$^{cq2}$.

In certain embodiments, $Q^B$, $Q^C$, and $Q^D$ are each CH.

In certain embodiments of Formula (Ia) (when $Q^2$ has the following formula:

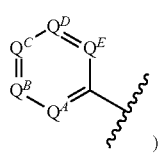

$Q^A$ is CR$^{cq2}$; and $Q^B$, $Q^C$, $Q^D$, and $Q^E$ are each CH.

In certain embodiments of Formula (Ia), $Q^2$ is selected from the group consisting of: unsubstituted phenyl,

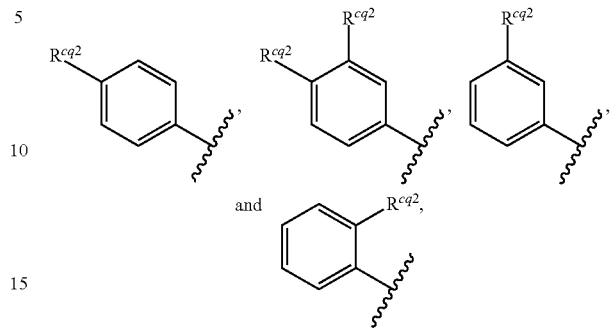

wherein each R$^{cq2}$ is an independently selected R$^c$.

In certain embodiments of Formula (Ia) (when $Q^2$ has the following formula:

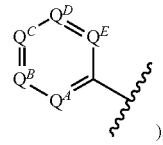

1-2 of $Q^A$-$Q^E$ is N; and each remaining one of $Q^A$-$Q^E$ is CH or CR$^{cq2}$, provided that no more than 2 of $Q^A$-$Q^E$ are CR$^{cq2}$.

In certain of these embodiments, $Q^A$ is N; each of $Q^B$, $Q^C$, $Q^D$, and $Q^E$ is independently CH or CR$^{cq2}$, provided that no more than 2 of $Q^B$-$Q^E$ are CR$^{cq2}$.

As a non-limiting example, $Q^2$ can be

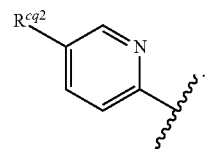

In certain embodiments of Formula (Ia), each R$^{cq2}$ is independently selected from the group consisting of: halo; cyano; C$_{1-6}$ alkyl; C$_{1-6}$ alkyl substituted with 1-6 substituents each independently selected from the group consisting of -halo, C$_{1-3}$ alkoxy, and —OH; C$_{1-4}$ alkoxy; C$_{1-4}$ haloalkoxy; and —C$_{1-4}$ thioalkoxy.

In certain embodiments of Formula (Ia), each R$^{cq2}$ is independently selected from the group consisting of: —F, —Cl, cyano, C$_{1-3}$ alkyl, —CF$_3$, —CH$_2$CF$_3$, —CH$_2$OMe, —OCF$_3$, and —OCH$_2$CF$_3$.

In certain embodiments of Formula (Ia), R$^{1a}$ is —H; R$^{1b}$ is —H; and R$^{1c}$ is —H.

In certain embodiments of Formula (Ia), R$^2$ is H.
In certain embodiments of Formula (Ia), R$^5$ is H.
In certain embodiments of Formula (Ia), R$^3$ is H.
In certain embodiments of Formula (Ia), Z and A are defined according to (AA).

In certain of these embodiments, Z is —N(H)—. In certain embodiments, Z is —N(C$_{1-3}$ alkyl)- (e.g., —N(CH$_3$)—).

In certain embodiments of Formula (Ia), A is H.

In certain embodiments of Formula (Ia), A is $C_{1-6}$ alkyl. As non-limiting examples of the foregoing embodiments, A can be methyl, ethyl, propyl, or isopropyl.

In certain embodiments of Formula (Ia), A is $C_{1-10}$ alkyl which is optionally substituted with 1-6 $R^b$.

In certain embodiments of Formula (Ia), A is $C_{1-6}$ alkyl which is substituted with 1-6 substituents each independently selected from the group consisting of: —OH; -halo; —NR$^e$R$^f$, optionally —N(C$_{1-3}$ alkyl)$_2$ or NHC(O)O(C$_{1-4}$ alkyl); C$_{1-4}$ alkoxy, optionally —OMe; C$_{1-4}$ haloalkoxy; —C(=O)O(C$_{1-4}$ alkyl); —C(=O)(C$_{1-4}$ alkyl); and cyano.

In certain embodiments of Formula (Ia), A is $C_{1-6}$ alkyl substituted with 1-6 independently selected halo. As non-limiting examples of the foregoing embodiments, A can be —CH$_2$CF$_3$, —CH$_2$CH$_2$CF$_3$, or —CH$_2$CHF$_2$.

In certain embodiments of Formula (Ia), A is $C_{1-6}$ alkyl substituted with —OH, C$_{1-4}$ alkoxy, or C$_{1-4}$ haloalkoxy. As non-limiting examples of the foregoing embodiments, A can be

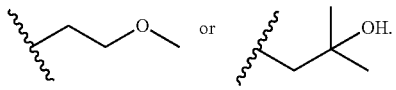

In certain embodiments of Formula (Ia), A is $Y^{A2}$ or —CH$_2$—$Y^{A2}$, wherein $Y^{A2}$ is selected from the group consisting of:
  monocyclic C$_{3-6}$ cycloalkyl, which is optionally substituted with 1-2 substituents independently selected from the group consisting of oxo and R$^c$; and
  monocyclic heterocyclyl of 4-6 ring atoms, wherein 1-2 ring atoms are heteroatoms, each independently selected from the group consisting of N, N(H), N(R$^d$), O, and S(O)$_{0-2}$, and wherein the heterocyclyl is optionally substituted with 1-2 substituents independently selected from the group consisting of oxo and R$^c$.

In certain embodiments of Formula (Ia), A is $Y^{A2}$ or —CH$_2$—$Y^{A2}$, wherein $Y^{A2}$ is selected from the group consisting of:
  cyclopropyl; cyclobutyl; or cyclopentyl, each of which is optionally substituted with 1-2 R$^c$; and
  oxetanyl, tetrahydrofuranyl, or pyrrolidinyl, each of which is optionally substituted with 1-2 R$^c$, and the pyrrolidinyl is optionally substituted with R$^d$ at a ring nitrogen atom.

In certain embodiments of Formula (Ia), Z and A are defined according to (BB).

In certain embodiments of Formula (Ia), Z and A, taken together, form:

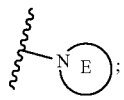

and

Ring E is a saturated ring of 3-8 ring atoms, wherein 0-2 ring atoms are heteroatoms (in addition to the ring nitrogen atom already present), each independently selected from the group consisting of N, N(H), N(R$^d$), O, and S(O)$_{0-2}$, and wherein the ring is optionally substituted with 1-4 substituents independently selected from the group consisting of: oxo and R$^c$.

In certain embodiments of Formula (Ia), Z and A, taken together, form:

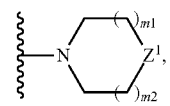

wherein m1 and m2 are independently 0, 1, or 2, wherein $Z^1$ is CH$_2$, CH(R$^c$), C(R$^c$)$_2$, NH, or N(R$^d$).

In certain of these embodiments, m1 and m2 are independently 0 or 1; and/or $Z^1$ is CH$_2$; or $Z^1$ is N(R$^d$), optionally NC(=O)(C$_{1-3}$ alkyl).

Non-Limiting Exemplary Compounds

In some embodiments, the compound is selected from the group consisting of the compounds delineated in Table C1 or a pharmaceutically acceptable salt thereof.

TABLE C1

| Compound No. | Structure |
|---|---|
| 101 | 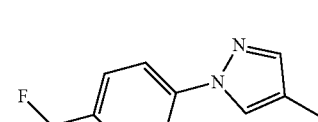 |
| 102 | 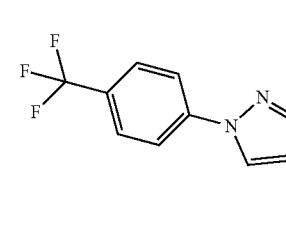 |

TABLE C1-continued

| Compound No. | Structure |
| --- | --- |
| 103 | 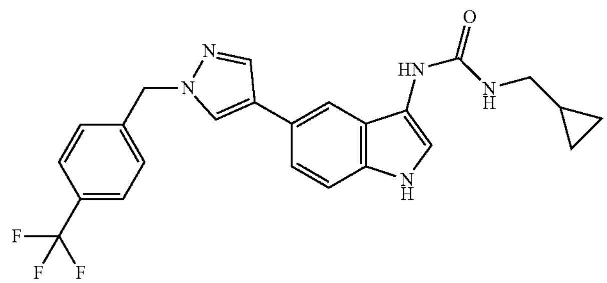 [SMILES: O=C(NCC1CC1)Nc1c[nH]c2ccc(-c3cnn(Cc4ccc(C(F)(F)F)cc4)c3)cc12] |
| 104 | 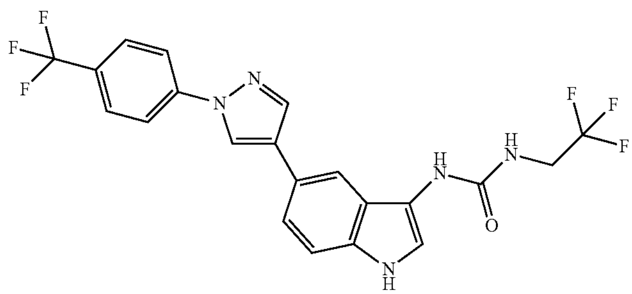 [SMILES: O=C(NCC(F)(F)F)Nc1c[nH]c2ccc(-c3cnn(-c4ccc(C(F)(F)F)cc4)c3)cc12] |
| 105 | 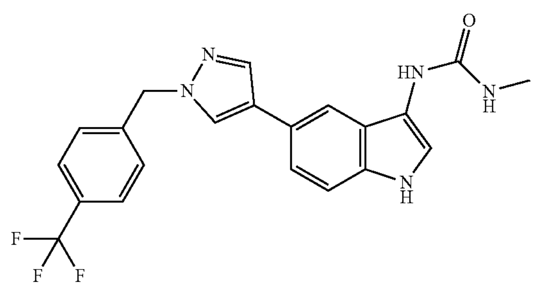 [SMILES: CNC(=O)Nc1c[nH]c2ccc(-c3cnn(Cc4ccc(C(F)(F)F)cc4)c3)cc12] |
| 106 | 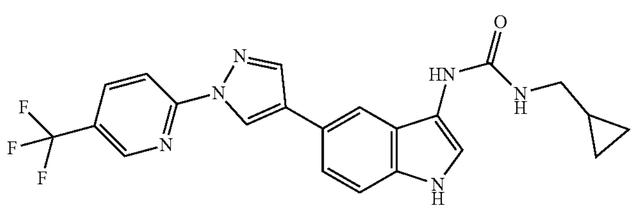 [SMILES: O=C(NCC1CC1)Nc1c[nH]c2ccc(-c3cnn(-c4ccc(C(F)(F)F)cn4)c3)cc12] |
| 107 | 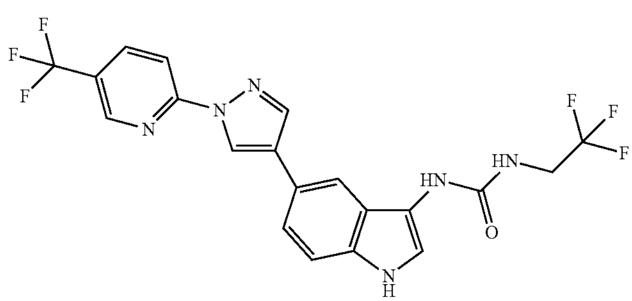 [SMILES: O=C(NCC(F)(F)F)Nc1c[nH]c2ccc(-c3cnn(-c4ccc(C(F)(F)F)cn4)c3)cc12] |

TABLE C1-continued

| Compound No. | Structure |
|---|---|
| 108 | 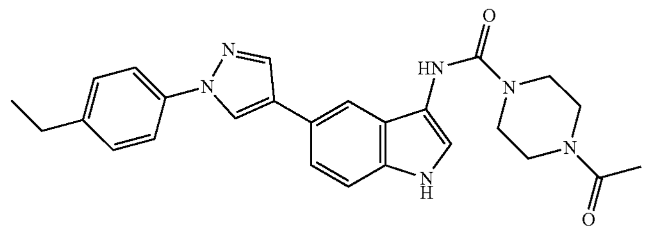 [SMILES: CCc1ccc(-n2cc(-c3ccc4[nH]cc(NC(=O)N5CCN(C(C)=O)CC5)c4c3)cn2)cc1] |
| 109 | 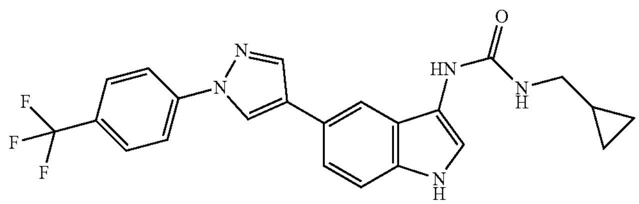 [SMILES: O=C(NCC1CC1)Nc1c[nH]c2ccc(-c3cnn(-c4ccc(C(F)(F)F)cc4)c3)cc12] |
| 110 | 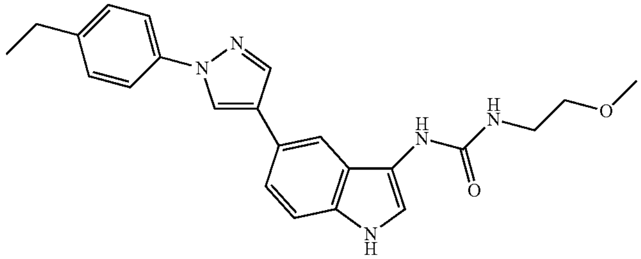 [SMILES: CCc1ccc(-n2cc(-c3ccc4[nH]cc(NC(=O)NCCOC)c4c3)cn2)cc1] |
| 111 | 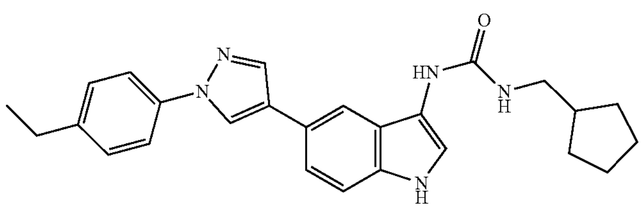 [SMILES: CCc1ccc(-n2cc(-c3ccc4[nH]cc(NC(=O)NCC5CCCC5)c4c3)cn2)cc1] |
| 112 | 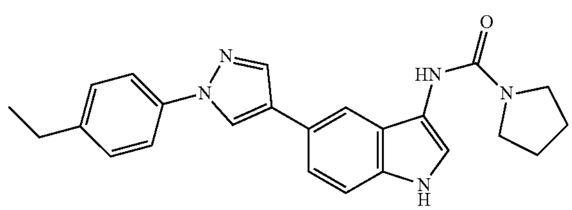 [SMILES: CCc1ccc(-n2cc(-c3ccc4[nH]cc(NC(=O)N5CCCC5)c4c3)cn2)cc1] |
| 113 | 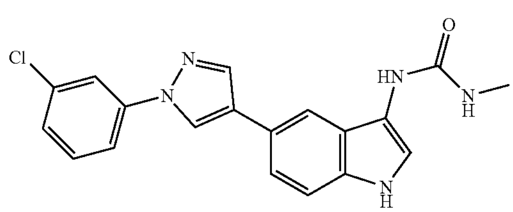 [SMILES: CNC(=O)Nc1c[nH]c2ccc(-c3cnn(-c4cccc(Cl)c4)c3)cc12] |
| 114 | 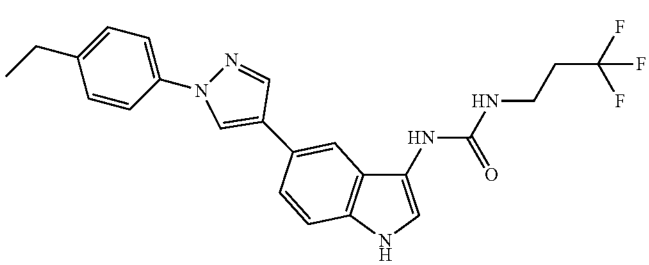 [SMILES: CCc1ccc(-n2cc(-c3ccc4[nH]cc(NC(=O)NCCC(F)(F)F)c4c3)cn2)cc1] |

TABLE C1-continued
| Compound No. | Structure |
|---|---|
| 115 | 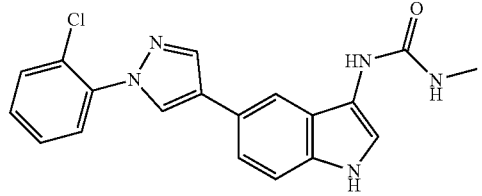 [SMILES: CNC(=O)Nc1c[nH]c2ccc(-c3cnn(-c4ccccc4Cl)c3)cc12] |
| 116 | 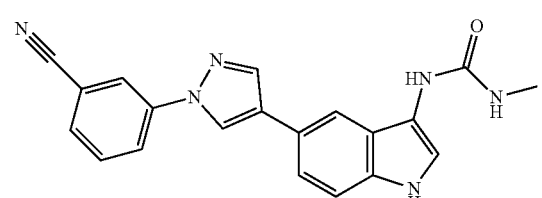 |
| 117 | 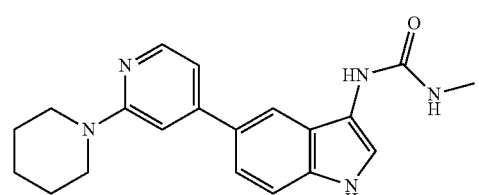 |
| 118 | 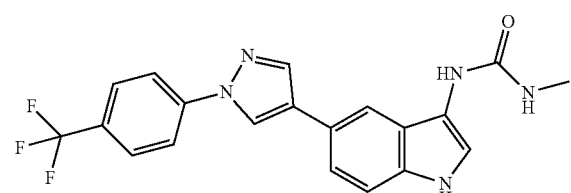 |
| 119 | 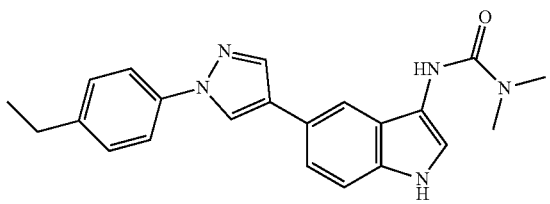 [SMILES: CCc1ccc(-n2cc(-c3ccc4[nH]cc(NC(=O)N(C)C)c4c3)cn2)cc1] |
| 120 | 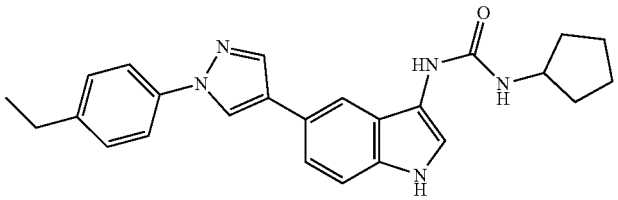 [SMILES: CCc1ccc(-n2cc(-c3ccc4[nH]cc(NC(=O)NC5CCCC5)c4c3)cn2)cc1] |
| 121 | 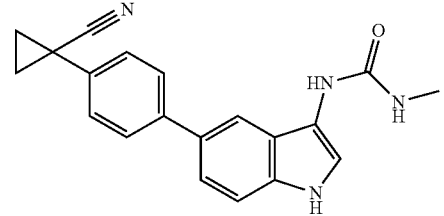 [SMILES: CNC(=O)Nc1c[nH]c2ccc(-c3ccc(C4(C#N)CC4)cc3)cc12] |

TABLE C1-continued

| Compound No. | Structure |
|---|---|
| 122 | 1-(5-(3-cyclopropylphenyl)-1H-indol-3-yl)-3-methylurea |
| 123 | 1-(5-(1-cyclopentyl-1H-pyrazol-4-yl)-1H-indol-3-yl)-3-methylurea |
| 124 | 1-(5-(1-(4-ethylphenyl)-1H-pyrazol-4-yl)-1H-indol-3-yl)-3-(tetrahydrofuran-3-yl)urea |
| 125 | 1-(5-(1-(4-ethylphenyl)-1H-pyrazol-4-yl)-1H-indol-3-yl)-3-(3-methoxycyclobutyl)urea |
| 126 | 1-cyclobutyl-3-(5-(1-(4-ethylphenyl)-1H-pyrazol-4-yl)-1H-indol-3-yl)urea |
| 127 | 1-(2,2-difluoroethyl)-3-(5-(1-(4-ethylphenyl)-1H-pyrazol-4-yl)-1H-indol-3-yl)urea |
| 128 | 1-(cyclopropylmethyl)-3-(5-(1-(4-ethylphenyl)-1H-pyrazol-4-yl)-1H-indol-3-yl)urea |

TABLE C1-continued

| Compound No. | Structure |
|---|---|
| 129 | (structure) |
| 130 | (structure) |
| 131 | (structure) |
| 132 | (structure) |

Pharmaceutical Compositions and Administration

General

In some embodiments, a chemical entity (e.g., a compound that inhibits (e.g., antagonizes) STING, or a pharmaceutically acceptable salt, and/or hydrate, and/or cocrystal, and/or drug combination thereof) is administered as a pharmaceutical composition that includes the chemical entity and one or more pharmaceutically acceptable excipients, and optionally one or more additional therapeutic agents as described herein.

In some embodiments, the chemical entities can be administered in combination with one or more conventional pharmaceutical excipients. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a chemical entity as described herein in the range of 0.005% to 100% with the balance made up from non-toxic excipient may be prepared. The contemplated compositions may contain 0.001%-100% of a chemical entity provided herein, in one embodiment 0.1-95%, in another embodiment 75-85%, in a further embodiment 20-80%. Actual methods of preparing such dosage forms are known, or will be apparent, to those skilled in this art; for example, see Remington: The Science and Practice of Pharmacy, 22$^{nd}$ Edition (Pharmaceutical Press, London, UK. 2012).

Routes of Administration and Composition Components

In some embodiments, the chemical entities described herein or a pharmaceutical composition thereof can be administered to subject in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal. In certain embodiments, a preferred route of administration is parenteral (e.g., intratumoral).

Compositions can be formulated for parenteral administration, e.g., formulated for injection via the intravenous, intramuscular, sub-cutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and the preparations can also be emulsified. The preparation of such formulations will be known to those of skill in the art in light of the present disclosure.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Intratumoral injections are discussed, e.g., in Lammers, et al., "*Effect of Intratumoral Injection on the Biodistribution and the Therapeutic Potential of HPMA Copolymer-Based Drug Delivery Systems*" Neoplasia. 2006, 10, 788-795.

Pharmacologically acceptable excipients usable in the rectal composition as a gel, cream, enema, or rectal suppository, include, without limitation, any one or more of cocoa butter glycerides, synthetic polymers such as polyvinylpyrrolidone, PEG (like PEG ointments), glycerine, glycerinated gelatin, hydrogenated vegetable oils, poloxamers, mixtures of polyethylene glycols of various molecular weights and fatty acid esters of polyethylene glycol Vaseline, anhydrous lanolin, shark liver oil, sodium sacchainate, menthol, sweet almond oil, sorbitol, sodium benzoate, anoxid SBN, vanilla essential oil, aerosol, parabens in phenoxyethanol, sodium methyl p-oxybenzoate, sodium propyl p-oxybenzoate, diethylamine, carbomers, carbopol, methyloxybenzoate, macrogol cetostearyl ether, cocoyl caprylocaprate, isopropyl alcohol, propylene glycol, liquid paraffin, xanthan gum, carboxy-metabisulfite, sodium edetate, sodium benzoate, potassium metabisulfite, grapefruit seed extract, methyl sulfonyl methane (MSM), lactic acid, glycine, vitamins, such as vitamin A and E and potassium acetate.

In certain embodiments, suppositories can be prepared by mixing the chemical entities described herein with suitable non-irritating excipients or carriers such as cocoa butter, polyethylene glycol or a suppository wax which are solid at ambient temperature but liquid at body temperature and therefore melt in the rectum and release the active compound. In other embodiments, compositions for rectal administration are in the form of an enema.

In other embodiments, the compounds described herein or a pharmaceutical composition thereof are suitable for local delivery to the digestive or GI tract by way of oral administration (e.g., solid or liquid dosage forms).

Solid dosage forms for oral administration include capsules, tablets, pills, powders, and granules. In such solid dosage forms, the chemical entity is mixed with one or more pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

In one embodiment, the compositions will take the form of a unit dosage form such as a pill or tablet and thus the composition may contain, along with a chemical entity provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which one or more chemical entities provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid.

In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

In certain embodiments, solid oral dosage forms can further include one or more components that chemically and/or structurally predispose the composition for delivery of the chemical entity to the stomach or the lower GI; e.g., the ascending colon and/or transverse colon and/or distal colon and/or small bowel. Exemplary formulation techniques are described in, e.g., Filipski, K. J., et al., *Current Topics in Medicinal Chemistry*, 2013, 13, 776-802, which is incorporated herein by reference in its entirety.

Examples include upper-GI targeting techniques, e.g., Accordion Pill (Intec Pharma), floating capsules, and materials capable of adhering to mucosal walls.

Other examples include lower-GI targeting techniques. For targeting various regions in the intestinal tract, several enteric/pH-responsive coatings and excipients are available. These materials are typically polymers that are designed to dissolve or erode at specific pH ranges, selected based upon the GI region of desired drug release. These materials also function to protect acid labile drugs from gastric fluid or limit exposure in cases where the active ingredient may be irritating to the upper GI (e.g., hydroxypropyl methylcellulose phthalate series, Coateric (polyvinyl acetate phthalate), cellulose acetate phthalate, hydroxypropyl methylcellulose acetate succinate, Eudragit series (methacrylic acid-methyl methacrylate copolymers), and Marcoat). Other techniques include dosage forms that respond to local flora in the GI tract, Pressure-controlled colon delivery capsule, and Pulsincap.

Ocular compositions can include, without limitation, one or more of any of the following: viscogens (e.g., Carboxymethylcellulose, Glycerin, Polyvinylpyrrolidone, Polyethylene glycol); Stabilizers (e.g., Pluronic (triblock copolymers), Cyclodextrins); Preservatives (e.g., Benzalkonium chloride, ETDA, SofZia (boric acid, propylene glycol, sorbitol, and zinc chloride; Alcon Laboratories, Inc.), Purite (stabilized oxychloro complex; Allergan, Inc.).

Topical compositions can include ointments and creams. Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. As with other carriers or vehicles, an ointment base should be inert, stable, nonirritating and non-sensitizing.

In any of the foregoing embodiments, pharmaceutical compositions described herein can include one or more one or more of the following: lipids, interbilayer crosslinked multilamellar vesicles, biodegradeable poly(D,L-lactic-co-glycolic acid) [PLGA]-based or poly anhydride-based nanoparticles or microparticles, and nanoporous particle-supported lipid bilayers.

Dosages

The dosages may be varied depending on the requirement of the patient, the severity of the condition being treating and the particular compound being employed. Determination of the proper dosage for a particular situation can be determined by one skilled in the medical arts. The total daily dosage may be divided and administered in portions throughout the day or by means providing continuous delivery.

In some embodiments, the compounds described herein are administered at a dosage of from about 0.001 mg/Kg to about 500 mg/Kg (e.g., from about 0.01 mg/Kg to about 100 mg/Kg; from about 0.01 mg/Kg to about 10 mg/Kg; from about 0.01 mg/Kg to about 1 mg/Kg; from about 0.01 mg/Kg to about 0.1 mg/Kg; from about 0.1 mg/Kg to about 100 mg/Kg; from about 0.1 mg/Kg to about 10 mg/Kg).

Regimens

The foregoing dosages can be administered on a daily basis (e.g., as a single dose or as two or more divided doses) or non-daily basis (e.g., every other day, every two days, every three days, once weekly, twice weeks, once every two weeks, once a month).

In some embodiments, the period of administration of a compound described herein is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In an embodiment, a therapeutic compound is administered to an individual for a period of time followed by a separate period of time. In another embodiment, a therapeutic compound is administered for a first period and a second period following the first period, with administration stopped during the second period, followed by a third period where administration of the therapeutic compound is started and then a fourth period following the third period where administration is stopped. In an aspect of this embodiment, the period of administration of a therapeutic compound followed by a period where administration is stopped is repeated for a determined or undetermined period of time. In a further embodiment, a period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

Methods of Treatment

In some embodiments, methods for treating a subject having condition, disease or disorder in which increased (e.g., excessive) STING activity (e.g., STING signaling) contributes to the pathology and/or symptoms and/or progression of the condition, disease or disorder (e.g., immune disorders, cancer) are provided.

Indications

In some embodiments, the condition, disease or disorder is cancer. Non-limiting examples of cancer include melanoma, carcinoma, lymphoma, blastoma, sarcoma, and leukemia or lymphoid malignancies. More particular examples of such cancers include breast cancer, colon cancer, rectal cancer, colorectal cancer, kidney or renal cancer, clear cell cancer lung cancer including small-cell lung cancer, non-small cell lung cancer, adenocarcinoma of the lung and squamous carcinoma of the lung, squamous cell cancer (e.g. epithelial squamous cell cancer), cervical cancer, ovarian cancer, prostate cancer, prostatic neoplasms, liver cancer, bladder cancer, cancer of the peritoneum, hepatocellular cancer, gastric or stomach cancer including gastrointestinal cancer, gastrointestinal stromal tumor, pancreatic cancer, head and neck cancer, glioblastoma, retinoblastoma, astrocytoma, thecomas, arrhenoblastomas, hepatoma, hematologic malignancies including non-Hodgkins lymphoma (NHL), multiple myeloma, myelodysplasia disorders, myeloproliferative disorders, chronic myelogenous leukemia, and acute hematologic malignancies, endometrial or uterine carcinoma, endometriosis, endometrial stromal sarcoma, fibrosarcomas, choriocarcinoma, salivary gland carcinoma, vulval cancer, thyroid cancer, esophageal carcinomas, hepatic carcinoma, anal carcinoma, penile carcinoma, nasopharyngeal carcinoma, laryngeal carcinomas, Kaposi's sarcoma, mast cell sarcoma, ovarian sarcoma, uterine sarcoma, melanoma, malignant mesothelioma, skin carcinomas, Schwannoma, oligodendroglioma, neuroblastomas, neuroectodermal tumor, rhabdomyosarcoma, osteogenic sarcoma, leiomyosarcomas, Ewing Sarcoma, peripheral primitive neuroectodermal tumor, urinary tract carcinomas, thyroid carcinomas, Wilm's tumor, as well as abnormal vascular proliferation associated with phakomatoses, edema (such as that associated with brain tumors), and Meigs' syndrome. In some cases, the cancer is melanoma.

In some embodiments, the condition, disease or disorder is a neurological disorder, which includes disorders that involve the central nervous system (brain, brainstem and cerebellum), the peripheral nervous system (including cranial nerves), and the autonomic nervous system (parts of which are located in both central and peripheral nervous system). Non-limiting examples of neurological disorders include acquired epileptiform aphasia; acute disseminated encephalomyelitis; adrenoleukodystrophy; age-related macular degeneration; agenesis of the corpus callosum; agnosia; Aicardi syndrome; Alexander disease; Alpers' disease; alternating hemiplegia; Alzheimer's disease; Vascular dementia; amyotrophic lateral sclerosis; anencephaly; Angelman syndrome; angiomatosis; anoxia; aphasia; apraxia; arachnoid cysts; arachnoiditis; Anronl-Chiari malformation; arteriovenous malformation; Asperger syndrome; ataxia telangiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome; causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy; chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease; cytomegalovirus infection; dancing eyes-dancing feet syndrome; Dandy-Walker syndrome; Dawson disease; De Morsier's syndrome; Dejerine-Klumke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; fronto-temporal dementia and other "tauopathies"; Gaucher's disease; Gerstmann's syndrome; giant cell arteritis; giant cell inclusion disease; globoid cell leukodystrophy; Guillain-Barre syndrome; HTLV-1-associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile phytanic acid storage disease; infantile refsum disease; infantile spasms; inflammatory myopathy; intracranial cyst; intracranial hypertension; Joubert syndrome; Kearns-Sayre syndrome; Kennedy disease Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gustaut syndrome; Lesch-Nyhan syndrome; leukodystrophy; Lewy body dementia; Lissencephaly; locked-in syndrome; Lou Gehrig's disease (i.e., motor neuron disease or amyotrophic lateral sclerosis); lumbar disc disease; Lyme disease—neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neuron disease; Moyamoya disease; mucopolysaccharidoses; multi-infarct dementia; multifocal motor neuropathy; multiple sclerosis and other demyelinating disorders; multiple system atrophy with postural hypotension; p muscular dystrophy; myasthenia gravis; myeloclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenital; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; post-polio syndrome; postherpetic neuralgia; postinfectious encephalomyelitis; postural hypotension; Prader-Willi syndrome; primary lateral sclerosis; prion diseases; progressive hemifacial atrophy; progressive multifocal leukoencephalopathy; progressive sclerosing poliodystrophy; progressive supranuclear palsy; pseudotumor cerebri; Ramsay-Hunt syndrome (types I and II); Rasmussen's encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus dance; Sandhoff disease; Schilder's disease; schizencephaly; septo-optic dysplasia; shaken baby syndrome; shingles; Shy-Drager syndrome; Sjögren's syndrome; sleep apnea; Soto's syndrome; spasticity; spina bifida; spinal cord injury; spinal cord tumors; spinal muscular atrophy; Stiff-Person syndrome; stroke; Sturge-Weber syndrome; subacute sclerosing panencephalitis; subcortical arteriosclerotic encephalopathy; Sydenham chorea; syncope; syringomyelia; tardive dyskinesia; Tay-Sachs disease; temporal arteritis; tethered spinal cord syndrome; Thomsen disease; thoracic outlet syndrome; Tic Douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau disease; Wallenberg's syndrome; Werdnig-Hoffman disease; West syndrome; whiplash; Williams syndrome; Wildon's disease; amyotrophe lateral sclerosis and Zellweger syndrome.

In some embodiments, the condition, disease or disorder is STING-associated conditions, e.g., type I interferonopathies (e.g., STING-associated vasculopathy with onset in infancy (SAVI)), Aicardi-Goutières Syndrome (AGS), genetic forms of lupus, and inflammation-associated disorders such as systemic lupus erythematosus, and rheumatoid arthritis. In certain embodiments, the condition, disease or disorder is an autoimmune disease (e.g., a cytosolic DNA-triggered autoinflammatory disease). Non-limiting examples include rheumatoid arthritis, systemic lupus erythematosus, multiple sclerosis, inflammatory bowel diseases (IBDs) comprising Crohn disease (CD) and ulcerative colitis (UC), which are chronic inflammatory conditions with polygenic susceptibility. In certain embodiments, the condition is an inflammatory bowel disease. In certain embodiments, the condition is Crohn's disease, autoimmune colitis, iatrogenic autoimmune colitis, ulcerative colitis, colitis induced by one or more chemotherapeutic agents, colitis induced by treatment with adoptive cell therapy, colitis associated by one or more alloimmune diseases (such as graft-vs-host disease, e.g., acute graft vs. host disease and chronic graft vs. host disease), radiation enteritis, collagenous colitis, lymphocytic colitis, microscopic colitis, and radiation enteritis. In certain of these embodiments, the condition is alloimmune disease (such as graft-vs-host disease, e.g., acute graft vs. host disease and chronic graft vs. host disease), celiac disease, irritable bowel syndrome, rheumatoid arthritis, lupus, scleroderma, psoriasis, cutaneous T-cell lymphoma, uveitis, and mucositis (e.g., oral mucositis, esophageal mucositis or intestinal mucositis).

In some embodiments, modulation of the immune system by STING provides for the treatment of diseases, including diseases caused by foreign agents. Exemplary infections by foreign agents which may be treated and/or prevented by the method of the present invention include an infection by a bacterium (e.g., a Gram-positive or Gram-negative bacterium), an infection by a fungus, an infection by a parasite, and an infection by a virus. In one embodiment of the present invention, the infection is a bacterial infection (e.g., infection by *E. coli, Klebsiella pneumoniae, Pseudomonas aeruginosa, Salmonella* spp., *Staphylococcus aureus, Streptococcus* spp., or vancomycin-resistant *enterococcus*), or sepsis. In another embodiment, the infection is a fungal infection (e.g. infection by a mould, a yeast, or a higher fungus). In still another embodiment, the infection is a parasitic infection (e.g., infection by a single-celled or multicellular parasite, including *Giardia duodenalis, Cryptosporidium parvum, Cyclospora cayetanensis,* and *Toxoplasma gondiz*). In yet another embodiment, the infection is a viral infection (e.g., infection by a virus associated with AIDS, avian flu, chickenpox, cold sores, common cold, gastroenteritis, glandular fever, influenza, measles, mumps, pharyngitis, pneumonia, rubella, SARS, and lower or upper respiratory tract infection (e.g., respiratory syncytial virus)).

In some embodiments, the condition, disease or disorder is hepatitis B (see, e.g., WO 2015/061294).

In some embodiments, the condition, disease or disorder is selected from cardiovascular diseases (including e.g., myocardial infarction).

In some embodiments, the condition, disease or disorder is age-related macular degeneration.

In some embodiments, the condition, disease or disorder is mucositis, also known as stomatitis, which can occur as a result of chemotherapy or radiation therapy, either alone or in combination as well as damage caused by exposure to radiation outside of the context of radiation therapy.

In some embodiments, the condition, disease or disorder is uveitis, which is inflammation of the uvea (e.g., anterior uveitis, e.g., iridocyclitis or iritis; intermediate uveitis (also known as pars planitis); posterior uveitis; or chorioretinitis, e.g., pan-uveitis).

In some embodiments, the condition, disease or disorder is selected from the group consisting of a cancer, a neurological disorder, an autoimmune disease, hepatitis B, uveitis, a cardiovascular disease, age-related macular degeneration, and mucositis.

Still other examples can include those indications discussed herein and below in contemplated combination therapy regimens.

Combination Therapy

This disclosure contemplates both monotherapy regimens as well as combination therapy regimens.

In some embodiments, the methods described herein can further include administering one or more additional therapies (e.g., one or more additional therapeutic agents and/or one or more therapeutic regimens) in combination with administration of the compounds described herein.

In certain embodiments, the methods described herein can further include administering one or more additional cancer therapies.

The one or more additional cancer therapies can include, without limitation, surgery, radiotherapy, chemotherapy, toxin therapy, immunotherapy, cryotherapy, cancer vaccines (e.g., HPV vaccine, hepatitis B vaccine, Oncophage, Provenge) and gene therapy, as well as combinations thereof. Immunotherapy, including, without limitation, adoptive cell therapy, the derivation of stem cells and/or dendritic cells, blood transfusions, lavages, and/or other treatments, including, without limitation, freezing a tumor.

In some embodiments, the one or more additional cancer therapies is chemotherapy, which can include administering one or more additional chemotherapeutic agents.

In certain embodiments, the additional chemotherapeutic agent is an immunomodulatory moiety, e.g., an immune checkpoint inhibitor. In certain of these embodiments, the immune checkpoint inhibitor targets an immune checkpoint receptor selected from the group consisting of CTLA-4, PD-1, PD-L1, PD-1-PD-L1, PD-1-PD-L2, interleukin-2 (IL-2), indoleamine 2,3-dioxygenase (IDO), IL-10, transforming growth factor-β (TGFβ), T cell immunoglobulin and mucin 3 (TIM3 or HAVCR2), Galectin 9-TIM3, Phosphatidylserine-TIM3, lymphocyte activation gene 3 protein (LAG3), MHC class II-LAG3, 4-1BB-4-1BB ligand, OX40-OX40 ligand, GITR, GITR ligand-GITR, CD27, CD70-CD27, TNFRSF25, TNFRSF25-TL1A, CD40L, CD40-CD40 ligand, HVEM-LIGHT-LTA, HVEM, HVEM-BTLA, HVEM-CD160, HVEM-LIGHT, HVEM-BTLA-CD160, CD80, CD80-PDL-1, PDL2-CD80, CD244, CD48-CD244, CD244, ICOS, ICOS-ICOS ligand, B7-H3, B7-H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86-CD28, CD86-CTLA, CD80-CD28, CD39, CD73 Adenosine-CD39-CD73, CXCR4-CXCL12, Phosphatidylserine, TIM3, Phosphatidylserine-TIM3, SIRPA-CD47, VEGF, Neuropilin, CD160, CD30, and CD155; e.g., CTLA-4 or PD1 or PD-L1). See, e.g., Postow, M. *J. Clin. Oncol.* 2015, 33, 1.

In certain of these embodiments, the immune checkpoint inhibitor is selected from the group consisting of: Urelumab, PF-05082566, MEDI6469, TRX518, Varlilumab, CP-870893, Pembrolizumab (PD1), Nivolumab (PD1), Atezolizumab (formerly MPDL3280A) (PDL1), MEDI4736 (PD-L1), Avelumab (PD-L1), PDR001 (PD1), BMS-986016, MGA271, Lirilumab, IPH2201, Emactuzumab, INCB024360, Galunisertib, Ulocuplumab, BKT140, Bavituximab, CC-90002, Bevacizumab, and MNRP1685A, and MGA271.

In certain embodiments, the additional chemotherapeutic agent is an alkylating agent. Alkylating agents are so named because of their ability to alkylate many nucleophilic functional groups under conditions present in cells, including, but not limited to cancer cells. In a further embodiment, an alkylating agent includes, but is not limited to, Cisplatin, carboplatin, mechlorethamine, cyclophosphamide, chlorambucil, ifosfamide and/or oxaliplatin. In an embodiment, alkylating agents can function by impairing cell function by forming covalent bonds with the amino, carboxyl, sulfhydryl, and phosphate groups in biologically important molecules or they can work by modifying a cell's DNA. In a further embodiment an alkylating agent is a synthetic, semisynthetic or derivative.

In certain embodiments, the additional chemotherapeutic agent is an anti-metabolite. Anti-metabolites masquerade as purines or pyrimidines, the building-blocks of DNA and in general, prevent these substances from becoming incorporated in to DNA during the "S" phase (of the cell cycle), stopping normal development and division. Anti-metabolites can also affect RNA synthesis. In an embodiment, an antimetabolite includes, but is not limited to azathioprine and/or mercaptopurine. In a further embodiment an antimetabolite is a synthetic, semisynthetic or derivative.

In certain embodiments, the additional chemotherapeutic agent is a plant alkaloid and/or terpenoid. These alkaloids are derived from plants and block cell division by, in general, preventing microtubule function. In an embodiment, a plant alkaloid and/or terpenoid is a vinca alkaloid, a podophyllotoxin and/or a taxane. Vinca alkaloids, in general, bind to specific sites on tubulin, inhibiting the assembly of tubulin into microtubules, generally during the M phase of the cell cycle. In an embodiment, a vinca alkaloid is derived, without limitation, from the Madagascar periwinkle, *Catharanthus roseus* (formerly known as *Vinca rosea*). In an embodiment, a vinca alkaloid includes, without limitation, Vincristine, Vinblastine, Vinorelbine and/or Vindesine. In an embodiment, a taxane includes, but is not limited to, Taxol, Paclitaxel and/or Docetaxel.

In a further embodiment a plant alkaloid or terpenoid is a synthetic, semisynthetic or derivative. In a further embodiment, a podophyllotoxin is, without limitation, an etoposide and/or teniposide. In a further embodiment, a taxane is, without limitation, docetaxel and/or ortataxel. In an embodiment, a cancer therapeutic is a topoisomerase. Topoisomerases are essential enzymes that maintain the topology of DNA. Inhibition of type I or type II topoisomerases interferes with both transcription and replication of DNA by upsetting proper DNA supercoiling. In a further embodiment, a topoisomerase is, without limitation, a type I topoisomerase inhibitor or a type II topoisomerase inhibitor. In an embodiment a type I topoisomerase inhibitor is, without limitation, a camptothecin. In another embodiment, a camptothecin is, without limitation, exatecan, irinotecan, lurtotecan, topotecan, BNP 1350, CKD 602, DB 67 (AR67) and/or ST 1481. In an embodiment, a type II topoisomerase inhibitor is, without limitation, epipodophyllotoxin. In a further embodiment an epipodophyllotoxin is, without limitation, an amsacrine, etoposid, etoposide phosphate and/or teniposide. In a further embodiment a topoisomerase is a synthetic, semisynthetic or derivative, including those found in nature such as, without limitation, epipodophyllotoxins, substances naturally occurring in the root of American Mayapple (*Podophyllum peltatum*).

In certain embodiments, the additional chemotherapeutic agent is a stilbenoid. In a further embodiment, a stilbenoid includes, but is not limited to, Resveratrol, Piceatannol, Pinosylvin, Pterostilbene, Alpha-Viniferin, Ampelopsin A, Ampelopsin E, Diptoindonesin C, Diptoindonesin F, Epsilon-Vinferin, Flexuosol A, Gnetin H, Hemsleyanol D, Hopeaphenol, Trans-Diptoindonesin B, Astringin, Piceid and Diptoindonesin A. In a further embodiment a stilbenoid is a synthetic, semisynthetic or derivative.

In certain embodiments, the additional chemotherapeutic agent is a cytotoxic antibiotic. In an embodiment, a cytotoxic antibiotic is, without limitation, an actinomycin, an anthracenedione, an anthracycline, thalidomide, dichloroacetic acid, nicotinic acid, 2-deoxyglucose and/or chlofazimine. In an embodiment, an actinomycin is, without limitation, actinomycin D, bacitracin, colistin (polymyxin E) and/or polymyxin B. In another embodiment, an antracenedione is, without limitation, mitoxantrone and/or pixantrone. In a further embodiment, an anthracycline is, without limitation, bleomycin, doxorubicin (Adriamycin), daunorubicin (daunomycin), epirubicin, idarubicin, mitomycin, plicamycin and/or valrubicin. In a further embodiment a cytotoxic antibiotic is a synthetic, semisynthetic or derivative.

In certain embodiments, the additional chemotherapeutic agent is selected from endostatin, angiogenin, angiostatin, chemokines, angioarrestin, angiostatin (plasminogen fragment), basement-membrane collagen-derived anti-angiogenic factors (tumstatin, canstatin, or arrestin), anti-angiogenic antithrombin III, signal transduction inhibitors, cartilage-derived inhibitor (CDI), CD59 complement fragment, fibronectin fragment, gro-beta, heparinases, heparin hexasaccharide fragment, human chorionic gonadotropin (hCG), interferon alpha/beta/gamma, interferon inducible protein (IP-10), interleukin-12, kringle 5 (plasminogen fragment), metalloproteinase inhibitors (TIMIPs), 2-methoxyestradiol, placental ribonuclease inhibitor, plasminogen activator inhibitor, platelet factor-4 (PF4), prolactin 16 kD fragment, proliferin-related protein (PRP), various retinoids, tetrahydrocortisol-S, thrombospondin-1 (TSP-1), transforming growth factor-beta (TGF-0), vasculostatin, vasostatin (calreticulin fragment) and the like.

In certain embodiments, the additional chemotherapeutic agent is selected from abiraterone acetate, altretamine, anhydrovinblastine, auristatin, bexarotene, bicalutamide, BMS 184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly-1-Lproline-t-butylamide, cachectin, cemadotin, chlorambucil, cyclophosphamide, 3',4'-didehydro-4'-deoxy-8'-norvincaleukoblastine, docetaxol, doxetaxel, cyclophosphamide, carboplatin, carmustine, cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), MDV3100, mechlorethamine (nitrogen mustard), melphalan, mivobulin isethionate, rhizoxin, sertenef, streptozocin, mitomycin, methotrexate, taxanes, nilutamide, onapristone, paclitaxel, prednimustine, procarbazine, RPR109881, stramustine phosphate, tamoxifen, tasonermin, taxol, tretinoin, vinblastine, vincristine, vindesine sulfate, and vinflunine.

In certain embodiments, the additional chemotherapeutic agent is platinum, cisplatin, carboplatin, oxaliplatin, mechlorethamine, cyclophosphamide, chlorambucil, azathioprine, mercaptopurine, vincristine, vinblastine, vinorelbine, vindesine, etoposide and teniposide, paclitaxel, docetaxel, irinotecan, topotecan, amsacrine, etoposide, etoposide phosphate, teniposide, 5-fluorouracil, leucovorin, methotrexate, gemcitabine, taxane, leucovorin, mitomycin C, tegafur-uracil, idarubicin, fludarabine, mitoxantrone, ifosfamide and doxorubicin. Additional agents include inhibitors of mTOR (mammalian target of rapamycin), including but not limited to rapamycin, everolimus, temsirolimus and deforolimus.

In still other embodiments, the additional chemotherapeutic agent can be selected from those delineated in U.S. Pat. No. 7,927,613, which is incorporated herein by reference in its entirety.

In some embodiments, the additional therapeutic agent and/or regimen are those that can be used for treating other STING-associated conditions, e.g., type I interferonopathies (e.g., STING-associated vasculopathy with onset in infancy (SAVI)), Aicardi-Goutières Syndrome (AGS), genetic forms of lupus, and inflammation-associated disorders such as systemic lupus erythematosus, and rheumatoid arthritis and the like.

Non-limiting examples of additional therapeutic agents and/or regimens for treating rheumatoid arthritis include non-steroidal anti-inflammatory drugs (NSAIDs; e.g., ibuprofen and naproxen), corticosteroids (e.g., prednisone), disease-modifying antirheumatic drugs (DMARDs; e.g., methotrexate (Trexall®, Otrexup®, Rasuvo®, Rheumatrex®), leflunomide (Arava®), hydroxychloroquine (Plaquenil), PF-06650833, iguratimod, tofacitinib (Xeljanz®), ABBV-599, evobrutinib, and sulfasalazine (Azulfidine®)), and biologics (e.g., abatacept (Orencia®), adalimumab (Humira®), anakinra (Kineret®), certolizumab (Cimzia®), etanercept (Enbrel®), golimumab (Simponi®), infliximab (Remicade®), rituximab (Rituxan®), tocilizumab (Actemra®), vobarilizumab, sarilumab (Kevzara®), secukinumab, ABP 501, CHS-0214, ABC-3373, and tocilizumab (ACTEMRA®)).

Non-limiting examples of additional therapeutic agents and/or regimens for treating lupus include steroids, topical immunomodulators (e.g., tacrolimus ointment (Protopic®) and pimecrolimus cream (Elidel®)), thalidomide (Thalomid®), non-steroidal anti-inflammatory drugs (NSAIDs; e.g., ibuprofen and naproxen), antimalarial drugs (e.g., Hydroxychloroquine (Plaquenil)), corticosteroids (e.g, prednisone) and immunomodulators (e.g., evobrutinib, iberdomide, voclosporin, cenerimod, azathioprine (Imuran®), cyclophosphamide (Cytoxan®, Neosar®, Endoxan®), and cyclosporine (Neoral, Sandimmune®, Gengraf®), and mycophenolate mofetil) baricitinb, iguratimod, filogotinib, GS-9876, rapamycin, and PF-06650833), and biologics (e.g., belimumab (Benlysta®), anifrolumab, prezalumab, M1EDIO700, obinutuzumab, vobarilizumab, lulizumab, atacicept, PF-06823859, and lupizor, rituximab, BT063, BI655064, BIIB059, aldesleukin (Proleukin®), dapirolizumab, edratide, IFN-α-kinoid, OMS721, RC18, RSLV-132, theralizumab, XmAb5871, and ustekinumab (Stelara®)). For example, non-limiting treatments for systemic lupus erythematosus include non-steroidal anti-inflammatory drugs (NSAIDs; e.g., ibuprofen and naproxen), antimalarial drugs (e.g., Hydroxychloroquine (Plaquenil)), corticosteroids (e.g, prednisone) and immunomodulators (e.g., iberdomide, voclosporin, azathioprine (Imuran®), cyclophosphamide (Cytoxan®, Neosar®, Endoxan®), and cyclosporine (Neoral, Sandimmune®, Gengraf®), and mycophenolate mofetil, baricitinb, filogotinib, and PF-06650833), and biologics (e.g., belimumab (Benlysta®), anifrolumab, prezalumab, MEDI0700, vobarilizumab, lulizumab, atacicept, PF-06823859, lupizor, rituximab, BT063, BI655064, BIIB059, aldesleukin (Proleukin®), dapirolizumab, edratide, IFN-α-kinoid, RC18, RSLV-132, theralizumab, XmAb5871, and ustekinumab (Stelara®)). As another example, non-limiting examples of treatments for cutaneous lupus include steroids, immunomodulators (e.g., tacrolimus ointment (Protopic®) and pimecrolimus cream (Elidel®)), GS-9876, filogotinib, and thalidomide (Thalomid®). Agents and regimens for treating drug-induced and/or neonatal lupus can also be administered.

Non-limiting examples of additional therapeutic agents and/or regimens for treating STING-associated vasculopathy with onset in infancy (SAVI) include JAK inhibitors (e.g., tofacitinib, ruxolitinib, filgotinib, and baricitinib).

Non-limiting examples of additional therapeutic agents and/or regimens for treating Aicardi-Goutières Syndrome (AGS) include physiotherapy, treatment for respiratory complications, anticonvulsant therapies for seizures, tube-feeding, nucleoside reverse transcriptase inhibitors (e.g., emtricitabine (e.g., Emtriva®), tenofovir (e.g., Viread®), emtricitabine/tenofovir (e.g., Truvada®), zidovudine, lamivudine, and abacavir), and JAK inhibitors (e.g., tofacitinib, ruxolitinib, filgotinib, and baricitinib).

Non-limiting examples of additional therapeutic agents and/or regimens for treating IBDs include 6-mercaptopurine, AbGn-168H, ABX464, ABT-494, adalimumab, AJM300, alicaforsen, AMG139, anrukinzumab, apremilast, ATR-107 (PF0530900), autologous CD34-selected peripheral blood stem cells transplant, azathioprine, bertilimumab, BI 655066, BMS-936557, certolizumab pegol (Cimzia®), cobitolimod, corticosteroids (e.g., prednisone, Methylprednisolone, prednisone), CP-690,550, CT-P13, cyclosporine, DIMS0150, E6007, E6011, etrasimod, etrolizumab, fecal microbial transplantation, figlotinib, fingolimod, firategrast (SB-683699) (formerly T-0047), GED0301, GLPG0634, GLPG0974, guselkumab, golimumab, GSK1399686, HMPL-004 (*Andrographis paniculata* extract), IMU-838, infliximab, Interleukin 2 (IL-2), Janus kinase (JAK) inhibitors, laquinimod, masitinib (AB1010), matrix metalloproteinase 9 (MMP 9) inhibitors (e.g., GS-5745), MEDI2070, mesalamine, methotrexate, mirikizumab (LY3074828), natalizumab, NNC 0142-0000-0002, NNC0114-0006, ozanimod, peficitinib (JNJ-54781532), PF-00547659, PF-04236921, PF-06687234, QAX576, RHB-104, rifaximin, risankizumab, RPC1063, SB012, SHP647, sulfasalazine, TD-1473, thalidomide, tildrakizumab (MK 3222), TJ301, TNF-Kinoid®, tofacitinib, tralokinumab, TRK-170, upadacitinib, ustekinumab, UTTR1147A, V565, vatelizumab, VB-201, vedolizumab, and vidofludimus.

Non-limiting examples of additional therapeutic agents and/or regimens for treating irritable bowel syndrome include alosetron, bile acid sequestrants (e.g., cholestyramine, colestipol, colesevelam), chloride channel activators (e.g., lubiprostone), coated peppermint oil capsules, desipramine, dicyclomine, ebastine, eluxadoline, farnesoid X receptor agonist (e.g., obeticholic acid), fecal microbiota transplantation, fluoxetine, gabapentin, guanylate cyclase-C agonists (e.g., linaclotide, plecanatide), ibodutant, imipramine, JCM-16021, loperamide, lubiprostone, nortriptyline, ondansetron, opioids, paroxetine, pinaverium, polyethylene glycol, pregabalin, probiotics, ramosetron, rifaximin, and tanpanor.

Non-limiting examples of additional therapeutic agents and/or regimens for treating scleroderma include non-steroidal anti-inflammatory drugs (NSAIDs; e.g., ibuprofen and naproxen), corticosteroids (e.g, prednisone), immunomodulators (e.g., azathioprine, methotrexate (Trexall®, Otrexup®, Rasuvo®, Rheumatrex®), cyclophosphamide (Cytoxan®, Neosar®, Endoxan®), and cyclosporine (Neoral®, Sandimmune®, Gengraf®), antithymocyte globulin, mycophenolate mofetil, intravenous immunoglobulin, rituximab, sirolimus, and alefacept), calcium channel blockers (e.g., nifedipine), alpha blockers, serotonin receptor antagonists, angiotensin II receptor inhibitors, statins, local nitrates, iloprost, phosphodiesterase 5 inhibitors (e.g., sildenafil), bosentan, tetracycline antibiotics, endothelin receptor antagonists, prostanoids, and tyrosine kinase inhibitors (e.g., imatinib, nilotinib and dasatinib).

Non-limiting examples of additional therapeutic agents and/or regimens for treating Crohn's Disease (CD) include adalimumab, autologous CD34-selected peripheral blood stem cells transplant, 6-mercaptopurine, azathioprine, certolizumab pegol (Cimzia®), corticosteroids (e.g., prednisone), etrolizumab, E6011, fecal microbial transplantation, figlotinib, guselkumab, infliximab, IL-2, JAK inhibitors, matrix metalloproteinase 9 (MMP 9) inhibitors (e.g., GS-5745), MEDI2070, mesalamine, methotrexate, natalizumab, ozanimod, RHB-104, rifaximin, risankizumab, SHP647, sulfasalazine, thalidomide, upadacitinib, V565, and vedolizumab.

Non-limiting examples of additional therapeutic agents and/or regimens for treating UC include AbGn-168H, ABT-494, ABX464, apremilast, PF-00547659, PF-06687234, 6-mercaptopurine, adalimumab, azathioprine, bertilimumab, brazikumab (MEDI2070), cobitolimod, certolizumab pegol (Cimzia®), CP-690,550, corticosteroids (e.g., multimax budesonide, Methylprednisolone), cyclosporine, E6007, etrasimod, etrolizumab, fecal microbial transplantation, figlotinib, guselkumab, golimumab, IL-2, IMU-838, infliximab, matrix metalloproteinase 9 (MMP9) inhibitors (e.g., GS-5745), mesalamine, mesalamine, mirikizumab (LY3074828), RPC1063, risankizumab (BI 6555066), SHP647, sulfasalazine, TD-1473, TJ301, tildrakizumab (MK 3222), tofacitinib, tofacitinib, ustekinumab, UTTR1147A, and vedolizumab.

Non-limiting examples of additional therapeutic agents and/or regimens for treating autoimmune colitis include corticosteroids (e.g., budesonide, prednisone, prednisolone, Beclometasone dipropionate), diphenoxylate/atropine, infliximab, loperamide, mesalamine, TIP60 inhibitors (see, e.g., U.S. Patent Application Publication No. 2012/0202848), and vedolizumab.

Non-limiting examples of additional therapeutic agents and/or regimens for treating iatrogenic autoimmune colitis include corticosteroids (e.g., budesonide, prednisone, prednisolone, Beclometasone dipropionate), diphenoxylate/atropine, infliximab, loperamide, TIP60 inhibitors (see, e.g., U.S. Patent Application Publication No. 2012/0202848), and vedolizumab.

Non-limiting examples of additional therapeutic agents and/or regimens for treating colitis induced by one or more chemotherapeutics agents include corticosteroids (e.g., budesonide, prednisone, prednisolone, beclometasone dipropionate), diphenoxylate/atropine, infliximab, loperamide, mesalamine, TIP60 inhibitors (see, e.g., U.S. Patent Application Publication No. 2012/0202848), and vedolizumab.

Non-limiting examples of additional therapeutic agents and/or regimens for treating colitis induced by treatment with adoptive cell therapy include corticosteroids (e.g., budesonide, prednisone, prednisolone, beclometasone dipropionate), diphenoxylate/atropine, infliximab, loperamide, TIP60 inhibitors (see, e.g., U.S. Patent Application Publication No. 2012/0202848), and vedolizumab.

Non-limiting examples of additional therapeutic agents and/or regimens for treating colitis associated with one or more alloimmune diseases include corticosteroids (e.g., budesonide, prednisone, prednisolone, beclometasone dipropionate), sulfasalazine, and eicopentaenoic acid.

Non-limiting examples of additional therapeutic agents and/or regimens for treating radaiation enteritis include teduglutide, amifostine, angiotensin-converting enzyme (ACE) inhibitors (e.g., benazepril, captopril, enalapril, fosinopril, lisinopril, moexipril, perindopril, quinapril, ramipril, and trandolapril), probiotics, selenium supplementation, statins (e.g., atorvastatin, fluvastatin, lovastatin, pravastatin, rosuvastatin, simvastatin, and pitavastatin), sucralfate, and vitamin E.

Non-limiting examples of additional therapeutic agents and/or regimens for treating collagenous colitis include 6-mercaptopurine, azathaioprine, bismuth subsalicate, *Boswellia serrata* extract, cholestyramine, colestipol, corticosteroids (e.g., budesonide, prednisone, prednisolone, beclometasone dipropionate), loperamide, mesalamine, methotrexate, probiotics, and sulfasalazine.

Non-limiting examples of additional therapeutic agents and/or regimens for treating lymphocytic colitis include 6-mercaptopurine, azathioprine, bismuth subsalicylate, cholestyramine, colestipol, corticosteroids (e.g., budesonide, prednisone, prednisolone, beclometasone dipropionate), loperamide, mesalamine, methotrexate, and sulfasalazine.

Non-limiting examples of additional therapeutic agents and/or regimens for treating microscopic colitis include 6-mercaptopurine, azathioprine, bismuth subsalicylate, *Boswellia serrata* extract, cholestyramine, colestipol, corticosteroids (e.g., budesonide, prednisone, prednisolone, beclometasone dipropionate), fecal microbial transplantation, loperamide, mesalamine, methotrexate, probiotics, and sulfasalazine.

Non-limiting examples of additional therapeutic agents and/or regimens for treating alloimmune disease include intrauterine platelet transfusions, intravenous immunoglobin, maternal steroids, abatacept, alemtuzumab, alpha1-antitrypsin, AMG592, antithymocyte globulin, barcitinib, basiliximab, bortezomib, brentuximab, cannabidiol, corticosteroids (e.g., methylprednisone, prednisone), cyclosporine, dacilzumab, defribrotide, denileukin diftitox, glasdegib, ibrutinib, IL-2, infliximab, itacitinib, LBH589, maraviroc, mycophenolate mofetil, natalizumab, neihulizumab, pentostatin, pevonedistat, photobiomodulation, photopheresis, ruxolitinib, sirolimus, sonidegib, tacrolimus, tocilizumab, and vismodegib.

Non-limiting examples of additional therapeutic agents and/or regimens for treating multiple sclerosis (MS) include alemtuzumab (Lemtrada®), ALKS 8700, amiloride, ATX-MS-1467, azathioprine, baclofen (Lioresal®), beta interferons (e.g., IFN-β-1a, IFN-β-1b), cladribine, corticosteroids (e.g., methylprednisolone), daclizumab, dimethyl fumarate (Tecfidera®), fingolimod (Gilenya®), fluoxetine, glatiramer acetate (Copaxone®), hydroxychloroquine, ibudilast, idebenone, laquinimod, lipoic acid, losartan, masitinib, MD1003 (biotin), mitoxantrone, montelukast, natalizumab (Tysabri®), NeuroVax™, ocrelizumab, ofatumumab, pioglitazone, and RPC1063.

Non-limiting examples of additional therapeutic agents and/or regimens for treating graft-vs-host disease include abatacept, alemtuzumab, alpha1-antitrypsin, AMG592, antithymocyte globulin, barcitinib, basiliximab, bortezomib, brentuximab, cannabidiol, corticosteroids (e.g., methylprednisone, prednisone), cyclosporine, dacilzumab, defribrotide, denileukin diftitox, glasdegib, ibrutinib, IL-2, imatinib, infliximab, itacitinib, LBH589, maraviroc, mycophenolate mofetil, natalizumab, neihulizumab, pentostatin, pevonedistat, photobiomodulation, photopheresis, ruxolitinib, sirolimus, sonidegib, tacrolimus, tocilizumab, and vismodegib.

Non-limiting examples of additional therapeutic agents and/or regimens for treating acute graft-vs-host disease include alemtuzumab, alpha-1 antitrypsin, antithymocyte globulin, basiliximab, brentuximab, corticosteroids (e.g., methylprednisone, prednisone), cyclosporine, dacilzumab, defribrotide, denileukin diftitox, ibrutinib, infliximab, itacitinib, LBH589, mycophenolate mofetil, natalizumab, neihulizumab, pentostatin, photopheresis, ruxolitinib, sirolimus, tacrolimus, and tocilizumab.

Non-limiting examples of additional therapeutic agents and/or regimens for treating chronic graft vs. host disease include abatacept, alemtuzumab, AMG592, antithymocyte globulin, basiliximab, bortezomib, corticosteroids (e.g., methylprednisone, prednisone), cyclosporine, dacilzumab, denileukin diftitox, glasdegib, ibrutinib, IL-2, imatinib, infliximab, mycophenolate mofetil, pentostatin, photobiomodulation, photopheresis, ruxolitinib, sirolimus, sonidegib, tacrolimus, tocilizumab, and vismodegib.

Non-limiting examples of additional therapeutic agents and/or regimens for treating celiac disease include AMG 714, AMY01, *Aspergillus niger* prolyl endoprotease, BL-7010, CALY-002, GBR 830, Hu-Mik-Beta-1, IMGX003, KumaMax, Larazotide Acetate, Nexvan2®, pancrelipase, TIMP-GLIA, vedolizumab, and ZED1227.

Non-limiting examples of additional therapeutic agents and/or regimens for treating psoriasis include topical corticosteroids, topical crisaborole/AN2728, topical SNA-120, topical SAN021, topical tapinarof, topical tocafinib, topical IDP-118, topical M518101, topical calcipotriene and betamethasone dipropionate (e.g., MC2-01 cream and Taclonex®), topical P-3073, topical LEO 90100 (Enstilar®), topical betamethasone dipropriate (Sernivo®), halobetasol propionate (Ultravate®), vitamin D analogues (e.g., calcipotriene (Dovonex®) and calcitriol (Vectical®)), anthralin (e.g., Dritho-Scalp® and Dritho-Creme®), topical retinoids (e.g., tazarotene (e.g., Tazorac® and Avage®)), calcineurin inhibitors (e.g., tacrolimus (Prograf®) and pimecrolimus (Elidel®)), salicylic acid, coal tar, moisturizers, phototherapy (e.g., exposure to sunlight, UVB phototherapy, narrow band UVB phototherapy, Goeckerman therapy, psoralen plus ultraviolet A (PUVA) therapy, and excimer laser), retinoids (e.g., acitretin (Soriatane®)), methotrexate (Trexall®, Otrexup®, Rasuvo®, Rheumatrex®), Apo805K1, baricitinib, FP187, KD025, prurisol, VTP-43742, XP23829, ZPL-389, CF101 (piclidenoson), LAS41008, VPD-737 (serlopitant), upadacitinib (ABT-494), aprmilast, tofacitibin, cyclosporine (Neoral®, Sandimmune®, Gengraf®), biologics (e.g., etanercept (Enbrel®), entanercept-szzs (Elrezi®), infliximab (Remicade®), adalimumab (Humira®), adalimumab-adbm (Cyltezo®), ustekinumab (Stelara®), golimumab (Simponi®), apremilast (Otezla®), secukinumab (Cosentyx®), certolixumab pegol, secukinumab, tildrakizumab-asmn, infliximab-dyyb, abatacept, ixekizumab (Taltz®), ABP 710, BCD-057, BI695501, bimekizumab (UCB4940), CHS-1420, GP2017, guselkumab (CNTO 1959), HD203, M923, MSB11022, Mirikizumab (LY3074828), PF-06410293, PF-06438179, risankizumab (BI655066), SB2, SB4, SB5, siliq (brodalumab), namilumab (MT203, tildrakizumab (MK-3222), and ixekizumab (Taltz®)), thioguanine, and hydroxyurea (e.g., Droxia® and Hydrea®).

Non-limiting examples of additional therapeutic agents and/or regimens for treating cutaneous T-cell lymphoma include phototherapy (e.g., exposure to sunlight, UVB phototherapy, narrow band UVB phototherapy, Goeckerman therapy, psoralen plus ultraviolet A (PUVA) therapy, and excimer laser), extracorporeal photopheresis, radiation therapy (e.g., spot radiation and total skin body electron beam therapy), stem cell transplant, corticosteroids, imiquimod, bexarotene gel, topical bis-chloroethyl-nitrourea, mechlorethamine gel, vorinostat (Zolinza®), romidepsin (Istodax®), pralatrexate (Folotyn®) biologics (e.g., alemtuzumab (Campath®), brentuximab vedotin (SGN-35), mogamulizumab, and IPH4102).

Non-limiting examples of additional therapeutic agents and/or regimens for treating uveitis include corticosteroids (e.g., intravitreal triamcinolone acetonide injectable suspensions), antibiotics, antivirals (e.g., acyclovir), dexamethasone, immunomodulators (e.g., tacrolimus, leflunomide, cyclophosphamide (Cytoxan®, Neosar®, Endoxan®), and cyclosporine (Neoral®, Sandimmune®, Gengraf®), chlorambucil, azathioprine, methotrexate, and mycophenolate mofetil), biologics (e.g., infliximab (Remicade®), adalimumab (Humira®), etanercept (Enbrel®), golimumab (Simponi®), certolizumab (Cimzia®), rituximab (Rituxan®), abatacept (Orencia®), basiliximab (Simulect®), anakinra (Kineret®), canakinumab (Ilaris®), gevokixumab (XOMA052), tocilizumab (Actemra®), alemtuzumab (Campath®), efalizumab (Raptiva®), LFG316, sirolimus (Santen®), abatacept, sarilumab (Kevzara®), and daclizumab (Zenapax®)), cytotoxic drugs, surgical implant (e.g., fluocinolone insert), and vitrectomy.

on-limiting examples of additional therapeutic agents and/or regimens for treating mucositis include AG013, SGX942 (dusquetide), amifostine (Ethyol®), cryotherapy, cepacol lonzenges, capsaicin lozenges, mucoadhesives (e.g., MuGard®) oral diphenhydramine (e.g., Benadry® elixir), oral bioadherents (e.g., polyvinylpyrrolidone-sodium hyaluronate gel (Gelclair®)), oral lubricants (e.g., Oral Balance®), caphosol, *Chamomilla recutita* mouthwash, edible grape plant exosome, antiseptic mouthwash (e.g., chlorhexidine gluconate (e.g., Peridex® or Periogard®), topical pain relievers (e.g., lidocaine, benzocaine, dyclonine hydrochloride, xylocaine (e.g., viscous xylocaine 2%), and Ulcerease® (0.6% phenol)), corticosteroids (e.g., prednisone), pain killers (e.g., ibuprofen, naproxen, acetaminophen, and opioids), GC4419, palifermin (keratinocyte growth factor; Kepivance®), ATL-104, clonidine lauriad, IZN-6N4, SGX942, rebamipide, nepidermin, soluble β-1,3/1,6 glucan, P276, LP-0004-09, CR-3294, ALD-518, IZN-6N4, quercetin, granules comprising *Vaccinium myrtillus* extract, *Macleaya cordata* alkaloids and *Echinacea angustifolia* extract (e.g., SAMITAL®), and gastrointestinal cocktail (an acid reducer such aluminum hydroxide and magnesium hydroxide (e.g., Maalox), an antifungal (e.g., nystatin), and an analgesic (e.g., hurricane liquid)). For example, non-limiting examples of treatments for oral mucositis include AG013, amifostine (Ethyol®), cryotherapy, cepacol lonzenges, mucoadhesives (e.g., MuGard®) oral diphenhydramine (e.g., Benadry® elixir), oral bioadherents (e.g., polyvinylpyrrolidone-sodium hyaluronate gel (Gelclair®)), oral lubricants (e.g., Oral Balance®), caphosol, *Chamomilla recutita* mouthwash, edible grape plant exosome, antiseptic mouthwash (e.g., chlorhexidine gluconate (e.g., Peridex® or Periogard®), topical pain relievers (e.g., lidocaine, benzocaine, dyclonine hydrochloride, xylocaine (e.g., viscous xylocaine 2%), and Ulcerease® (0.6% phenol)), corticosteroids (e.g., prednisone), pain killers (e.g., ibuprofen, naproxen, acetaminophen, and opioids), GC4419, palifermin (keratinocyte growth factor; Kepivance®), ATL-104, clonidine lauriad, IZN-6N4, SGX942, rebamipide, nepidermin, soluble β-1,3/1,6 glucan, P276, LP-0004-09, CR-3294, ALD-518, IZN-6N4, quercetin, and gastrointestinal cocktail (an acid reducer such aluminum hydroxide and magnesium hydroxide (e.g., Maalox), an antifungal (e.g., nystatin), and an analgesic (e.g., hurricane liquid)). As another example, non-limiting examples of treatments for esophageal mucositis include xylocaine (e.g., gel viscous Xylocaine 2%). As another example, treatments for intestinal mucositis, treatments to modify intestinal mucositis, and treatments for intestinal mucositis signs and symptoms include gastrointestinal cocktail (an acid reducer such aluminum hydroxide and magnesium hydroxide (e.g., Maalox), an antifungal (e.g., nystatin), and an analgesic (e.g., hurricane liquid)).

In certain embodiments, the second therapeutic agent or regimen is administered to the subject prior to contacting with or administering the chemical entity (e.g., about one hour prior, or about 6 hours prior, or about 12 hours prior, or about 24 hours prior, or about 48 hours prior, or about 1 week prior, or about 1 month prior).

In other embodiments, the second therapeutic agent or regimen is administered to the subject at about the same time as contacting with or administering the chemical entity. By way of example, the second therapeutic agent or regimen and the chemical entity are provided to the subject simultaneously in the same dosage form. As another example, the second therapeutic agent or regimen and the chemical entity are provided to the subject concurrently in separate dosage forms.

In still other embodiments, the second therapeutic agent or regimen is administered to the subject after contacting with or administering the chemical entity (e.g., about one hour after, or about 6 hours after, or about 12 hours after, or about 24 hours after, or about 48 hours after, or about 1 week after, or about 1 month after).

Patient Selection

In some embodiments, the methods described herein further include the step of identifying a subject (e.g., a patient) in need of such treatment (e.g., by way of biopsy, endoscopy, or other conventional method known in the art). In certain embodiments, the STING protein can serve as a biomarker for certain types of cancer, e.g., colon cancer and prostate cancer. In other embodiments, identifying a subject can include assaying the patient's tumor microenvironment for the absence of T-cells and/or presence of exhausted T-cells, e.g., patients having one or more cold tumors. Such patients can include those that are resistant to treatment with checkpoint inhibitors. In certain embodiments, such patients can be treated with a chemical entity herein, e.g., to recruit T-cells into the tumor, and in some cases, further treated with one or more checkpoint inhibitors, e.g., once the T-cells become exhausted.

In some embodiments, the chemical entities, methods, and compositions described herein can be administered to certain treatment-resistant patient populations (e.g., patients resistant to checkpoint inhibitors; e.g., patients having one or more cold tumors, e.g., tumors lacking T-cells or exhausted T-cells).

Compound Preparation

As can be appreciated by the skilled artisan, methods of synthesizing the compounds of the formulae herein will be evident to those of ordinary skill in the art. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and RGM. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof. The starting materials used in preparing the compounds of the invention are known, made by known methods, or are commercially available. The skilled artisan will also recognize that conditions and reagents described herein that can be interchanged with alternative art-recognized equivalents. For example, in many reactions, triethylamine can be interchanged with other bases, such as non-nucleophilic bases (e.g. diisopropylamine, 1,8-diazabicycloundec-7-ene, 2,6-di-tert-butylpyridine, or tetrabutylphosphazene).

The skilled artisan will recognize a variety of analytical methods that can be used to characterize the compounds described herein, including, for example, $^1$H NMR, heteronuclear NMR, mass spectrometry, liquid chromatography, and infrared spectroscopy. The foregoing list is a subset of characterization methods available to a skilled artisan and is not intended to be limiting.

To further illustrate the foregoing, the following non-limiting, exemplary synthetic schemes are included. Variations of these examples within the scope of the claims are within the purview of one skilled in the art and are considered to fall within the scope of the invention as described, and claimed herein. The reader will recognize that the skilled artisan, provided with the present disclosure, and skill in the art is able to prepare and use the invention without exhaustive examples.

Abbreviations

ACN=acetonitrile
AcOH=acetic acid
$Boc_2O$=di-tert-butyl pyrocarbornate
Bu=butyl
DBU=1,8-diazabicycloundec-7-ene
DCM=dichloromethane
DEAD=diethyl azodicarboxylate
DIEA=N,N-diisopropylethylamine
DMF=N,N-dimethylformamide
DMSO=dimethyl sulfoxide
DPPA=diphenyl azidophosphate
FA=formic acid
HATU=N-[(dimethylamino)-1H-1,2,3-triazolo-[4,5-b]pyridin-1-ylmethylene]-N-methylmethanaminium hexafluorophosphate N-oxide
HPLC=high-performance liquid chromatography
LCMS=liquid chromatography-mass spectrometry
Me=methyl
NMM=N-methylmorpholine
NMR=nuclear magnetic resonance
$Pd(dppf)Cl_2$=dichloro[1,1'-bis(diphenylphosphino)ferrocene]palladium
Ph=phenyl
Py=pyridine
TEA=triethylamine
Tf=trifluoromethanesulfonic
TFA=trifluoroacetic acid
TFAA=trifluoroacetic anhydride
THF=tetrahydrofuran
$T_3P$=2,4,6-tripropyl-2,4,6-trioxo-1,3,5,2,4,6-trioxatriphosphorinane
XPhos=(2-(2,4,6-triisopropylphenethyl)phenyl)dicyclohexylphosphine
PyBOP=Benzotriazol-1-yl-oxytripyrrolidinophosphonium hexafluorophosphate
DCM=Methylene chloride
XPhos Pd G3=Methanesulfonato(2-dicyclohexylphosphino2,4,6-tri-i-propyl-1,1-biphenyl)(2-amino-1,1-biphenyl-2-yl)palladium(II)
$K_3PO_4$=Potassium phosphate
$H_2O$=Water
MeOH=methanol
EtOAc=Ethyl acetate
SpeedVac=Savant SC250EXP SpeedVac Concentrator
CuI=Copper(I) iodide
L-proline=(2S)-pyrrolidine-2-carboxylic acid
$SnCl_2$=Tin(II) chloride
SPhos=2-dicyclohexylphosphino-2',6'-dimethoxy-1,1'-biphenyl
$Pd(CH_3CN)_2Cl_2$=Bis(acetonitrile)palladium(II) chloride
HBr=Hydrogen bromide
$Boc_2O$=Di-tert-butyldicarbonate
$K_2CO_3$=Potassium carbonate
$Cs_2CO_3$=Cesium carbonate
$Na_2CO_3$=Sodium carbonate
$Na_2SO_4$=Sodium sulfate
$AgNO_3$=Silver nitrate

EXAMPLES

Materials and Methods

The LC-MS was recorded using one of the following methods.

LCMS Method A: Kinetex EVO C18 100A, 30*3 mm, 0.5 μL injection, 1.2 mL/min flowrate, 90-900 amu scan range, 254 nm UV detection. Mobile Phase A (MPA): Water/5 mM NH4HCO3 and Mobile Phase B (MPB): Acetonitrile. Elution 10% MPB to 95% in 2.0 min, hold at 95% MPB for 0.3 min, 95% MPB to 10% in 0.1 min.

LCMS Method B: Xselect CSH C18, 50*3 mm, 1.0 μL injection, 1.2 mL/min flowrate, 90-900 amu scan range, 254 nm UV detection. Mobile Phase A (MPA): Water/0.1% FA and Mobile Phase B (MPB): Acetonitrile/0.1% FA. Elution 5% MPB to 100% in 2.00 min, hold at 100% MPB for 0.7 min, 100% MPB to 5% in 0.05 min, then equilibration to 5% MPB for 0.15 min.

LCMS Method C: XBridge Shield RP18, 50*4.6 mm, 0.5 μL injection, 1.2 mL/min flowrate, 90-900 amu scan range, 254 nm UV detection. Mobile Phase A (MPA): Water/0.04% NH4OH and Mobile Phase B (MPB): Acetonitrile. Elution 10% MPB to 95% in 2.00 min, hold at 95% MPB for 0.79 min, 95% MPB to 10% in 0.06 min, then equilibration to 10% MPB for 0.15 min.

LCMS Method D: Shim-pack XR-ODS, 50*3 mm, 0.3 μL injection, 1.2 mL/min flowrate, 30-2000 amu scan range, 254 nm UV detection. Mobile Phase A (MPA): Water/0.05 TFA and Mobile Phase B (MPB): Acetonitrile/0.05% TFA. Elution 5% MPB to 100% in 1.10 min, hold at 100% MPB for 0.60 min, 100% MPB to 5% in 0.05 min, then equilibration to 5% MPB for 0.25 min.

LCMS Method E: kinetex 2.6 um EVO, 50*3 mm, 0.5 μL injection, 1.2 mL/min flowrate, 30-2000 amu scan range, 254 nm UV detection. Mobile Phase A (MPA): Water/5 mM NH4HCO3 and Mobile Phase B (MPB): Acetonitrile. Elution 10% MPB to 95% in 2.00 min, hold at 95% MPB for 0.70 min, 95% MPB to 10% in 0.05 min, then equilibration to 5% MPB for 0.25 min.

LCMS Method F: Poroshell HPH C18, 50*3 mm, 0.5 μL injection, 1.2 mL/min flowrate, 30-2000 amu scan range, 254 nm UV detection. Mobile Phase A (MPA): Water/5 mM NH4HCO3+5 mM NH4OH and Mobile Phase B (MPB): Acetonitrile. Elution 10% MPB to 95% in 2.00 min, hold at 95% MPB for 0.70 min, 95% MPB to 5% in 0.05 min, then equilibration to 5% MPB for 0.25 min.

Method BA
   Instrument: Agilent LCMS system equipped with DAD and ELSD detector
   Ion mode: Positive
   Column: Waters X-Bridge C18, 50*2.1 mm*5 μm or equivalent
   Mobile Phase: A: $H_2O$ (0.04% TFA); B: $CH_3CN$ (0.02% TFA)
   Gradient: 4.5 min gradient method, actual method would depend on clogP of compound.
   Flow Rate: 0.6 mL/min or 0.8 mL/min
   Column Temp: 40° C. or 50° C.
   UV: 220 nm Method BB
   Instrument: Agilent LCMS system equipped with DAD and ELSD detector
   Ion mode: Positive Column: Waters X-Bridge ShieldRP18, 50*2.1 mm*5 μm or equivalent Mobile Phase: A: H₂O (0.05% NH3.H₂O) or 10 mM ammonia bicarbonate; B: CH₃CN Gradient: 4.5 min gradient method; actual method would depend on the clog P of the compound.

Flow Rate: 0.6 mL/min or 0.8 mL/min

Column Temp: 40° C.

UV: 220 nm

Prep. HPLC condition

Instrument:
1. GILSON 281 and Shimadzu LCMS 2010A
2. GILSON 215 and Shimadzu LC-20AP
3. GILSON 215

Mobile Phase:
A: NH4OH/H₂O=0.05% v/v; B: ACN
A: FA/H₂O=0.225% v/v; B: ACN

Column
Xtimate C18 150*25 mm*5 μm
Flow rate: 25 mL/min or 30 mL/min
Monitor wavelength: 220&254 nm
Gradient: actual method would depend on clog P of compound
Detector: MS Trigger or UV NMR was recorded on BRUKER NMR 300.03 Mz, DUL-C-H, ULTRASHIELD™ 300, AVANCE II 300 B-ACS™ 120 or BRUKER NMR 400.13 Mz, BBFO, ULTRASIELD™ 400, AVANCE III 400, B-ACS™ 120.

Preparative Examples

Synthesis of intermediate 1 (1-(4-ethylphenyl)-4-(4,4,5,5-tetramethyl-1,3,2-dioxaborolan-2-yl)-1H-pyrazole)

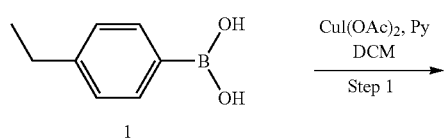

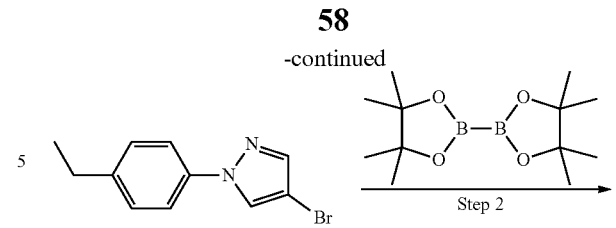

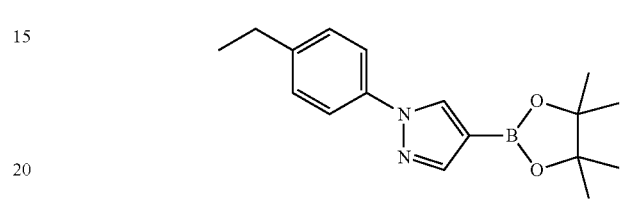

Intermediate 1

Step 1: 4-bromo-1-(4-ethylphenyl)-1H-pyrazole

4-Ethylphenylboronic acid (10.0 g, 66.7 mmol, 1.0 equiv.) and 4-bromopyrazole (9.8 g, 66.7 mmol, 1.0 equiv.) were dissolved in DCM (300 mL), then Cu(OAc)₂ (24.2 g, 133.4 mmol, 2.0 equiv.) and pyridine (2.1 mL, 26.7 mmol, 2.0 equiv.) were added under an atmosphere of nitrogen. The reaction mixture was stirred overnight at ambient temperature and concentrated under vacuum. The residue was purified by flash column chromatography on silica gel, eluting with ethyl acetate/petroleum ether (1:10) to give 4-bromo-1-(4-ethylphenyl)pyrazole (9.5 g) as a white solid. LCMS Method A: [M+H]⁺=251.

Step 2: 1-(4-ethylphenyl)-4-(4,4,5,5-tetramethyl-1,3,2-dioxaborolan-2-yl)-1H-pyrazole 4-Bromo-1-(4-ethylphenyl)pyrazole (9.5 g, 37.8 mmol, 1.0 equiv.) was dissolved in dioxane (200 mL), then bis(pinacolato)diboron (9.6 g, 37.8 mmol, 1.0 equiv.), KOAc (7.4 g, 75.7 mmol, 2.0 equiv.) and Pd(dppf)Cl₂ (5.5 g, 7.6 mmol, 0.2 equiv.) were added under an atmosphere of nitrogen. The reaction mixture was heated to 80° C. overnight, then cooled to ambient temperature and concentrated under vacuum. The residue was purified by flash column chromatography on silica gel, eluting with ethyl acetate/petroleum ether (1:4) to give 1-(4-ethylphenyl)-4-(4,4,5,5-tetramethyl-1,3,2-dioxaborolan-2-yl)-1H-pyrazole (4.0 g) as a yellow solid. LCMS Method C: [M+H]⁺=299.

The following intermediate was synthesized using methods described for Intermediate 1, above.

| Intermediate | Starting material | Structure | LCMS data |
| --- | --- | --- | --- |
| Intermediate 2 | ![OH-B(OH)-Ph-CF3] | ![pinacol boronate pyrazole CF3] | Method C: MS-ESI: 339 [M + H]⁺ |

Synthesis of intermediate 3 (2-(4-(4,4,5,5-tetramethyl-1,3,2-dioxaborolan-2-yl)-1H-pyrazol-1-yl)-5-(trifluoromethyl)pyridine)

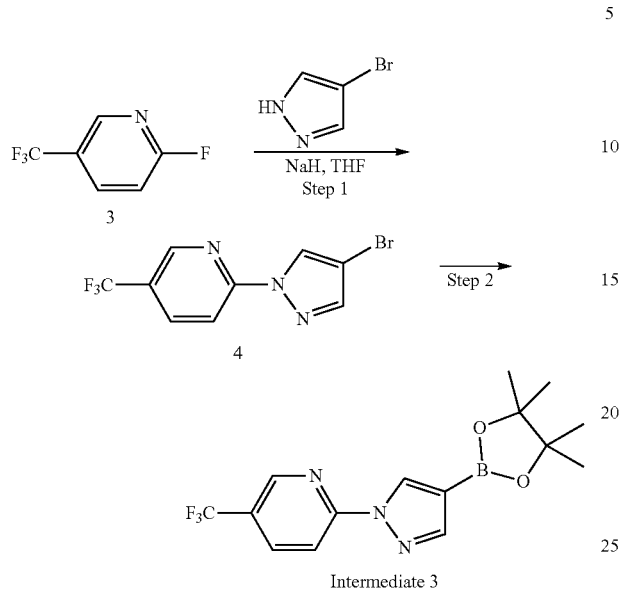

Intermediate 3

Step 1: 2-(4-bromopyrazol-1-yl)-5-(trifluoromethyl)pyridine

2-Fluoro-5-(trifluoromethyl)pyridine (5.0 g, 30.3 mmol, 1.0 equiv.) was dissolved in THF (80 mL) and cooled to 0° C., then NaH (60% wt., 2.4 g, 60.5 mmol, 2.0 equiv.) was added in portions, maintaining the solution at 0° C. After 5 min at 0° C., 4-bromopyrazole (4.9 g, 33.3 mmol, 1.1 equiv.) was added. The reaction mixture was heated to 80° C. for 4 hours, then cooled to ambient temperature and quenched by the addition of ice-water. The resulting solution was extracted with ethyl acetate and concentrated under vacuum. The residue was purified by flash column chromatography on silica gel, eluting with ethyl acetate/petroleum ether (1:4) to give 2-(4-bromopyrazol-1-yl)-5-(trifluoromethyl)pyridine (7.6 g) as a white solid. LCMS Method A: [M+H]$^+$=292.

Step 2: 2-[4-(4,4,5,5-tetramethyl-1,3,2-dioxaborolan-2-yl)pyrazol-1-yl]-5-(trifluoromethyl)pyridine 2-(4-Bromopyrazol-1-yl)-5-(trifluoromethyl)pyridine (6.2 g, 21.2 mmol, 1.0 equiv.) was dissolved in dioxane (100 mL), then KOAc (4.2 g, 42.3 mmol, 2.0 equiv.), bis(pinacolato)diboron (10.8 g, 42.5 mmol, 2.0 equiv.) and Pd(dppf)Cl$_2$ CH$_2$C2 (1.7 g, 2.1 mmol, 0.1 equiv.) were added under an atmosphere of nitrogen. The reaction mixture was heated to 90° C. for 4 hours, then cooled to ambient temperature and concentrated under vacuum. The residue was purified by flash column chromatography on silica gel, eluting with ethyl acetate/petroleum ether (1:5) to give 2-[4-(4,4,5,5-tetramethyl-1,3,2-dioxaborolan-2-yl)pyrazol-1-yl]-5-(trifluoromethyl)pyridine (6.5 g) as a white solid. LCMS Method C: [M+H]$^+$=340.

Synthesis of intermediate 4 (4-(4,4,5,5-tetramethyl-1,3,2-dioxaborolan-2-yl)-1-(4-(trifluoromethyl)benzyl)-1H-pyrazole)

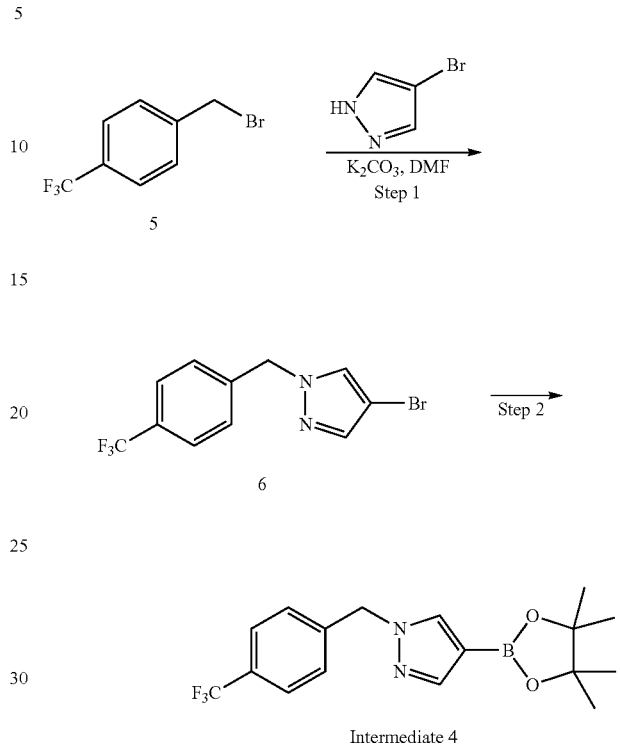

Intermediate 4

Step 1: 4-bromo-1-[[4-(trifluoromethyl)phenyl]methyl]pyrazole 1-(Bromomethyl)-4-(trifluoromethyl)benzene (1.5 g, 6.3 mmol, 1.0 equiv.) was dissolved in DMF (15 mL), then 4-bromopyrazole (1.0 g, 6.8 mmol, 1.1 equiv.) and K$_2$CO$_3$ (1.7 g, 12.6 mmol, 2.0 equiv.) were added. The reaction mixture was heated to 80° C. overnight, then cooed to ambient temperature and concentrated under vacuum. The residue was purified by flash column chromatography on silica gel, eluting with ethyl acetate/petroleum ether (1:25) to give crude 4-bromo-1-[[4-(trifluoromethyl)phenyl]methyl]pyrazole (1.8 g) as a colorless oil. LCMS Method A: [M+H]$^+$=305.

Step 2: 4-(4,4,5,5-tetramethyl-1,3,2-dioxaborolan-2-yl)-1-[[4-(trifluoromethyl)phenyl]methyl]pyrazole 4-Bromo-1-[[4-(trifluoromethyl)phenyl]methyl]pyrazole (1.5 g, 4.9 mmol, 1.0 equiv.) was dissolved in 1,4-dioxane (50 mL), then KOAc (1.3 g, 12.8 mmol, 2.6 equiv.), bis(pinacolato)diboron (3.2 g, 12.4 mmol, 2.5 equiv.) and Pd(dppf)Cl$_2$ CH$_2$C2 (0.5 g, 0.6 mmol, 0.1 equiv.) were added under an atmosphere of nitrogen. The reaction mixture was heated to 90° C. for 4 hours, then cooled to ambient temperature and concentrated under vacuum. The residue was purified by flash column chromatography on silica gel, eluting with ethyl acetate/petroleum ether (1:2) to give 4-(4,4,5,5-tetramethyl-1,3,2-dioxaborolan-2-yl)-1-[[4-(trifluoromethyl)phenyl]methyl]pyrazole (1.2 g) as a yellow solid. LCMS Method A: [M+H]$^+$=353.

Synthesis of intermediate 5 (1-(5-bromo-1H-indol-3-yl)-3-methylurea)

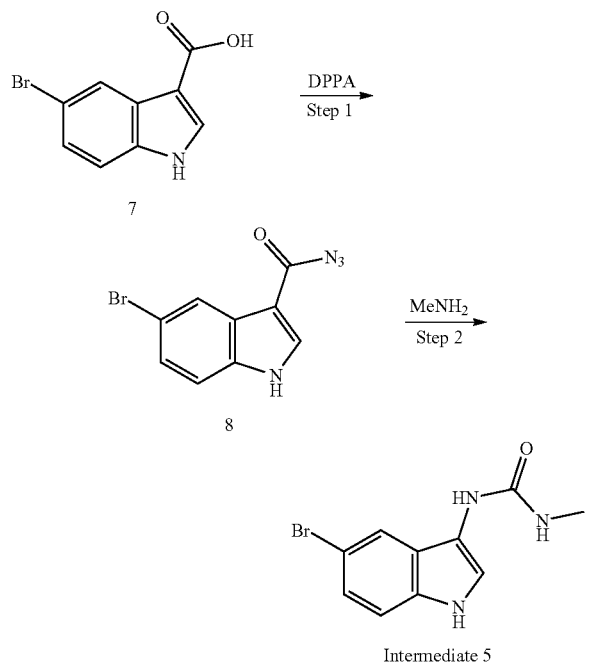

Step 1: 5-bromo-1H-indole-3-carbonyl azide

5-Bromo-1H-indole-3-carboxylic acid (1.0 g, 4.2 mmol, 1.0 equiv.) and DPPA (2.3 g, 8.3 mmol, 2.0 equiv.) were dissolved in THF (5 mL), then TEA (1.1 mL, 8.3 mmol, 2.0 equiv.) was added dropwise. The reaction mixture was stirred overnight at ambient temperature and concentrated under vacuum. The residue was purified by flash column chromatography on silica gel, eluting with ethyl acetate/petroleum ether (1/2) to afford 5-bromo-1H-indole-3-carbonyl azide (1.0 g) as a white solid. LCMS Method A: $[M+H]^+=265$.

Step 2: 1-(5-bromo-1H-indol-3-yl)-3-methylurea

5-Bromo-1H-indole-3-carbonyl azide (851.0 mg, 3.2 mmol, 1.0 equiv.) was dissolved in toluene (10 mL). The resulting solution was heated to 90° C. for 2 hours under an atmosphere of nitrogen. After cooling to ambient temperature, MeNH$_2$ in THF (2M, 5 mL, 10.0 mmol, 3.0 equiv.) was added to the above solution. The reaction mixture was stirred for an additional 2 hours at ambient temperature, then concentrated under vacuum. The residue was purified by flash column chromatography on silica gel, eluting with ethyl acetate/petroleum ether (10/1) to afford 1-(5-bromo-1H-indol-3-yl)-3-methylurea (800 mg, 92.90%) as a pink solid. LCMS Method B: $[M-H]^-=266$.

The following intermediates were synthesized using methods described for Intermediate 5, above.

| Intermediate | Starting material | Structure | LCMS data |
| --- | --- | --- | --- |
| Intermediate 6 | cyclopropylmethylamine | (5-bromoindol-3-yl)-N'-(cyclopropylmethyl)urea | Method A: MS-ESI: 308 $[M + H]^+$ |
| Intermediate 7 | H$_2$N-CH$_2$-CF$_3$ · HCl | (5-bromoindol-3-yl)-N'-(2,2,2-trifluoroethyl)urea | Method A: MS-ESI: 336 $[M + H]^+$ |
| Intermediate 8 | H$_2$N-CH$_2$-C(CH$_3$)$_2$-OH | (5-bromoindol-3-yl)-N'-(2-hydroxy-2-methylpropyl)urea | Method C: MS-ESI: 326 $[M + H]^+$ |

| Intermediate | Starting material | Structure | LCMS data |
|---|---|---|---|
| Intermediate 9 | 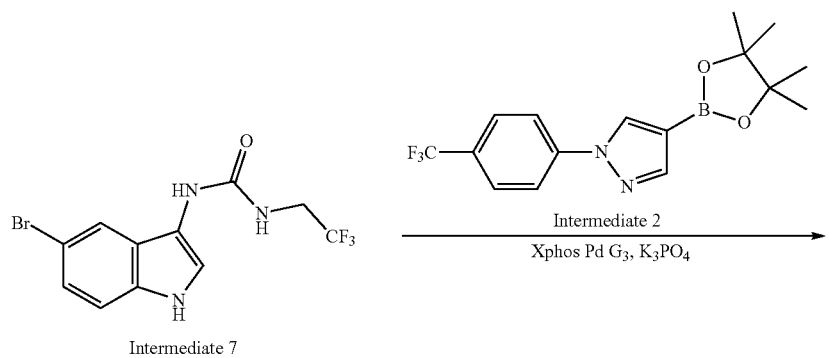 | 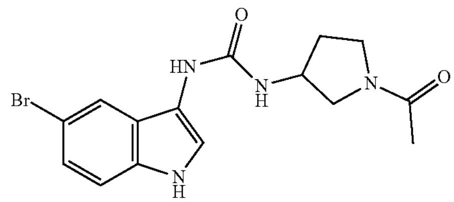 [SMILES: CC(=O)N1CCC(NC(=O)Nc2c[nH]c3ccc(Br)cc23)C1] | Method A: MS-ESI: 365 [M + H]+ |

Example 1: 1-(2,2,2-trifluoroethyl)-3-(5-(1-(4-(trifluoromethyl)phenyl)-1H-pyrazol-4-yl)-1H-indol-3-yl)urea (Compound 104)

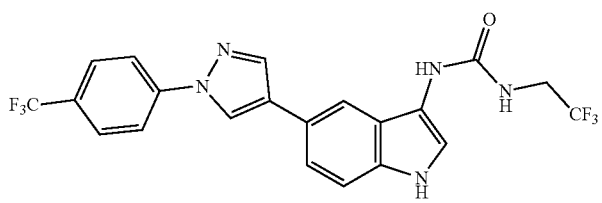

Compound 104

1-(5-Bromo-1H-indol-3-yl)-3-(2,2,2-trifluoroethyl)urea (260.0 mg, 0.8 mmol, 1.0 equiv.) and 4-(4,4,5,5-tetramethyl-1,3,2-dioxaborolan-2-yl)-1-(4-(trifluoromethyl)phenyl)-1H-pyrazole (313.9 mg, 0.9 mmol, 1.2 equiv.) were dissolved in dioxane (5 mL)/water (0.5 mL), then Xphos Pd G3 (131.0 mg, 0.2 mmol, 0.2 equiv.) and $K_3PO_4$ (492.6 mg, 2.3 mmol, 3.0 equiv.) were added under an atmosphere of nitrogen. The reaction mixture was heated to 100° C. for 2 hours, then cooled to ambient temperature and quenched by the addition of water. The resulting mixture was extracted with ethyl acetate, dried over anhydrous sodium sulfate and concentrated under vacuum. The residue was purified by flash column chromatography on silica gel, eluting with ethyl acetate/petroleum ether (1:1) to give the crude product, that was purified by Prep-HPLC with the following conditions: Column: XBridge Prep OBD C18 Column, 30×150 mm 5 µm; Mobile Phase A: Water (10 mmol/L NH4HCO3), Mobile Phase B: ACN; Flow rate: 60 mL/min; 220 nm; RT1:7.23. This resulted in 1-(2,2,2-trifluoroethyl)-3-(5-(1-(4-(trifluoromethyl)phenyl)-1H-pyrazol-4-yl)-1H-indol-3-yl)urea as a white solid. LCMS Method E: [M+H]+=468. $^1$H NMR (400 MHz, DMSO-d6) δ 10.81 (s, 1H), 9.04 (s, 1H), 8.47 (br s, 1H), 8.20 (s, 1H), 8.15 (d, J=8.4 Hz, 2H), 7.91 (d, J=8.4 Hz, 2H), 7.79 (s, 1H), 7.49-7.47 (m, 1H), 7.43-7.37 (m, 2H), 6.65-6.63 (m, 1H), 3.97-3.93 (m, 2H).

The following compounds were synthesized using methods described for Example 1, above.

| Example | Compound # | Starting material | Structure | LCMS data |
|---|---|---|---|---|
| 2 | 109 | Intermediate 6<br>Intermediate 2 | 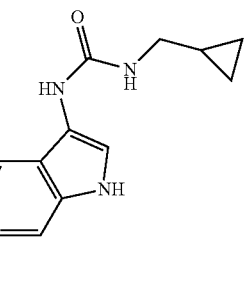<br>1-(cyclopropylmethyl)-3-(5-(1-(4-(trifluoromethyl)phenyl)-1H-pyrazol-4-yl)-1H-indol-3-yl)urea | Method F: MS-ESI: 440 [M + H]⁺. |
| 3 | 107 | Intermediate 7<br>Intermediate 3 | 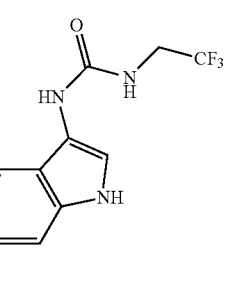<br>1-(2,2,2-trifluoroethyl)-3-(5-(1-(5-(trifluoromethyl)pyridin-2-yl)-1H-pyrazol-4-yl)-1H-indol-3-yl)urea | Method E: MS-ESI: 469 [M + H]⁺. |
| 4 | 106 | Intermediate 6<br>Intermediate 3 | 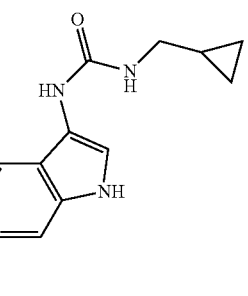<br>1-(cyclopropylmethyl)-3-(5-(1-(5-(trifluoromethyl)pyridin-2-yl)-1H-pyrazol-4-yl)-1H-indol-3-yl)urea | Method E: MS-ESI: 441 [M + H]⁺. |
| 5 | 105 | Intermediate 5<br>Intermediate 4 | 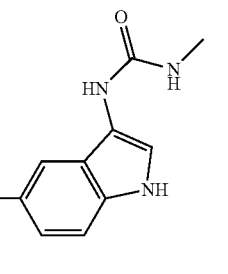<br>1-methyl-3-(5-(1-(4-(trifluoromethyl)benzyl)-1H-pyrazol-4-yl)-1H-indol-3-yl)urea | Method E: MS-ESI: 414 [M + H]⁺. |

-continued

| Example | Compound # | Starting material | Structure | LCMS data |
|---|---|---|---|---|
| 6 | 103 | Intermediate 6<br>Intermediate 4 | 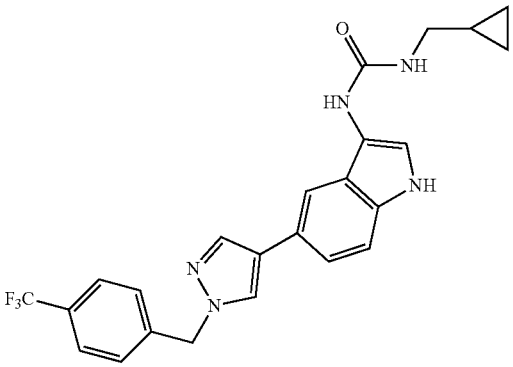 [SMILES: O=C(NCC1CC1)Nc1c[nH]c2ccc(-c3cnn(Cc4ccc(C(F)(F)F)cc4)c3)cc12]<br>1-(cyclopropylmethyl)-3-(5-(1-<br>(4-(trifluoromethyl)benzyl)-1H-<br>pyrazol-4-yl)-1H-indol-3-yl)urea | Method E: MS-ESI: 454 $[M + H]^+$. |
| 7 | 102 | Intermediate 8<br>Intermediate 2 | 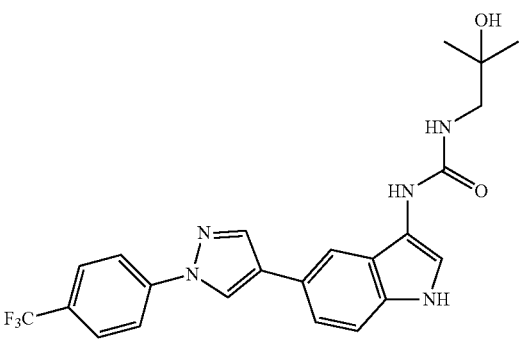 [SMILES: CC(C)(O)CNC(=O)Nc1c[nH]c2ccc(-c3cnn(-c4ccc(C(F)(F)F)cc4)c3)cc12]<br>1-(2-hydroxy-2-methylpropyl)-<br>3-(5-(1-(4-(trifluoromethyl)phenyl)-1H-<br>pyrazol-4-yl)-1H-indol-3-yl)urea | Method E: MS-ESI: 458 $[M + H]^+$. |
| 8 | 101 | Intermediate 9<br>Intermediate 2 | 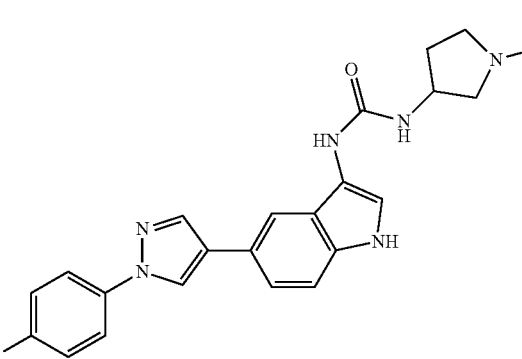<br>1-(1-acetylpyrrolidin-3-yl)-3-<br>(5-(1-(4-(trifluoromethyl)phenyl)-1H-<br>pyrazol-4-yl)-1H-indol-3-yl)urea | Method E: MS-ESI: 497 $[M + H]^+$. |

Example 9: 1-(5-(1-(4-ethylphenyl)-1H-pyrazol-4-yl)-1H-indol-3-yl)-3-methylurea

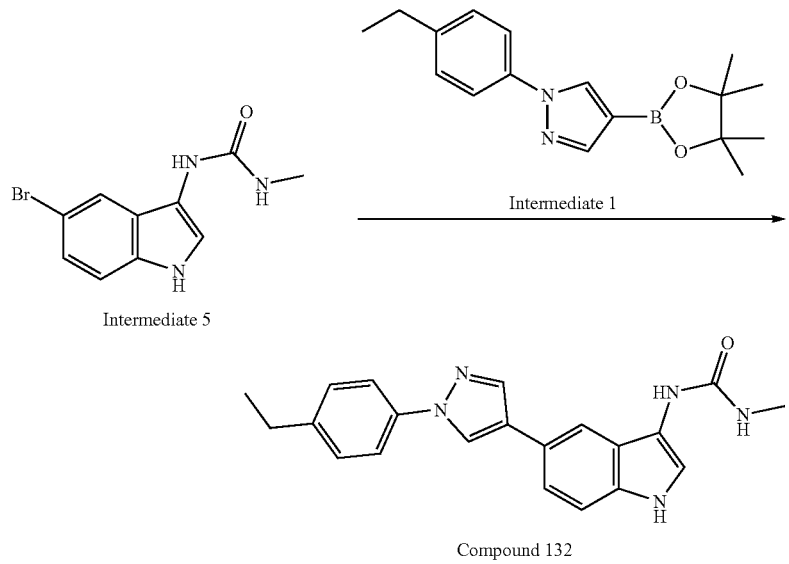

Intermediate 5

Compound 132

1-(5-Bromo-1H-indol-3-yl)-3-methylurea (186.0 mg, 0.7 mmol, 1.0 equiv.) was dissolved in dioxane (15 mL) and water (1.5 mL), then $Cs_2CO_3$ (678.1 mg, 2.1 mmol, 3.0 equiv.), 1-(4-ethylphenyl) pyrazol-4-ylboronic acid (300.0 mg, 1.4 mmol, 2.0 equiv.) and $Pd(dppf)Cl_2$ (50.8 mg, 0.07 mmol, 0.1 equiv.) were added under an atmosphere of nitrogen. The reaction mixture was heated to 90° C. for 2 hours, then cooled to ambient temperature and concentrated under vacuum. The residue was purified by flash column chromatography on silica gel, eluting with dichloromethane/methanol (10/1) to give material that was further purified by Prep-HPLC with the following condition: Column: YMC-Actus Triart C18, 30*250 mm, 5 μm; Mobile Phase A: Water (10 mM $NH_4HCO_3$+0.1% $NH_3.H_2O$), Mobile Phase B: ACN; Flow rate: 60 mL/min; Gradient: 40 B to 70 B in 7 min; 254/210 nm; RT1: 6.42. This resulted in 1-[5-[1-(4-ethylphenyl) pyrazol-4-yl]-1H-indol-3-yl]-3-methylurea as a white solid. LCMS Method D: 360 [M+H]⁺. ¹HNMR (400 MHz, DMSO-$d_6$) δ 10.69 (s, 1H), 8.80 (s, 1H), 8.10 (s, 1H), 8.06 (s, 1H), 7.83-7.81 (m, 2H), 7.76 (s, 1H), 7.45-7.33 (m, 5H), 5.89-5.86 (m, 1H), 2.69-2.64 (m, 5H), 1.23 (t, J=7.6 Hz, 3H).

Example 10: Synthesis of 1-methyl-3-(5-(1-(4-(trifluoromethyl)phenyl)-1H-pyrazol-4-yl)-1H-indol-3-yl)urea (Compound 118)

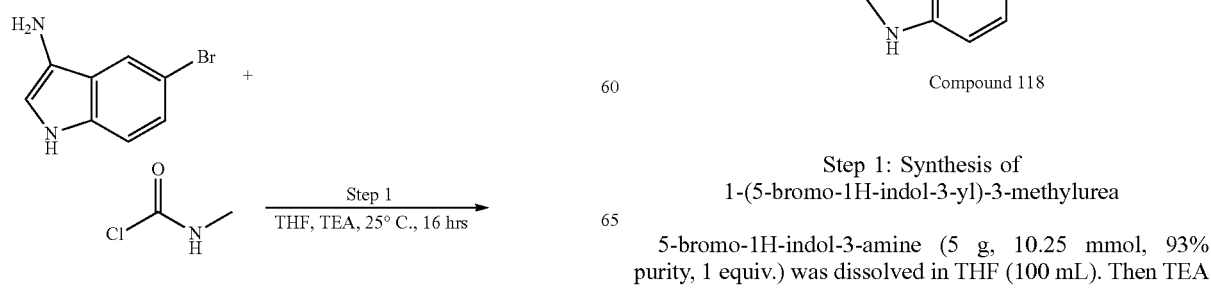

Compound 118

Step 1: Synthesis of 1-(5-bromo-1H-indol-3-yl)-3-methylurea 5-bromo-1H-indol-3-amine (5 g, 10.25 mmol, 93% purity, 1 equiv.) was dissolved in THF (100 mL). Then TEA (9.60 g, 94.9 mmol, 13.2 mL, 9.26 equiv.) and N-methylcarbamoyl chloride (1.82 g, 19.5 mmol, 2.34 mL, 1.9 equiv.) was added. The mixture was stirred at ambient temperature for 16 hours. The solids were removed by filtration, and the filtrate was concentrated under vacuum. Then 20 mL of DCM was added to the residue to give a slurry, which was stirred at ambient temperature for 10 minutes and filtered to give 1-(5-bromo-1H-indol-3-yl)-3-methylurea which was used directly without additional purification.

Step 2: Synthesis of 1-methyl-3-(5-(1-(4-(trifluoromethyl)phenyl)-1H-pyrazol-4-yl)-1H-indol-3-yl)urea 1-(5-bromo-1H-indol-3-yl)-3-methylurea (67.0 mg, 0.25 mmol, 1.0 equiv.) and (1-(4-(trifluoromethyl)phenyl)-1H-pyrazol-4-yl)boronic acid (97.3 mg, 0.38 mmol, 1.5 equiv.) were dissolved in 1,4-Dioxane (3.0 mL). Then 2 M aqueous $K_3PO_4$ (0.25 mL, 0.50 mmol, 2.0 equiv.) and XPhos Pd G3 (10.2 mg, 0.012 mmol, 0.05 equiv.) were added under an atmosphere of nitrogen. The mixture was shaken at 120° C. for 16 hours. The mixture was cooled to ambient temperature, $H_2O$ (3 mL) was added to the reaction mixture and then washed with EtOAc. The combined organic layers were concentrated by SpeedVac. The residue was purified by prep HPLC to give 1-methyl-3-(5-(1-(4-(trifluoromethyl)phenyl)-1H-pyrazol-4-yl)-1H-indol-3-yl)urea. MS-ESI, 400.2 [M+H$^+$].

$^1$H NMR (400 MHz, DMSO-d6) δ ppm 10.73 (s, 1H), 9.03 (s, 1H), 8.20 (s, 1H), 8.15 (d, J=8.5 Hz, 2H), 8.09 (s, 1H), 7.90 (d, J=8.8 Hz, 2H), 7.79 (s, 1H), 7.48-7.43 (m, 1H), 7.40-7.33 (m, 2H), 5.87 (br d, J=4.8 Hz, 1H), 2.66 (d, J=4.5 Hz, 3H).

The following compounds were synthesized using the methods described for Example 1, above.

| Example # | Compound # | Structure | Name | LC-MS, MS-ESI, — [M + H]$^+$. (Methods BA or BB) |
|---|---|---|---|---|
| 11 | 131 | 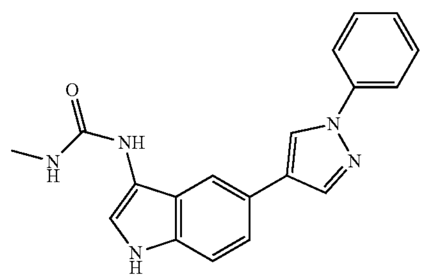 [SMILES: CNC(=O)Nc1c[nH]c2ccc(-c3cnn(-c4ccccc4)c3)cc12] | 3-methyl-1-[5-(1-phenyl-1H-pyrazol-4-yl)-1H-indol-3-yl]urea | 332.2 |
| 12 | 115 | 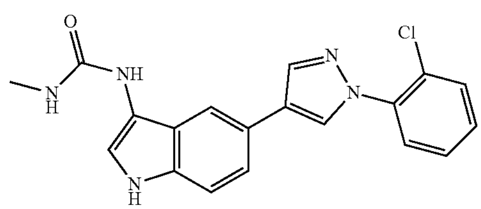 [SMILES: CNC(=O)Nc1c[nH]c2ccc(-c3cnn(-c4ccccc4Cl)c3)cc12] | 1-{5-[1-(2-chlorophenyl)-1H-pyrazol-4-yl]-1H-indol-3-yl}-3-methylurea | 366.1 |
| 13 | 113 | 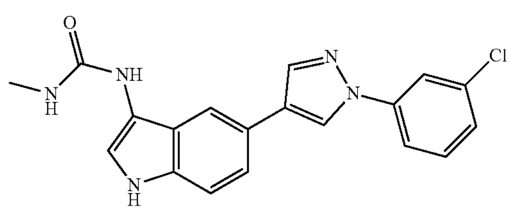 [SMILES: CNC(=O)Nc1c[nH]c2ccc(-c3cnn(-c4cccc(Cl)c4)c3)cc12] | 1-{5-[1-(3-chlorophenyl)-1H-pyrazol-4-yl]-1H-indol-3-yl}-3-methylurea | 366.1 |
| 14 | 116 | 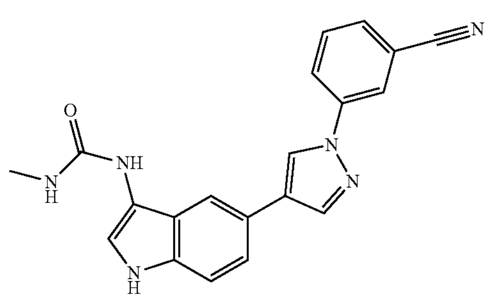 [SMILES: CNC(=O)Nc1c[nH]c2ccc(-c3cnn(-c4cccc(C#N)c4)c3)cc12] | 1-{5-[1-(3-cyanophenyl)-1H-pyrazol-4-yl]-1H-indol-3-yl}-3-methylurea | 357.2 |

| Example # | Compound # | Structure | Name | LC-MS, MS-ESI, — [M + H]+. (Methods BA or BB) |
|---|---|---|---|---|
| 15 | 123 | 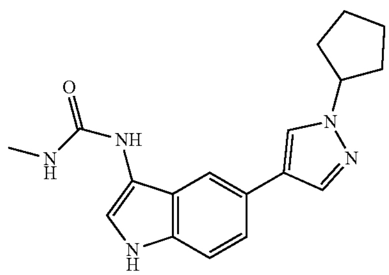 [SMILES: CNC(=O)Nc1c[nH]c2ccc(-c3cnn(C4CCCC4)c3)cc12] | 1-[5-(1-cyclopentyl-1H-pyrazol-4-yl)-1H-indol-3-yl]-3-methylurea | 324.3 |
| 16 | 122 | 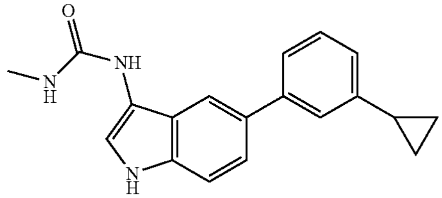 [SMILES: CNC(=O)Nc1c[nH]c2ccc(-c3cccc(C4CC4)c3)cc12] | 1-[5-(3-cyclopropylphenyl)-1H-indol-3-yl]-3-methylurea | 306.2 |
| 17 | 121 | 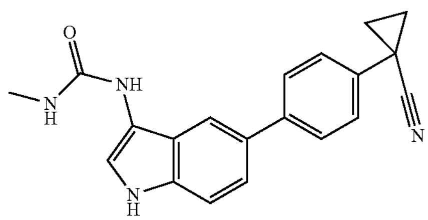 [SMILES: CNC(=O)Nc1c[nH]c2ccc(-c3ccc(C4(C#N)CC4)cc3)cc12] | 1-{5-[4-(1-cyanocyclopropyl)phenyl]-1H-indol-3-yl}-3-methylurea | 331.2 |
| 18 | 117 | 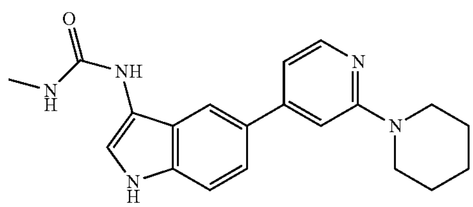 [SMILES: CNC(=O)Nc1c[nH]c2ccc(-c3ccnc(N4CCCCC4)c3)cc12] | 3-methyl-1-{5-[2-(piperidin-1-yl)pyridin-4-yl]-1H-indol-3-yl}urea | 350.3 |
Example 19: Synthesis of 1-(5-(1-(4-ethylphenyl)-1H-pyrazol-4-yl)-1H-indol-3-yl)-3-(3,3,3-trifluoropropyl)urea (Compound 114)
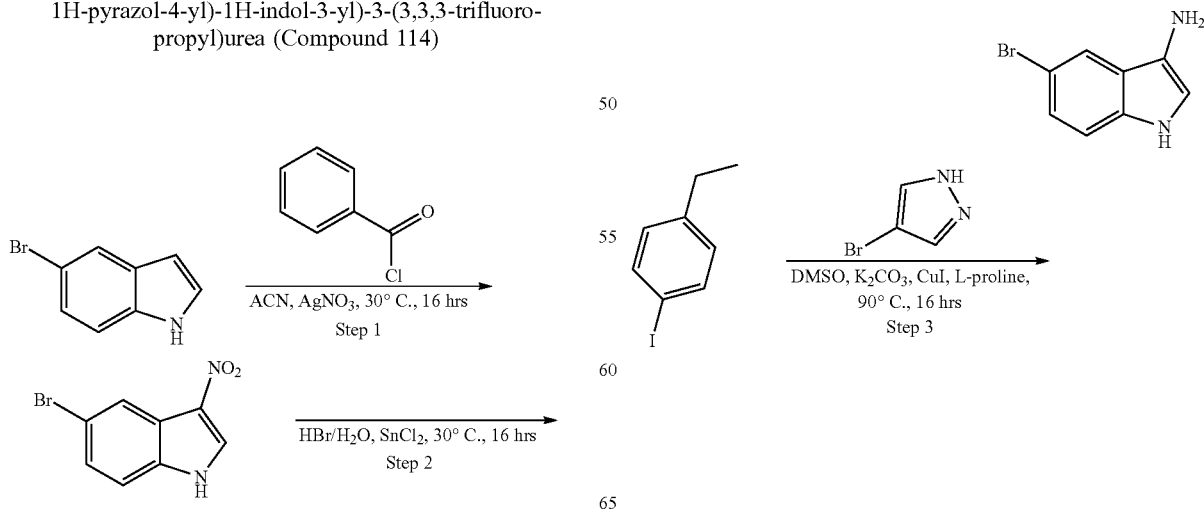

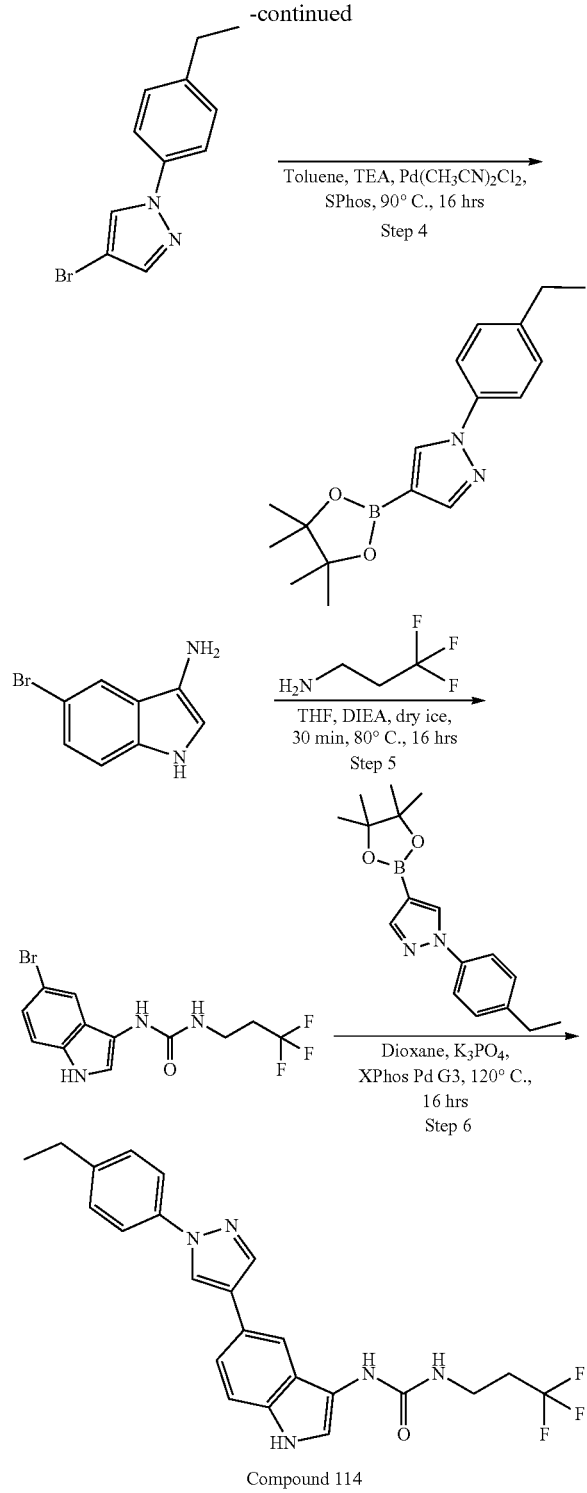

Compound 114

Step 1: Synthesis of 5-bromo-3-nitro-1H-indole 5-bromo-1H-indole (19.5 g, 99.5 mmol, 1.0 equiv.) was dissolved in ACN (200 mL) and cooled to 0° C. Then AgNO₃ (18.59 g, 109.4 mmol, 1.1 equiv.) was added portion wise over 3 minutes, maintaining the temperature at 0° C. After addition was compete, the mixture was stirred at 0° C. for 5 minutes, then benzoyl chloride (15.38 g, 109.4 mmol, 12.71 mL, 1.1 equiv.) was added dropwise, maintaining the temperature at 0° C. The resulting mixture was stirred at 30° C. for 16 hours. The reaction mixture was adjusted to pH 8 by the dropwise addition of 1 M aqueous Na₂CO₃ solution, then the mixture was extracted with EtOAc (150 mL). The combined organic layers were washed with 1 M aqueous Na₂CO₃ solution (300 mL), dried over anhydrous Na₂SO₄, filtered and concentrated under reduced pressure to give 5-bromo-3-nitro-1H-indole (21 g, 87.14 mmol) which was used in the next step without further purification.

Step 2: Synthesis of 5-bromo-1H-indol-3-amine 5-bromo-3-nitro-1H-indole (20.0 g, 83.0 mmol, 1 equiv.) was dissolved in HBr/H₂O (200 mL, 40% HBr in water), then SnCl₂ (78.82 g, 414.9 mmol, 5 equiv.) was added. The mixture was stirred at 30° C. for 16 hours. The reaction mixture was filtered and concentrated under reduced pressure to give 5-bromo-1H-indol-3-amine (13 g, 61.59 mmol), which was used in the next step without further purification.

Step 3: Synthesis of 4-bromo-1-(4-ethylphenyl)pyrazole 1-ethyl-4-iodo-benzene (25.0 g, 107.7 mmol, 1.0 equiv.) and 4-bromo-1H-pyrazole (31.67 g, 215.5 mmol, 2.0 equiv.) were dissolved in DMSO (500 mL). Then K₂CO₃ (29.78 g, 215.5 mmol, 2.0 equiv.), (2S)-pyrrolidine-2-carboxylic acid (2.48 g, 21.6 mmol, 0.2 equiv.) and CuI (2.05 g, 10.8 mmol, 0.1 equiv.) were added under an atmosphere of nitrogen. The mixture was heated at 90° C. for 16 hours under an atmosphere of nitrogen. The mixture was poured into 500 mL of H₂O, then extracted with 800 mL of ethyl acetate. The solids were removed by filtration, then the aqueous phase was extracted with ethyl acetate. The combined organics were dried over anhydrous Na₂SO₄, filtered and concentrated under vacuum. The residue was purified by flash column chromatography on silica gel (Petroleum ether/Ethyl acetate=0 to 6%) to give 4-bromo-1-(4-ethylphenyl) pyrazole (18.5 g, 73.7 mmol) as a white solid. MS-ESI, 250.9, 252.9 [M+H⁺].

Step 4: Synthesis of 1-(4-ethylphenyl)-4-(4,4,5,5-tetramethyl-1,3,2-dioxaborolan-2-yl)pyrazole 4-bromo-1-(4-ethylphenyl)pyrazole (18.5 g, 73.7 mmol, 1 equiv.) and 4,4,5,5-tetramethyl-1,3,2-dioxaborolane (89.57 g, 699.86 mmol, 101.55 mL, 9.5 equiv.) were dissolved in toluene (500 mL), then TEA (175.0 mmol, 24.35 mL, 2.4 equiv.), Pd(CH₃CN)₂Cl₂ (907.8 mg, 3.50 mmol, 0.05 equiv.) and SPhos (4.31 g, 10.5 mmol, 0.14 equiv.) were added under an atmosphere of nitrogen. The mixture was heated at 90° C. for 16 hours. The solution was poured into 500 mL of H₂O. The aqueous layer was extracted with ethyl acetate, then the organic layer was dried over anhydrous Na₂SO₄, filtrated, and concentrated under vacuum. The residue was purified by flash column chromatography on silica gel, (Petroleum ether/Ethyl acetate=0% to 6%) to give 1-(4-ethylphenyl)-4-(4,4,5,5-tetramethyl-1,3,2-dioxaborolan-2-yl)pyrazole (16.16 g, 54.22 mmol) as a yellow solid. MS-ESI, 299.1 [M+H⁺].

Step 5: Synthesis of 1-(5-bromo-1H-indol-3-yl)-3-(3,3,3-trifluoropropyl)urea 4-nitrophenyl chloroformate (66.3 mg, 0.33 mmol, 1.1 equiv.) was dissolved in THF (3.0 mL) and cooled to −30°

C. Then a solution of 5-bromo-1H-indol-3-amine (64 mg, 0.30 mmol, 1.0 equiv.) and N,N-diisopropylethylamine (198 µl, 1.20 mmol, 4.0 equiv.) dissolved in THF (2 mL) was added dropwise over 0.5 minute, maintaining the temperature at −30° C. The mixture was stirred at −30° C. for 30 minutes. Then a solution of propan-2-amine (53 mg, 0.90 mmol, 3.0 equiv.) dissolved in THF (1 mL) was added dropwise over 0.5 minute, maintaining the temperature at −30° C. The reaction mixture was warmed to ambient temperature and then heated at 80° C. for 16 hours. The reaction mixture was concentrated by SpeedVac to give a residue which was used in next step without further purification.

Step 6: Synthesis of 1-(5-(1-(4-ethylphenyl)-1H-pyrazol-4-yl)-1H-indol-3-yl)-3-(3,3,3-trifluoropropyl)urea 1-(5-bromo-1H-indol-3-yl)-3-(3,3,3-trifluoropropyl)urea (105 mg, 0.3 mmol, 1.0 equiv.) and 1-(4-ethylphenyl)-4-(4,4,5,5-tetramethyl-1,3,2-dioxaborolan-2-yl)-1H-pyrazole (116 mg, 0.39 mmol, 1.3 equiv.) were dissolved in 1,4-Dioxane (3.0 mL). Then XPhos Pd G3 (12.7 mg, 0.015 mmol, 0.05 equiv.) and 0.45 mL of aqueous $K_3PO_4$ (2 M, 0.90 mmol, 3.0 equiv.) was added under an atmosphere of nitrogen. The mixture was heated at 120° C. for 16 hours. Then the reaction mixture was cooled to ambient temperature, poured into 6 mL of $H_2O$, and then extracted with EtOAc. The combined organic layers were concentrated by SpeedVac and the residue purified by prep HPLC to give 1-(5-(1-(4-ethylphenyl)-1H-pyrazol-4-yl)-1H-indol-3-yl)-3-(3,3,3-trifluoropropyl)urea. MS-ESI, 441.2 [M+H⁺].

$^1$H NMR (400 MHz, DMSO-d6) δ ppm 10.71 (br s, 1H), 8.80 (s, 1H), 8.28 (br s, 1H), 8.06 (s, 1H), 7.81 (d, J=8.5 Hz, 2H), 7.75 (s, 1H), 7.47-7.29 (m, 5H), 6.19 (t, J=5.9 Hz, 1H), 3.41-3.35 (m, 2H), 2.66 (q, J=7.5 Hz, 2H), 2.48-2.39 (m, 2H), 1.22 (t, J=7.5 Hz, 3H).

The following compounds were synthesized using methods described for Example 19, above.

| Example # | Compound # | Structure | IUPAC Name | LC-MS, MS-ESI, — [M + H]⁺. Methods BA or BB |
|---|---|---|---|---|
| 20 | 130 | 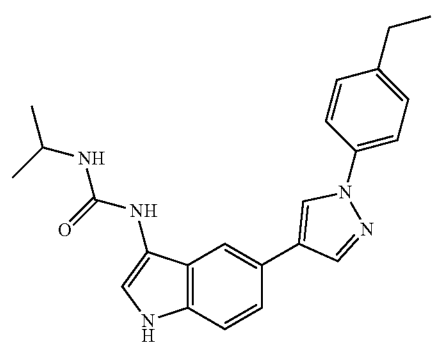 [SMILES: CCc1ccc(-n2cc(-c3ccc4[nH]cc(NC(=O)NC(C)C)c4c3)cn2)cc1] | 1-(5-(1-(4-ethylphenyl)-1H-pyrazol-4-yl)-1H-indol-3-yl)-3-isopropylurea | 388.2 |
| 21 | 129 | 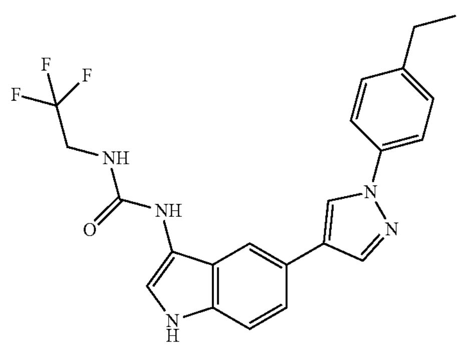 [SMILES: CCc1ccc(-n2cc(-c3ccc4[nH]cc(NC(=O)NCC(F)(F)F)c4c3)cn2)cc1] | 1-{5-[1-(4-ethylphenyl)-1H-pyrazol-4-yl}-1H-indol-3-yl}-3-(2,2,2-trifluoroethyl)urea | 428.2 |
| 22 | 127 | 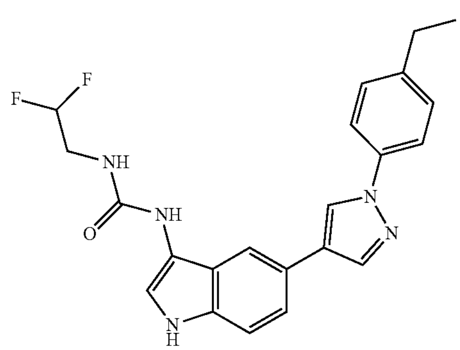 [SMILES: CCc1ccc(-n2cc(-c3ccc4[nH]cc(NC(=O)NCC(F)F)c4c3)cn2)cc1] | 1-(2,2-difluoroethyl)-3-(5-(1-(4-ethylphenyl)-1H-pyrazol-4-yl)-1H-indol-3-yl)urea | 410.2 |

-continued

| Example # | Compound # | Structure | IUPAC Name | LC-MS, MS-ESI, [M + H]+. Methods BA or BB |
|---|---|---|---|---|
| 23 | 126 | 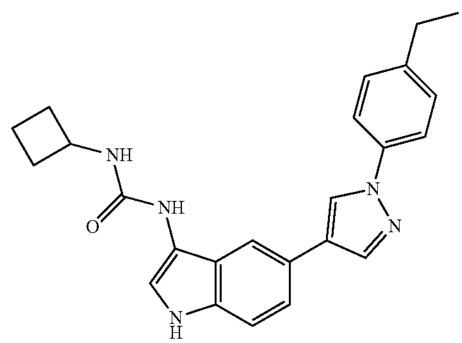 [SMILES: CCc1ccc(-n2cc(-c3ccc4[nH]cc(NC(=O)NC5CCC5)c4c3)cn2)cc1] | 1-cyclobutyl-3-(5-(1-(4-ethylphenyl)-1H-pyrazol-4-yl)-1H-indol-3-yl)urea | 400.2 |
| 24 | 120 | 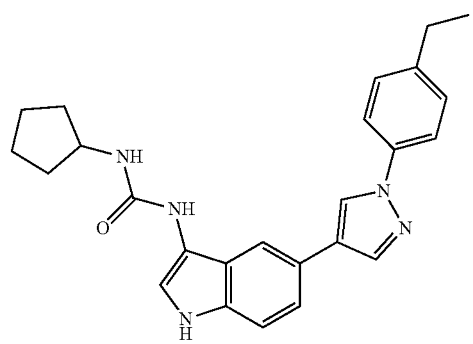 [SMILES: CCc1ccc(-n2cc(-c3ccc4[nH]cc(NC(=O)NC5CCCC5)c4c3)cn2)cc1] | 1-cyclopentyl-3-(5-(1-(4-ethylphenyl)-1H-pyrazol-4-yl)-1H-indol-3-yl)urea | 414.3 |
| 25 | 125 | 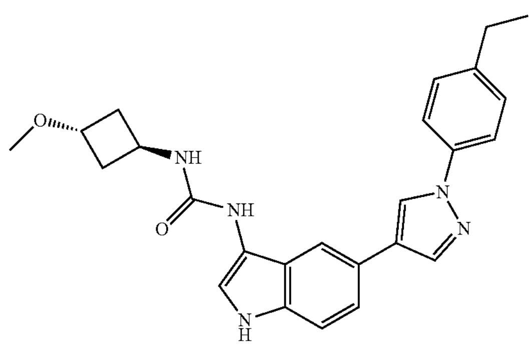 [SMILES: CCc1ccc(-n2cc(-c3ccc4[nH]cc(NC(=O)N[C@H]5C[C@H](OC)C5)c4c3)cn2)cc1] | 1-(5-(1-(4-ethylphenyl)-1H-pyrazol-4-yl)-1H-indol-3-yl)-3-((1r,3r)-3-methoxycyclobutyl)urea | 430.2 |
| 26 | 124 | 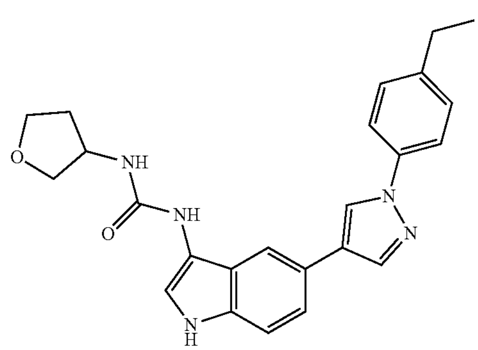 [SMILES: CCc1ccc(-n2cc(-c3ccc4[nH]cc(NC(=O)NC5CCOC5)c4c3)cn2)cc1] | 1-(5-(1-(4-ethylphenyl)-1H-pyrazol-4-yl)-1H-indol-3-yl)-3-(tetrahydrofuran-3-yl)urea | 416.2 |

-continued
| Example # | Compound # | Structure | IUPAC Name | LC-MS, MS-ESI, —[M + H]+. Methods BA or BB |
|---|---|---|---|---|
| 27 | 119 | 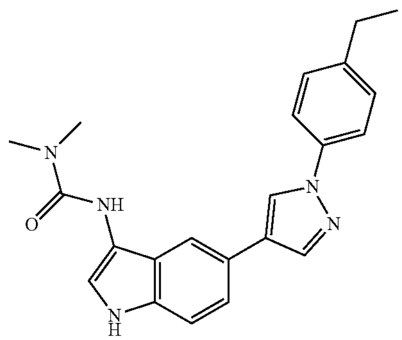 [SMILES: CCc1ccc(-n2cc(-c3ccc4[nH]cc(NC(=O)N(C)C)c4c3)cn2)cc1] | 3-(5-(1-(4-ethylphenyl)-1H-pyrazol-4-yl)-1H-indol-3-yl)-1,1-dimethylurea | 374.2 |
| 28 | 112 | 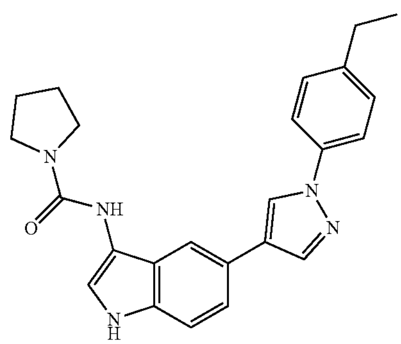 [SMILES: CCc1ccc(-n2cc(-c3ccc4[nH]cc(NC(=O)N5CCCC5)c4c3)cn2)cc1] | N-(5-(1-(4-ethylphenyl)-1H-pyrazol-4-yl)-1H-indol-3-yl)pyrrolidine-1-carboxamide | 400.3 |
| 29 | 128 | 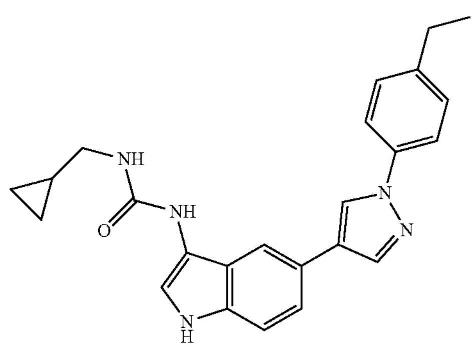 [SMILES: CCc1ccc(-n2cc(-c3ccc4[nH]cc(NC(=O)NCC5CC5)c4c3)cn2)cc1] | 1-(cyclopropylmethyl)-3-(5-(1-(4-ethylphenyl)-1H-pyrazol-4-yl)-1H-indol-3-yl)urea | 400.2 |
Example 30: Synthesis of 1-(5-(1-(4-ethylphenyl)-1H-pyrazol-4-yl)-1H-indol-3-yl)-3-(2-methoxyethyl)urea (Compound 110)
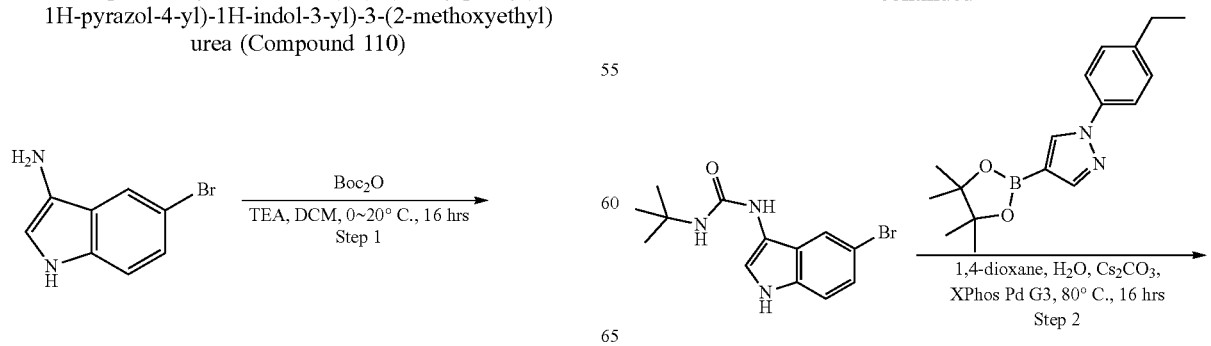

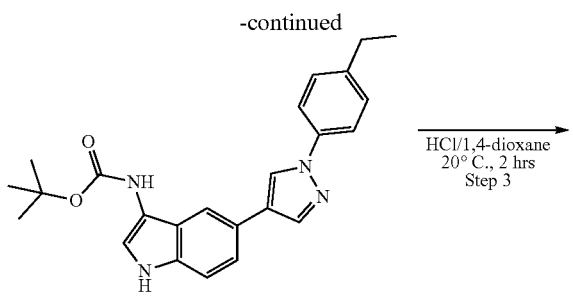

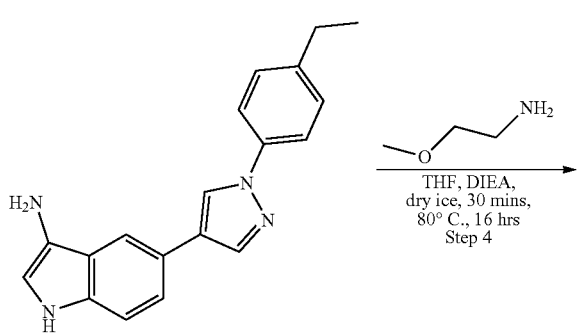

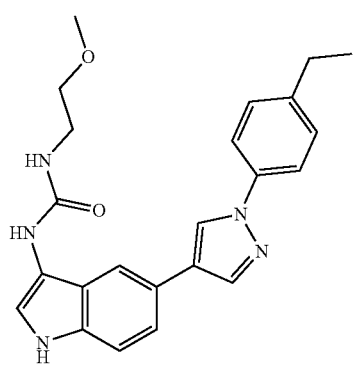

Compound 110

Step 1: Synthesis of tert-butyl N-(5-bromo-1H-indol-3-yl)carbamate 5-bromo-1H-indol-3-amine (5 g, 9.7 mmol, 1.0 equiv.) (prepared as shown in Example 19) was dissolved in DCM (100 mL) and cooled to 0° C. Then TEA (96.96 mmol, 13.50 mL, 10.0 equiv.) was added, followed by the addition of Boc$_2$O (2.54 g, 11.6 mmol, 1.2 equiv.). The reaction mixture was allowed to warm to ambient temperature. After 16 hours, the mixture was concentrated under vacuum. The residue was dissolved with 200 mL of ethyl acetate, then washed with 150 mL of H$_2$O, dried over anhydrous Na$_2$SO$_4$, and concentrated under vacuum to give tert-butyl N-(5-bromo-1H-indol-3-yl)carbamate (2.9 g) as a black solid that was used directly without further purification. MS-ESI, 255.1, 257.1 [M-55].

Step 2: Synthesis of tert-butyl N-[5-[1-(4-ethylphenyl)pyrazol-4-yl]-1H-indol-3-yl]carbamate Tert-butyl N-(5-bromo-1H-indol-3-yl)carbamate (2.9 g, 9.32 mmol, 1 equiv.) and 1-(4-ethylphenyl)-4-(4,4,5,5-tetramethyl-1,3,2-dioxaborolan-2-yl)pyrazole (3.14 g, 10.5 mmol, 1.12 equiv.) were dissolved in H$_2$O (5 mL) and 1,4-dioxane (50 mL). Then Cs$_2$CO$_3$ (7.29 g, 22.4 mmol, 2.4 equiv.) and XPhos Pd G3 (631.1 mg, 746 µmol, 0.08 equiv.) were added under an atmosphere of nitrogen. The mixture was heated at 80° C. for 16 hours, then 30 mL of H$_2$O was added. The mixture was extracted with ethyl acetate and the combined organic layers were dried over anhydrous Na$_2$SO$_4$, filtered and concentrated under vacuum. The residue was purified by flash column chromatography on silica gel, (Petroleum ether/Ethyl acetate=0 to 20%) to give tert-butyl N-[5-[1-(4-ethylphenyl)pyrazol-4-yl]-1H-indol-3-yl] carbamate (1.74 g, 4.32 mmol) as a white solid. MS-ESI, 403.2 [M+H$^+$].

Step 3: Synthesis of 5-[1-(4-ethylphenyl)pyrazol-4-yl]-1H-indol-3-amine

Tert-butyl N-[5-[1-(4-ethylphenyl)pyrazol-4-yl]-1H-indol-3-yl]carbamate (1.74 g, 4.32 mmol, 1.0 equiv.) was dissolved in DCM (50 mL), then HCl (4 M in 1,4-dioxane, 20 mL) was added. The mixture was stirred at ambient temperature for 2 hours, during which time the solution turned reddish-brown and a solid formed. The mixture was concentrated under vacuum to give 5-[1-(4-ethylphenyl)pyrazol-4-yl]-1H-indol-3-amine (2.1 g) as a light brown solid that was used directly without further purification. MS-ESI, 303.2 [M+H$^+$].

Step 4: Synthesis of 1-(5-(1-(4-ethylphenyl)-1H-pyrazol-4-yl)-1H-indol-3-yl)-3-(2-methoxyethyl)urea 4-nitrophenyl chloroformate (110 mg, 0.55 mmol, 1.1 equiv.) was dissolved in THF (3.0 mL) and cooled to −30° C. Then a solution of 5-(1-(4-ethylphenyl)-1H-pyrazol-4-yl)-1H-indol-3-amine (151 mg, 0.50 mmol, 1.0 equiv.) and N,N-diisopropylethylamine (330 µl, 2.0 mmol, 4.0 equiv.) dissolved in THF (2 mL) was added dropwise over 0.5 minute, maintaining the temperature at −30° C. The mixture was stirred at −30° C. for 30 minutes. Then a solution of 2-methoxyethanamine (187 mg, 2.50 mmol, 5.0 equiv.) dissolved in THF (1 mL) was added dropwise over 0.5 minute, maintaining the temperature at −30° C. The reaction mixture was warmed to ambient temperature and then heated at 80° C. for 16 hours. After cooling to ambient temperature, H$_2$O (6 mL) was added to the reaction mixture and then extracted with EtOAc. The combined organic layers were concentrated by SpeedVac and the residue was purified by prep HPLC to give 1-(5-(1-(4-ethylphenyl)-1H-pyrazol-4-yl)-1H-indol-3-yl)-3-(2-methoxyethyl) urea. MS-ESI, 404.2 [M+H$^+$].

$^1$H NMR (400 MHz, DMSO-d6) δ ppm 10.65 (s, 1H), 8.79 (s, 1H), 8.26 (s, 1H), 8.05 (s, 1H), 7.72-7.84 (m, 3H), 7.28-7.46 (m, 5H), 6.10 (br t, J=5.5 Hz, 1H), 5.75 (s, 1H), 3.42-3.37 (m, 2H), 3.31-3.25 (m, 5H), 2.65 (q, J=7.5 Hz, 2H), 2.08 (s, 1H), 1.22 (t, J=7.5 Hz, 3H).

The following compounds were synthesized using methods described for Example 19, above.

| Example # | Compound # | Structure | IUPAC Name | LC-MS, MS-ESI, — [M + H]+. Methods BA or BB |
|---|---|---|---|---|
| 31 | 111 | 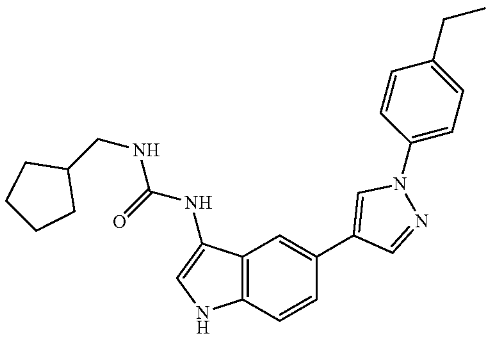 [SMILES: CCc1ccc(-n2cc(-c3ccc4[nH]cc(NC(=O)NCC5CCCC5)c4c3)cn2)cc1] | 1-(cyclopentyl-methyl)-3-{5-[1-(4-ethylphenyl)-1H-pyrazol-4-yl]-1H-indol-3-yl}urea | 428.3 |
| 32 | 108 | 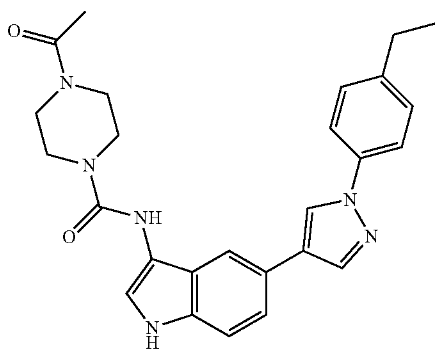 [SMILES: CCc1ccc(-n2cc(-c3ccc4[nH]cc(NC(=O)N5CCN(C(C)=O)CC5)c4c3)cn2)cc1] | 4-acetyl-N-{5-[1-(4-ethylphenyl)-1H-pyrazol-4-yl]-1H-indol-3-yl}piperazine-1-carboxamide | 457.3 |

Biological Assays

STING pathway activation by the compounds described herein was measured using THP1-Dual™ cells (KO-IFNAR2).

THP1-Dual™ KO-IFNAR2 Cells (obtained from invivogen) were maintained in RPMI, 10% FCS, 5 ml P/S, 2 mM L-glut, 10 mM Hepes, and 1 mM sodium pyruvate. Compounds were spotted in empty 384 well tissue culture plates (Greiner 781182) by Echo for a final concentration of 0.0017-100 μM. Cells were plated into the TC plates at 40 μL per well, 2×10E6 cells/mL. For activation with STING ligand, 2'3'cGAMP (MW 718.38, obtained from Invivogen), was prepared in Optimem media.

The following solutions were prepared for each 1×384 plate:
  Solution A: 2 mL Optimem with one of the following stimuli:
    60 μL of 10 mM 2'3'cGAMP→150 μM stock
  Solution B: 2 mL Optimem with 60 μL Lipofectamine 2000→Incubate 5 min at RT 2 mL of solution A and 2 ml Solution B was mixed and incubated for 20 min at room temperature (RT). 20 μL of transfection solution (A+B) was added on top of the plated cells, with a final 2'3'cGAMP concentration of 15 μM. The plates were then centrifuged immediately at 340 g for 1 minute, after which they were incubated at 37° C., 5% $CO_2$, >98% humidity for 24 h. Luciferase reporter activity was then measured. $EC_{50}$ values were calculated by using standard methods known in the art.

Luciferase reporter assay: 10 μL of supernatant from the assay was transferred to white 384-plate with flat bottom and squared wells. One pouch of QUANTI-Luc™ Plus was dissolved in 25 mL of water. 100 μL of QLC Stabilizer per 25 mL of QUANTI-Luc™ Plus solution was added. 50 μL of QUANTI-Luc™ Plus/QLC solution per well was then added. Luminescence was measured on a Platereader (e.g., Spectramax I3X (Molecular Devices GF3637001)).

Luciferase reporter activity was then measured. $EC_{50}$ values were calculated by using standard methods known in the art.

Table BA shows the activity of compounds in STING reporter assay: <0.008 μM="++++++"; ≥0.008 and <0.04 μM="+++++"; ≥0.04 and <0.2 μM="++++"; ≥0.2 and <1 μM="+++"; ≥1 and <5 μM="++"; ≥5 and <100 μM="+".

TABLE BA

| Compound No. | hSTING $EC_{50}$ |
|---|---|
| 101 | ++ |
| 102 | +++ |
| 103 | +++ |
| 104 | +++ |
| 105 | +++ |
| 106 | +++ |
| 107 | +++ |
| 108 | ++ |
| 109 | +++ |
| 110 | +++ |
| 111 | +++ |
| 112 | +++ |
| 113 | +++ |
| 114 | ++++ |
| 115 | ++ |
| 116 | + |
| 117 | + |
| 118 | +++ |
| 119 | +++ |

TABLE BA-continued

| Compound No. | hSTING EC$_{50}$ |
|---|---|
| 120 | +++ |
| 121 | + |
| 122 | ++ |
| 123 | + |
| 124 | +++ |
| 125 | +++ |
| 126 | +++ |
| 127 | +++ |
| 128 | +++ |
| 129 | ++++ |
| 130 | +++ |
| 131 | ++ |
| 132 | +++ |

Numbered Clauses

The compounds, compositions, methods, and other subject matter described herein are further described in the following numbered clauses:

1. A compound of Formula (I):

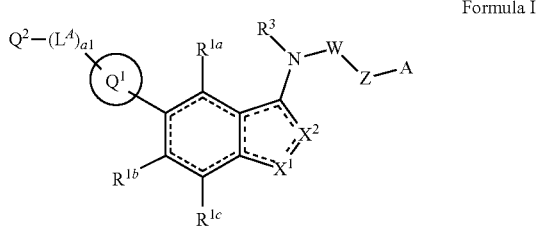

Formula I or a pharmaceutically acceptable salt thereof or a tautomer thereof, wherein:

$X^1$ is selected from the group consisting of O, S, N, $NR^2$, and $CR^5$;

$X^2$ is selected from the group consisting of O, S, N, $NR^4$, and $CR^5$;

each ═══ is independently a single bond or a double bond, provided that the five-membered ring comprising $X^1$ and $X^2$ is heteroaryl, and the 6-membered ring

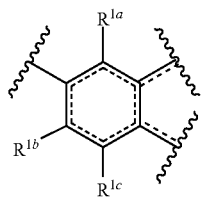

is aromatic;

$R^{1a}$, $R^{1b}$, $R^{1c}$, and $R^5$ are each independently selected from the group consisting of: H; $R^c$; $R^h$; and -(L$^1$)$_{b1}$-$R^h$;

each occurrence of $R^2$ and $R^4$ is independently selected from the group consisting of: H; $R^d$; $R^g$; and -(L$^2$)$_{b2}$-$R^g$;

$Q^1$ is selected from the group consisting of:

C$_{3-12}$ cycloalkylene or C$_{3-12}$ cycloalkenylene, each optionally substituted with 1-4 substituents independently selected from the group consisting of oxo, $R^c$, and $R^h$;

heterocyclylene or heterocycloalkenylene of 3-12 ring atoms, wherein 1-3 ring atoms are heteroatoms, each independently selected from the group consisting of N, N(H), N(R$^d$), O, and S(O)$_{0-2}$, and wherein the heterocyclylene or heterocycloalkenylene is optionally substituted with 1-4 substituents independently selected from the group consisting of oxo, $R^c$, and $R^h$;

heteroarylene of 5-12 ring atoms, wherein 1-3 ring atoms are heteroatoms, each independently selected from the group consisting of N, N(H), N(R$^d$), O, and S(O)$_{0-2}$, and wherein the heteroarylene is optionally substituted with 1-4 substituents independently selected from the group consisting of $R^c$ and $R^h$; and C$_{6-10}$ arylene optionally substituted with 1-4 substituents independently selected from the group consisting of $R^c$ and $R^h$;

each $L^A$ is independently selected from the group consisting of: C$_{1-3}$ alkylene optionally substituted with 1-2 $R^a$; —O—; —NH—; —NR$^d$; —S(O)$_{0-2}$; and C(O);

a1 is 0, 1, 2, 3, or 4;

provided that -(L')$_{a1}$- cannot contain bond(s) between O, N, or S(O)$_0$ atoms, unless an N—N bond is further attached to C(O);

$Q^2$ is $R^g$;

$R^3$ is selected from the group consisting of: H; $R^d$; and $R^h$;

W is selected from the group consisting of:

(i) C(═O); (ii) C(═S); (iii) S(O)$_{1-2}$; (iv) C(═NR$^d$) or C(═N—CN); (v) C(═NH); (vi) C(═CH—NO$_2$); (vii) S(═O)(═N(R$^d$)); and (viii) S(═O)(═NH);

Z and A are defined according to (AA) or (BB) below:

(AA)

Z is —N(H)— or —N(R$^d$)—;

A is selected from the group consisting of:

H;

C$_{1-10}$ alkyl which is optionally substituted with 1-6 $R^b$; and

—(Y$^{A1}$)$_{nA}$—Y$^{A2}$ wherein:

nA is 0 or 1;

Y$^{A1}$ is C$_{1-6}$ alkylene optionally substituted with 1-3 $R^b$; and

Y$^{A2}$ is selected from the group consisting of:

monocyclic C$_{3-8}$ cycloalkyl or C$_{3-8}$ cycloalkenyl, each of which is optionally substituted with 1-4 substituents independently selected from the group consisting of oxo and $R^c$; and monocyclic heterocyclyl or heterocycloalkenyl of 3-8 ring atoms, wherein 1-3 ring atoms are heteroatoms, each independently selected from the group consisting of N, N(H), N(R$^d$), O, and S(O)$_{0-2}$, and wherein the heterocyclyl or heterocycloalkenyl is optionally substituted with 1-4 substituents independently selected from the group consisting of oxo and $R^c$; or Z and A, taken together, form:

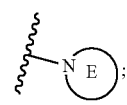

(BB)

and

Ring E is a saturated or partially unsaturated ring of 3-16 ring atoms, wherein 0-3 ring atoms are heteroatoms (in addition to the nitrogen atom already present), each independently selected from the group consisting of N, N(H), N(R$^d$), O, and S(O)$_{0-2}$, and wherein the ring is optionally substituted with 1-4 substituents independently selected from the group consisting of: oxo, $R^c$, $R^h$, and -$(L^g)_{bg}$-$R^h$;

each occurrence of $R^a$ and $R^b$ is independently selected from the group consisting of: —OH; -halo; —NR$^e$R$^f$; $C_{1-4}$ alkoxy; $C_{1-4}$ haloalkoxy; —C(=O)O($C_{1-4}$ alkyl); —C(=O)($C_{1-4}$ alkyl); —C(=O)OH; —CONR'R"; —S(O)$_{1-2}$NR'R"; —S(O)$_{1-2}$($C_{1-4}$ alkyl); and cyano;

each occurrence of $R^c$ is independently selected from the group consisting of: halo; cyano; $C_{1-10}$ alkyl which is optionally substituted with 1-6 independently selected $R^a$; $C_{2-6}$ alkenyl; $C_{2-6}$ alkynyl; $C_{1-4}$ alkoxy; $C_{1-4}$ haloalkoxy; —S(O)$_{1-2}$($C_{1-4}$ alkyl); —S(O)(=NH)($C_{1-4}$ alkyl); —NR$^e$R$^f$; —OH; —S(O)$_{1-2}$NR'R"; —$C_{1-4}$ thioalkoxy; —NO$_2$; —C(=O)($C_{1-10}$ alkyl); —C(=O)O ($C_{1-4}$ alkyl); —C(=O)OH; —C(=O)NR'R"; and —SF$_5$;

each occurrence of $R^d$ is independently selected from the group consisting of: $C_{1-6}$ alkyl optionally substituted with 1-3 independently selected $R^a$; —C(O)($C_{1-4}$ alkyl); —C(O)O($C_{1-4}$ alkyl); —CONR'R"; —S(O)$_{1-2}$NR'R"; —S(O)$_{1-2}$($C_{1-4}$ alkyl); —OH; and $C_{1-4}$ alkoxy;

each occurrence of $R^e$ and $R^f$ is independently selected from the group consisting of: H; $C_{1-6}$ alkyl optionally substituted with 1-3 substituents each independently selected from the group consisting of NR'R", —OH, and $R^i$; —C(O)($C_{1-4}$ alkyl); —C(O)O($C_{1-4}$ alkyl); —CONR'R"; —S(O)$_{1-2}$NR'R"; —S(O)$_{1-2}$($C_{1-4}$ alkyl); —OH; and $C_{1-4}$ alkoxy;

each occurrence of $R^g$ is independently selected from the group consisting of:
- $C_{3-12}$ cycloalkyl or $C_{3-12}$ cycloalkenyl, each of which is optionally substituted with 1-4 substituents independently selected from the group consisting of oxo, $R^c$, $R^h$, and -$(L^g)_{bg}$-$R^h$;
- heterocyclyl or heterocycloalkenyl of 3-12 ring atoms, wherein 1-3 ring atoms are heteroatoms, each independently selected from the group consisting of N, N(H), N($R^d$), O, and S(O)$_{0-2}$, and wherein the heterocyclyl or heterocycloalkenyl is optionally substituted with 1-4 substituents independently selected from the group consisting of oxo, $R^c$, $R^h$, and -$(L^g)_{bg}$-$R^h$;
- heteroaryl of 5-12 ring atoms, wherein 1-3 ring atoms are heteroatoms, each independently selected from the group consisting of N, N(H), N($R^d$), O, and S(O)$_{0-2}$, and wherein the heteroaryl is optionally substituted with 1-4 substituents independently selected from the group consisting of $R^c$, $R^h$, and -$(L^g)_{bg}$-$R^h$; and
- $C_{6-10}$ aryl optionally substituted with 1-4 substituents independently selected from the group consisting of $R^c$, $R^h$, and -$(L^g)_{bg}$-$R^h$.

each occurrence of $R^h$ is independently selected from the group consisting of:
- $C_{3-8}$ cycloalkyl or $C_{3-8}$ cycloalkenyl, each of which is optionally substituted with 1-4 $R^i$;
- heterocyclyl or heterocycloalkenyl of 3-8 ring atoms, wherein 1-3 ring atoms are heteroatoms, each independently selected from the group consisting of N, N(H), N($R^d$), O, and S(O)$_{0-2}$, and wherein the heterocyclyl or heterocycloalkenyl is optionally substituted with 1-4 $R^i$;
- heteroaryl of 5-6 ring atoms, wherein 1-3 ring atoms are heteroatoms, each independently selected from the group consisting of N, N(H), N($R^d$), O, and S, and wherein the heteroaryl is optionally substituted with 1-4 $R^i$; and
- $C_6$ aryl optionally substituted with 1-4 $R^i$;

each occurrence of $R^i$ is independently selected from the group consisting of: $C_{1-6}$ alkyl; $C_{1-4}$ haloalkyl; $C_{1-4}$ alkoxy; $C_{1-4}$ haloalkoxy; and halo;

each occurrence of $L^1$, $L^2$, and $L^g$ is selected from the group consisting of: —O—, —NH—, —NR$^d$, —S(O)$_{0-2}$, C(O), and $C_{1-3}$ alkylene optionally substituted with 1-3 $R^a$;

b1, b2, and bg are each independently 1, 2, or 3; and each occurrence of R' and R" is independently selected from the group consisting of: H; —OH; and $C_{1-4}$ alkyl.

2. The compound of clause 1, wherein $Q^1$ is heteroarylene of 5-12 ring atoms, wherein 1-3 ring atoms are heteroatoms, each independently selected from the group consisting of N, N(H), N($R^d$), O, and S(O)$_{0-2}$, and wherein the heteroarylene is optionally substituted with 1-4 substituents independently selected from the group consisting of $R^c$ and $R^h$.

3. The compound of clauses 1 or 2, wherein $Q^1$ is heteroarylene of 5-6 ring atoms, wherein 1-3 ring atoms are heteroatoms, each independently selected from the group consisting of N, N(H), N($R^d$), O, and S, and wherein the heteroarylene is optionally substituted with 1-3 substituents independently selected from the group consisting of $R^c$ and $R^h$.

4. The compound of any one of clauses 1-3, wherein $Q^1$ is heteroarylene of 5-6 ring atoms, wherein 1-3 ring atoms are heteroatoms, each independently selected from the group consisting of N, N(H), N($R^d$), O, and S, and wherein the heteroarylene is optionally substituted with 1-3 $R^c$.

5. The compound of any one of clauses 1-4, wherein $Q^1$ is heteroarylene of 5 ring atoms, wherein 1-3 ring atoms are heteroatoms, each independently selected from the group consisting of N, N(H), N($R^d$), O, and S, and wherein the heteroarylene is optionally substituted with 1-2 $R^c$.

6. The compound of any one of clauses 1-5, wherein $Q^1$ is pyrazolylene which is optionally substituted with 1-2 $R^c$.

7. The compound of any one of clauses 1-6, wherein $Q^1$ is

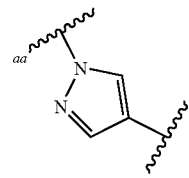

which is optionally substituted with 1-2 $R^c$, wherein aa represents point of attachment to -$(L^A)_{a1}$-$Q^2$.

8. The compound of any one of clauses 1-6, wherein $Q^1$ is

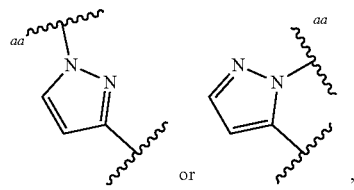

each of which is optionally substituted with 1-2 $R^c$, wherein aa represents point of attachment to -$(L^A)_{a1}$-$Q^2$.

9. The compound of any one of clauses 1-4, wherein $Q^1$ is heteroarylene of 6 ring atoms, wherein 1-3 ring atoms are ring nitrogen atoms, and wherein the heteroarylene is optionally substituted with 1-3 substituents independently selected from the group consisting of $R^c$ and $R^h$.

10. The compound of any one of clauses 1-4 or 9, wherein $Q^1$ is

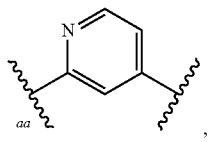 [SMILES: *c1ccnc(*)c1]

which is optionally substituted with 1-2 $R^c$, wherein aa represents point of attachment to -$(L^A)_{a1}$-$Q^2$.

11. The compound of clause 1, wherein $Q^1$ is $C_{6-10}$ arylene optionally substituted with 1-4 substituents independently selected from the group consisting of $R^c$ and $R^h$.

12. The compound of clauses 1 or 11, wherein $Q^1$ is phenylene which is optionally substituted with 1-3 substituents independently selected from the group consisting of $R^c$ and $R^h$.

13. The compound of any one of clauses 1 or 11-12, wherein $Q^1$ is

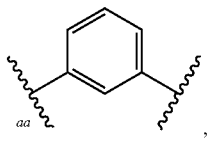

wherein aa represents point of attachment to -$(L^A)_{a1}$-$Q^2$.

14. The compound of any one of clauses 1-13, wherein a1 is 0.

15. The compound of any one of clauses 1-13, wherein a1 is 1.

16. The compound of any one of clauses 1-13 or 15, wherein $L^A$ is $CH_2$.

17. The compound of any one of clauses 1-13, wherein -$(L^A)_{a1}$- is $CH_2$.

18. The compound of any one of clauses 1-17, wherein $Q^2$ is selected from the group consisting of:
heteroaryl of 5-12 ring atoms, wherein 1-3 ring atoms are heteroatoms, each independently selected from the group consisting of N, N(H), N($R^d$), O, and S(O)$_{0-2}$, and wherein the heteroaryl is optionally substituted with 1-4 substituents independently selected from the group consisting of $R^c$, $R^h$, and -$(L^g)_{bg}$-$R^h$ and
$C_{6-10}$ aryl optionally substituted with 1-4 substituents independently selected from the group consisting of $R^c$, $R^h$, and -$(L^g)_{bg}$-$R^h$.

19. The compound of any one of clauses 1-18, wherein $Q^2$ is selected from the group consisting of:
heteroaryl of 5-6 ring atoms, wherein 1-3 ring atoms are heteroatoms, each independently selected from the group consisting of N, N(H), N($R^d$), O, and S, and wherein the heteroaryl is optionally substituted with 1-4 $R^{cq2}$; and
$C_6$ aryl optionally substituted with 1-4 $R^{cq2}$,
wherein each $R^{cq2}$ is an independently selected $R^c$ 20. The compound of any one of clauses 1-19, wherein $Q^2$ is selected from the group consisting of:
phenyl optionally substituted with 1-4 $R^{cq2}$; and
heteroaryl of 6 ring atoms, wherein 1-3 ring atoms are ring nitrogen atoms, and wherein the heteroaryl is optionally substituted with 1-4 $R^{cq2}$,
wherein each $R^{cq2}$ is an independently selected $R^c$.

21. The compound of any one of clauses 1-20, wherein $Q^2$ is phenyl or pyridyl, each optionally substituted with 1-2 $R^{cq2}$, wherein each $R^{cq2}$ is an independently selected $R^c$.

22. The compound of any one of clauses 1-20, wherein $Q^2$ has the following formula:

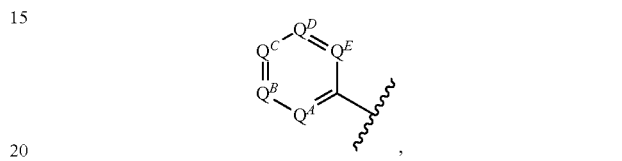

wherein $Q^A$, $Q^B$, $Q^C$, $Q^D$, and $Q^E$ are each independently selected from the group consisting of CH, $CR^{cq2}$, and N, provided that no more than 2 of $Q^A$-$Q^E$ are N, and no more than 2 of $Q^A$-$Q^E$ are $CR^{cq2}$, wherein each $R^{cq2}$ is an independently selected $R^c$.

23. The compound of clause 22, wherein $Q^A$, $Q^B$, $Q^C$, $Q^D$, and $Q^E$ are independently CH or $CR^{cq2}$, provided that no more than 2 of $Q^A$-$Q^E$ are $CR^{cq2}$.

24. The compound of clauses 22 or 23, wherein $Q^A$ and $Q^E$ are CH; and $Q^B$, $Q^C$, and $Q^D$ are independently CH or $CR^{cq2}$, provided that no more than 2 of $Q^A$-$Q^E$ are $CR^{cq2}$.

25. The compound of clause 24, wherein $Q^B$ and $Q^D$ are CH; and $Q^C$ is $CR^{cq2}$.

26. The compound of clause 24, wherein $Q^B$ and $Q^C$ are CH; and $Q^D$ is $CR^{cq2}$.

27. The compound of clause 24, wherein $Q^B$, $Q^C$, and $Q^D$ are each CH.

28. The compound of clauses 22 or 23, wherein $Q^A$ is $CR^{cq2}$; and $Q^B$, $Q^C$, $Q^D$, and $Q^E$ are each CH.

29. The compound of any one of clauses 1-23, wherein $Q^2$ is selected from the group consisting of: unsubstituted phenyl,

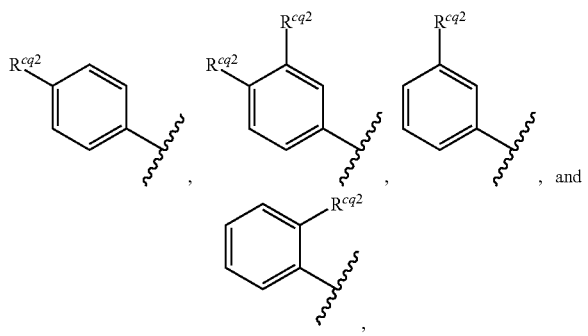

wherein each $R^{cq2}$ is an independently selected $R^c$.

30. The compound of clause 22, wherein 1-2 of $Q^A$-$Q^E$ is N; and each remaining one of $Q^A$-$Q^E$ is CH or $CR^{cq2}$, provided that no more than 2 of $Q^A$-$Q^E$ are $CR^{cq2}$.

31. The compound of clauses 22 or 30, wherein $Q^A$ is N; each of $Q^B$, $Q^C$, $Q^D$, and $Q^E$ is independently CH or $CR^{cq2}$, provided that no more than 2 of $Q^B$-$Q^E$ are $CR^{cq2}$.

32. The compound of any one of clauses 1-22 or 30-31, wherein $Q^2$ is

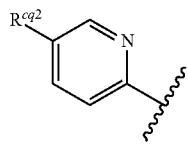

33. The compound of any one of clauses 1-17, wherein $Q^2$ is $C_{3-12}$ cycloalkyl or $C_{3-12}$ cycloalkenyl, each of which is optionally substituted with 1-4 substituents independently selected from the group consisting of oxo and $R^{cq2}$, wherein each $R^{cq2}$ is an independently selected $R^c$.

34. The compound of any one of clauses 1-17 or 33, wherein $Q^2$ is.
   (i) $C_{3-6}$ (e.g. $C_3$, $C_4$, $C_5$, or $C_6$) cycloalkyl, which is optionally substituted with 1-4 substituents independently selected from the group consisting of oxo and $R^{cq2}$; or
   (ii) cyclopropyl or cyclopentyl each of which is optionally substituted with 1-2 $R^{cq2}$; or
   (iii)

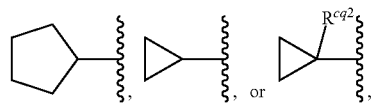

wherein each $R^{cq2}$ in (i), (ii), or (iii) is an independently selected $R^c$.

35. The compound of any one of clauses 1-17, wherein $Q^2$ is:
   (i) heterocyclyl or heterocycloalkenyl of 3-12 ring atoms, wherein 1-3 ring atoms are heteroatoms, each independently selected from the group consisting of N, N(H), N($R^d$), O, and S(O)$_{0-2}$, and wherein the heterocyclyl or heterocycloalkenyl is optionally substituted with 1-4 substituents independently selected from the group consisting of oxo and $R^{cq2}$;
   (ii) heterocyclyl of 4-8 ring atoms, wherein 1-3 ring atoms are heteroatoms, each independently selected from the group consisting of N, N(H), N($R^d$), O, and S(O)$_{0-2}$, and wherein the heterocyclyl is optionally substituted with 1-4 substituents independently selected from the group consisting of oxo and $R^{cq2}$; or
   (iii)

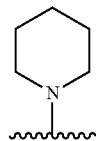

optionally substituted with 1-2 $R^{cq2}$,
   wherein each $R^{cq2}$ in (i), (ii), or (iii) is an independently selected $R^c$.

36. The compound of any one of clauses 19-35, wherein each $R^{cq2}$ is independently selected from the group consisting of: halo; cyano; $C_{1-6}$ alkyl which is optionally substituted with 1-6 independently selected $R^a$; $C_{1-4}$ alkoxy; $C_{1-4}$ haloalkoxy; and —$C_{1-4}$ thioalkoxy.

37. The compound of any one of clauses 19-36, wherein each $R^{cq2}$ is independently selected from the group consisting of: halo; cyano; $C_{1-6}$ alkyl (e.g., $C_{1-3}$ alkyl, e.g., ethyl); $C_{1-6}$ alkyl substituted with 1-6 independently selected $R^a$; $C_{1-4}$ alkoxy; $C_{1-4}$ haloalkoxy (e.g., —OCF$_3$ or —OCH$_2$CF$_3$); and —$C_{1-4}$ thioalkoxy.

38. The compound of any one of clauses 19-37, wherein each $R^{cq2}$ is independently selected from the group consisting of: halo; cyano; $C_{1-3}$ alkyl; $C_{1-3}$ alkyl substituted with 1-6 substituents each independently selected from the group consisting of -halo, $C_{1-3}$ alkoxy, and —OH (e.g., —CF$_3$, —CH$_2$CF$_3$, or —CH$_2$OMe); $C_{1-4}$ alkoxy; and $C_{1-4}$ haloalkoxy (e.g., —OCF$_3$ or —OCH$_2$CF$_3$).

39. The compound of any one of clauses 1-38, wherein $R^{1a}$ is —H.

40. The compound of any one of clauses 1-39, wherein $R^{1b}$ is —H.

41. The compound of any one of clauses 1-40, wherein $R^{1c}$ is —H.

42. The compound of any one of clauses 1-41, wherein $R^{1a}$ is —H; $R^{1b}$ is —H; and $R^{1c}$ is —H.

43. The compound of any one of clauses 1-42, wherein $X^1$ is $NR^2$.

44. The compound of any one of clauses 1-43, wherein $X^1$ is NH.

45. The compound of any one of clauses 1-44, wherein $X^2$ is $CR^5$.

46. The compound of any one of clauses 1-45, wherein $X^2$ is CH.

47. The compound of any one of clauses 1-42, wherein $X^1$ is $NR^2$; and $X^2$ is $CR^5$.

48. The compound of any one of clauses 1-42 or 47, wherein $X^1$ is NH; and $X^2$ is CH.

49. The compound of any one of clauses 1-48, wherein $R^3$ is —H.

50. The compound of any one of clauses 1-49, wherein W is C(=O).

51. The compound of any one of clauses 1-50, wherein Z and A are defined according to (AA).

52. The compound of any one of clauses 1-51, wherein Z is —N(H)—.

53. The compound of any one of clauses 1-51, wherein Z is —N($R^d$)—.

54. The compound of any one of clauses 1-51 or 53, wherein Z is —N($C_{1-3}$ alkyl)-, optionally —N(Me)-.

55. The compound of any one of clauses 1-54, wherein A is H.

56. The compound of any one of clauses 1-54, wherein A is $C_{1-10}$ alkyl which is optionally substituted with 1-6 $R^b$.

57. The compound of any one of clauses 1-54 or 56, wherein A is $C_{1-6}$ (e.g., $C_1$, $C_2$, $C_3$, or $C_4$) alkyl, which is optionally substituted with 1-6 $R^b$.

58. The compound of any one of clauses 1-54 or 56-57, wherein A is unsubstituted $C_{1-6}$ alkyl.

59. The compound of any one of clauses 1-54 or 56-58, wherein A is methyl, ethyl, propyl, isopropyl, or isobutyl.

60. The compound of any one of clauses 1-54 or 56-57, wherein A is $C_{1-6}$ alkyl which is substituted with 1-6 substituents each independently selected from the group consisting of: —OH; -halo; —NR$^e$R$^f$, optionally —N($C_{1-3}$ alkyl)$_2$ or NHC(O)O($C_{1-4}$ alkyl); $C_{1-4}$ alkoxy, optionally —OMe; $C_{1-4}$ haloalkoxy; —C(=O)O($C_{1-4}$ alkyl); —C(=O)($C_{1-4}$ alkyl); and cyano.

61. The compound of any one of clauses 1-54, 56-57, or 60, wherein A is $C_{1-6}$ alkyl substituted with 1-6 independently selected halo.

62. The compound of any one of clauses 1-54, 56-57, or 60-61, wherein A is —CH$_2$CF$_3$, —CH$_2$CH$_2$CF$_3$, or —CH$_2$CHF$_2$.

63. The compound of any one of clauses 1-54, 56-57, or 60, wherein A is C$_{1-6}$ alkyl substituted with —OH, C$_{1-4}$ alkoxy, or C$_{1-4}$ haloalkoxy.

64. The compound of any one of clauses 1-54, 56-57, 60, or 63, wherein A is

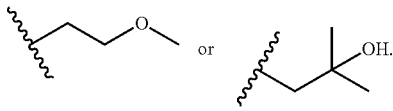

65. The compound of any one of clauses 1-54, wherein A is —(Y$^{A1}$)$_{nA}$—Y$^{A2}$.

66. The compound of clause 65, wherein nA is 0.

67. The compound of clause 65, wherein nA is 1.

68. The compound of clauses 65 or 67, wherein Y$^{A1}$ is C$_{1-3}$ alkylene optionally substituted with 1-3 R$^b$.

69. The compound of any one of clauses 65 or 67-68, wherein Y$^{A1}$ is —CH$_2$—.

70. The compound of any one of clauses 65-69, wherein Y$^{A2}$ is monocyclic C$_{3-8}$ cycloalkyl or C$_{3-8}$ cycloalkenyl, each of which is optionally substituted with 1-4 substituents independently selected from the group consisting of oxo and R$^c$.

71. The compound of any one of clauses 65-70, wherein Y$^{A2}$ is monocyclic C$_{3-8}$ cycloalkyl which is optionally substituted with 1-2 substituents independently selected from the group consisting of oxo and R$^c$.

72. The compound of any one of clauses 65-71, wherein Y$^{A2}$ is monocyclic C$_{3-6}$ cycloalkyl which is optionally substituted with 1-2 R$^c$.

73. The compound of any one of clauses 65-72, wherein Y$^{A2}$ is selected from the group consisting of cyclopropyl; cyclobutyl; and cyclopentyl, each of which is optionally substituted with 1-2 R$^c$.

74. The compound of any one of clauses 65-69, wherein Y$^{A2}$ is monocyclic heterocyclyl or heterocycloalkenyl of 3-8 ring atoms, wherein 1-3 ring atoms are heteroatoms, each independently selected from the group consisting of N, N(H), N(R$^d$), O, and S(O)$_{0-2}$, and wherein the heterocyclyl or heterocycloalkenyl is optionally substituted with 1-4 substituents independently selected from the group consisting of oxo and R$^c$.

75. The compound of any one of clauses 65-69 or 74, wherein Y$^{A2}$ is monocyclic heterocyclyl of 3-8 ring atoms, wherein 1-3 ring atoms are heteroatoms, each independently selected from the group consisting of N, N(H), N(R$^d$), O, and S(O)$_{0-2}$, and wherein the heterocyclyl is optionally substituted with 1-2 substituents independently selected from the group consisting of oxo and R$^c$.

76. The compound of any one of clauses 65-69 or 74-75, wherein Y$^{A2}$ is oxetanyl, tetrahydrofuranyl, or pyrrolidinyl, each of which is optionally substituted with 1-2 R$^c$, and the pyrrolidinyl is optionally substituted with R$^d$ at a ring nitrogen atom.

77. The compound of any one of clauses 1-50, wherein Z and A are defined according to (BB).

78. The compound of any one of clauses 1-50 or 77, wherein Z and A, taken together, form:

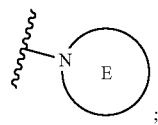 [SMILES: *N]

and

Ring E is a saturated or partially unsaturated ring of 3-8 ring atoms, wherein 0-2 ring atoms are heteroatoms (in addition to the ring nitrogen atom already present), each independently selected from the group consisting of N, N(H), N(R$^d$), O, and S(O)$_{0-2}$, and wherein the ring is optionally substituted with 1-4 substituents independently selected from the group consisting of: oxo, R$^c$, R$^h$, and -(L$^g$)$_{bg}$-R$^h$.

79. The compound of any one of clauses 1-50 or 77-78, wherein Z and A, taken together, form:

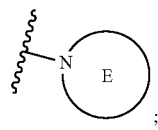

and

Ring E is a saturated ring of 3-8 ring atoms, wherein 0-2 ring atoms are heteroatoms (in addition to the ring nitrogen atom already present), each independently selected from the group consisting of N, N(H), N(R$^d$), O, and S(O)$_{0-2}$, and wherein the ring is optionally substituted with 1-4 substituents independently selected from the group consisting of: oxo and R$^c$.

80. The compound of any one of clauses 1-50 or 77-79, wherein Z and A, taken together, form:

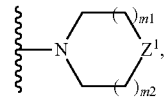

wherein m1 and m2 are independently 0, 1, or 2, wherein Z$^1$ is CH$_2$, CH(R$^c$), C(R$^c$)$_2$, NH, or N(R$^d$).

81. The compound of clause 80, wherein m1 and m2 are independently 0 or 1.

82. The compound of clauses 80 or 81, wherein Z$^1$ is CH$_2$ or N(R$^d$); or Z$^1$ is CH$_2$ or NC(=O)(C$_{1-3}$ alkyl).

83. The compound of clause 1, wherein the compound is a compound of Formula (Ia):

Formula Ia

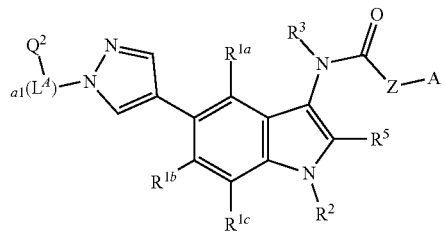

or a pharmaceutically acceptable salt thereof, wherein:
$L^A$ is —CH$_2$—; and
a1 is 0 or 1.

84. The compound of clause 83, wherein a1 is 0.
85. The compound of clause 83, wherein a1 is 1.
86. The compound of any one of clauses 83-85, wherein $Q^2$ has the following formula:

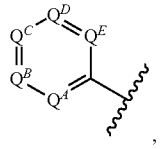

wherein $Q^A$, $Q^B$, $Q^C$, $Q^D$, and $Q^E$ are each independently selected from the group consisting of CH, CR$^{cq2}$, and N, provided that no more than 2 of $Q^A$-$Q^E$ are N, and no more than 2 of $Q^A$-$Q^E$ are CR$^{cq2}$, wherein each R$^{cq2}$ is an independently selected R$^c$.

87. The compound of clause 86, wherein $Q^A$, $Q^B$, $Q^C$, $Q^D$, and $Q^E$ are independently CH or CR$^{cq2}$, provided that no more than 2 of $Q^A$-$Q^E$ are CR$^{cq2}$.
88. The compound of clauses 86 or 87, wherein $Q^A$ and $Q^E$ are CH; and $Q^B$, $Q^C$, and $Q^D$ are independently CH or CR$^{cq2}$, provided that no more than 2 of $Q^A$-$Q^E$ are CR$^{cq2}$.
89. The compound of clause 88, wherein $Q^B$ and $Q^D$ are CH; and $Q^C$ is CR$^{cq2}$.
90. The compound of clause 88, wherein $Q^B$ and $Q^C$ are CH; and $Q^D$ is CR$^{cq2}$.
91. The compound of clause 88, wherein $Q^B$, $Q^C$, and $Q^D$ are each CH.
92. The compound of clauses 86 or 87, wherein $Q^A$ is CR$^{cq2}$; and $Q^B$, $Q^C$, $Q^D$, and $Q^E$ are each CH.
93. The compound of any one of clauses 83-87, wherein $Q^2$ is selected from the group consisting of: unsubstituted phenyl,

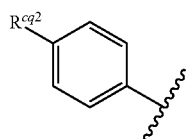

,

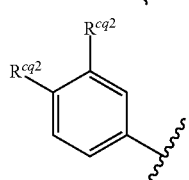

,

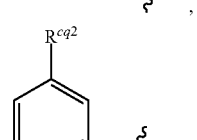

, and

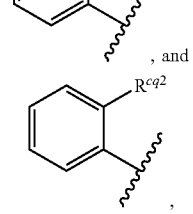

, wherein each R$^{cq2}$ is an independently selected R$^c$.

94. The compound of clause 86, wherein 1-2 of $Q^A$-$Q^E$ is N; and each remaining one of $Q^A$-$Q^E$ is CH or CR$^{cq2}$, provided that no more than 2 of $Q^A$-$Q^E$ are CR$^{cq2}$.
95. The compound of clauses 86 or 94, wherein $Q^A$ is N; each of $Q^B$, $Q^C$, $Q^D$, and $Q^E$ is independently CH or CR$^{cq2}$, provided that no more than 2 of $Q^B$-$Q^E$ are CR$^{cq2}$.
96. The compound of any one of clauses 83-86 or 94-95, wherein $Q^2$ is

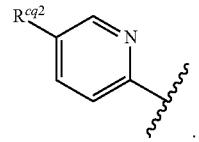

.

97. The compound of any one of clauses 86-96, wherein each R$^{cq2}$ is independently selected from the group consisting of: halo; cyano; C$_{1-6}$ alkyl; C$_{1-6}$ alkyl substituted with 1-6 substituents each independently selected from the group consisting of -halo, C$_{1-3}$ alkoxy, and —OH; C$_{1-4}$ alkoxy; C$_{1-4}$ haloalkoxy; and —C$_{1-4}$ thioalkoxy.
98. The compound of any one of clauses 86-97, wherein each R$^{cq2}$ is independently selected from the group consisting of: —F, —Cl, cyano, C$_{1-3}$ alkyl, —CF$_3$, —CH$_2$CF$_3$, —CH$_2$OMe, —OCF$_3$, and —OCH$_2$CF$_3$.
99. The compound of any one of clauses 83-98, wherein R$^{1a}$ is —H; R$^{1b}$ is —H; and R$^{1c}$ is —H.
100. The compound of any one of clauses 83-99, wherein R$^2$ is H.
101. The compound of any one of clauses 83-100, wherein R$^5$ is H.
102. The compound of any one of clauses 83-101, wherein R$^3$ is H.
103. The compound of any one of clauses 83-102, wherein Z and A are defined according to (AA); and Z is —N(H)— or —N(C$_{1-3}$ alkyl)-.
104. The compound of any one of clauses 83-103, wherein A is H.
105. The compound of any one of clauses 83-103, wherein A is C$_{1-6}$ alkyl.
106. The compound of any one of clauses 83-103 or 105, wherein A is methyl, ethyl, propyl, or isopropyl.
107. The compound of any one of clauses 83-103, wherein A is C$_{1-6}$ alkyl which is substituted with 1-6 substituents each independently selected from the group consisting of: —OH; -halo; —NR$^e$R$^f$, optionally —N(C$_{1-3}$ alkyl)$_2$ or NHC(O)O(C$_{1-4}$ alkyl); C$_{1-4}$ alkoxy, optionally —OMe; C$_{1-4}$ haloalkoxy; —C(=O)O(C$_{1-4}$ alkyl); —C(=O)(C$_{1-4}$ alkyl); and cyano.
108. The compound of any one of clauses 83-103 or 107, wherein A is C$_{1-6}$ alkyl substituted with 1-6 independently selected halo.
109. The compound of any one of clauses 83-103 or 107-108, wherein A is —CH$_2$CF$_3$, —CH$_2$CH$_2$CF$_3$, or —CH$_2$CHF$_2$.
110. The compound of any one of clauses 83-103 or 107, wherein A is C$_{1-6}$ alkyl substituted with —OH, C$_{1-4}$ alkoxy, or C$_{1-4}$ haloalkoxy.
111. The compound of any one of clauses 83-103, 107, or 110, wherein A is

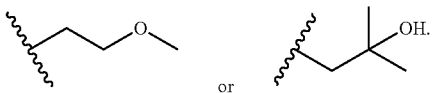

or

112. The compound of any one of clauses 83-103, wherein A is $Y^{A2}$ or —$CH_2$—$Y^{A2}$, wherein $Y^{A2}$ is selected from the group consisting of:
- monocyclic $C_{3-6}$ cycloalkyl, which is optionally substituted with 1-2 substituents independently selected from the group consisting of oxo and $R^c$; and
- monocyclic heterocyclyl of 4-6 ring atoms, wherein 1-2 ring atoms are heteroatoms, each independently selected from the group consisting of N, N(H), N($R^d$), O, and S(O)$_{0-2}$, and wherein the heterocyclyl is optionally substituted with 1-2 substituents independently selected from the group consisting of oxo and $R^c$.

113. The compound of any one of clauses 83-103 or 112, wherein A is $Y^{A2}$ or —$CH_2$—$Y^{A2}$, wherein $Y^{A2}$ is selected from the group consisting of:
- cyclopropyl; cyclobutyl; or cyclopentyl, each of which is optionally substituted with 1-2 $R^e$; and
- oxetanyl, tetrahydrofuranyl, or pyrrolidinyl, each of which is optionally substituted with 1-2 $R^c$, and the pyrrolidinyl is optionally substituted with $R^d$ at a ring nitrogen atom.

114. The compound of any one of clauses 83-102, wherein Z and A are defined according to (BB).

115. The compound of any one of clauses 83-102 or 114, wherein Z and A, taken together, form:

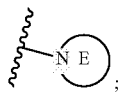

and
Ring E is a saturated ring of 3-8 ring atoms, wherein 0-2 ring atoms are heteroatoms (in addition to the ring nitrogen atom already present), each independently selected from the group consisting of N, N(H), N($R^d$), O, and S(O)$_{0-2}$, and wherein the ring is optionally substituted with 1-4 substituents independently selected from the group consisting of: oxo and $R^c$.

116. The compound of any one of clauses 83-102 or 114-115, wherein Z and A, taken together, form:

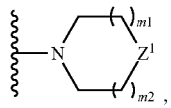

wherein m1 and m2 are independently 0, 1, or 2, wherein $Z^1$ is $CH_2$, CH($R^c$), C($R^c$)$_2$, NH, or N($R^d$).

117. The compound of clause 116, wherein m1 and m2 are independently 0 or 1.

118. The compound of clauses 116 or 117, wherein $Z^1$ is $CH_2$.

119. The compound of clauses 116 or 117, wherein $Z^1$ is N($R^d$), optionally NC(=O)($C_{1-3}$ alkyl).

120. The compound of clause 1, wherein the compound is selected from the group consisting of compounds delineated in Table C1, and a pharmaceutically acceptable salt thereof.

121. The compound of clause 1, wherein the compound is selected from the group consisting of the following, and a pharmaceutically acceptable salt thereof.

| Compound # | Name |
|---|---|
| 104 | 1-(2,2,2-trifluoroethyl)-3-(5-(1-(4-(trifluoromethyl)phenyl)-1H-pyrazol-4-yl)-1H-indol-3-yl)urea |
| 109 | 1-(cyclopropylmethyl)-3-(5-(1-(4-(trifluoromethyl)phenyl)-1H-pyrazol-4-yl)-1H-indol-3-yl)urea |
| 107 | 1-(2,2,2-trifluoroethyl)-3-(5-(1-(5-(trifluoromethyl)pyridin-2-yl)-1H-pyrazol-4-yl)-1H-indol-3-yl)urea |
| 106 | 1-(cyclopropylmethyl)-3-(5-(1-(5-(trifluoromethyl)pyridin-2-yl)-1H-pyrazol-4-yl)-1H-indol-3-yl)urea |
| 105 | 1-methyl-3-(5-(1-(4-(trifluoromethyl)benzyl)-1H-pyrazol-4-yl)-1H-indol-3-yl)urea |
| 103 | 1-(cyclopropylmethyl)-3-(5-(1-(4-(trifluoromethyl)benzyl)-1H-pyrazol-4-yl)-1H-indol-3-yl)urea |
| 102 | 1-(2-hydroxy-2-methylpropyl)-3-(5-(1-(4-(trifluoromethyl)phenyl)-1H-pyrazol-4-yl)-1H-indol-3-yl)urea |
| 101 | 1-(1-acetylpyrrolidin-3-yl)-3-(5-(1-(4-(trifluoromethyl)phenyl)-1H-pyrazol-4-yl)-1H-indol-3-yl)urea |
| 132 | 1-(5-(1-(4-ethylphenyl)-1H-pyrazol-4-yl)-1H-indol-3-yl)-3-methylurea |
| 118 | 1-methyl-3-(5-(1-(4-(trifluoromethyl)phenyl)-1H-pyrazol-4-yl)-1H-indol-3-yl)urea |
| 131 | 3-methyl-1-[5-(1-phenyl-1H-pyrazol-4-yl)-1H-indol-3-yl]urea |
| 115 | 1-{5-[1-(2-chlorophenyl)-1H-pyrazol-4-yl]-1H-indol-3-yl}-3-methylurea |
| 113 | 1-{5-[1-(3-chlorophenyl)-1H-pyrazol-4-yl]-1H-indol-3-yl}-3-methylurea |
| 116 | 1-{5-[1-(3-cyanophenyl)-1H-pyrazol-4-yl]-1H-indol-3-yl}-3-methylurea |
| 123 | 1-[5-(1-cyclopentyl-1H-pyrazol-4-yl)-1H-indol-3-yl]-3-methylurea |
| 122 | 1-[5-(3-cyclopropylphenyl)-1H-indol-3-yl]-3-methylurea |
| 121 | 1-{5-[4-(1-cyanocyclopropyl)phenyl]-1H-indol-3-yl}-3-methylurea |
| 117 | 3-methyl-1-{5-[2-(piperidin-1-yl)pyridin-4-yl]-1H-indol-3-yl}urea |
| 114 | 1-(5-(1-(4-ethylphenyl)-1H-pyrazol-4-yl)-1H-indol-3-yl)-3-(3,3,3-trifluoropropyl)urea |
| 130 | 1-(5-(1-(4-ethylphenyl)-1H-pyrazol-4-yl)-1H-indol-3-yl)-3-isopropylurea |
| 129 | 1-{5-(1-(4-ethylphenyl)-1H-pyrazol-4-yl)-1H-indol-3-yl}-3-(2,2,2-trifluoroethyl)urea |
| 127 | 1-(2,2-difluoroethyl)-3-(5-(1-(4-ethylphenyl)-1H-pyrazol-4-yl)-1H-indol-3-yl)urea |
| 126 | 1-cyclobutyl-3-(5-(1-(4-ethylphenyl)-1H-pyrazol-4-yl)-1H-indol-3-yl)urea |
| 120 | 1-cyclopentyl-3-(5-(1-(4-ethylphenyl)-1H-pyrazol-4-yl)-1H-indol-3-yl)urea |
| 125 | 1-(5-(1-(4-ethylphenyl)-1H-pyrazol-4-yl)-1H-indol-3-yl)-3-((1r,3r)-3-methoxycyclobutyl)urea |
| 124 | 1-(5-(1-(4-ethylphenyl)-1H-pyrazol-4-yl)-1H-indol-3-yl)-3-(tetrahydrofuran-3-yl)urea |
| 119 | 3-(5-(1-(4-ethylphenyl)-1H-pyrazol-4-yl)-1H-indol-3-yl)-1,1-dimethylurea |
| 112 | N-(5-(1-(4-ethylphenyl)-1H-pyrazol-4-yl)-1H-indol-3-yl)pyrrolidine-1-carboxamide |
| 128 | 1-(cyclopropylmethyl)-3-(5-(1-(4-ethylphenyl)-1H-pyrazol-4-yl)-1H-indol-3-yl)urea |
| 110 | 1-(5-(1-(4-ethylphenyl)-1H-pyrazol-4-yl)-1H-indol-3-yl)-3-(2-methoxyethyl) urea |
| 111 | 1-(cyclopentylmethyl)-3-{5-[1-(4-ethylphenyl)-1H-pyrazol-4-yl]-1H-indol-3-yl}urea |
| 108 | 4-acetyl-N-{5-[1-(4-ethylphenyl)-1H-pyrazol-4-yl]-1H-indol-3-yl}piperazine-1-carboxamide |

122. A pharmaceutical composition comprising a compound of clauses 1-121 and one or more pharmaceutically acceptable excipients.

123. A method for inhibiting STING activity, the method comprising contacting STING with a compound or a pharmaceutically acceptable salt thereof as defined in any one of clauses 1-121; or a pharmaceutical composition as defined in clause 122.

124. The method of clause 123, wherein the inhibiting comprises antagonizing STING.

125. The method of any one of clauses 123-124, which is carried out in vitro.

126. The method of clause 125, wherein the method comprises contacting a sample comprising one or more cells comprising STING with the compound.

127. The method of clause 125 or 126, wherein the one or more cells are one or more cancer cells.

128. The method of clause 126 or 127, wherein the sample further comprises one or more cancer cells, wherein the cancer is selected from the group consisting of melanoma, cervical cancer, breast cancer, ovarian cancer, prostate cancer, testicular cancer, urothelial carcinoma, bladder cancer, non-small cell lung cancer, small cell lung cancer, sarcoma, colorectal adenocarcinoma, gastrointestinal stromal tumors, gastroesophageal carcinoma, colorectal cancer, pancreatic cancer, kidney cancer, hepatocellular cancer, malignant mesothelioma, leukemia, lymphoma, myelodysplasia syndrome, multiple myeloma, transitional cell carcinoma, neuroblastoma, plasma cell neoplasms, Wilm's tumor, or hepatocellular carcinoma.

129. The method of clause 123 or 124, which is carried out in vivo.

130. The method of clause 129, wherein the method comprises administering the compound to a subject having a disease in which increased (e.g., excessive) STING signaling contributes to the pathology and/or symptoms and/or progression of the disease.

131. The method of clause 130, wherein the subject is a human.

132. The method of clause 131, wherein the disease is cancer.

133. The method of clause 132, wherein the cancer is selected from the group consisting of melanoma, cervical cancer, breast cancer, ovarian cancer, prostate cancer, testicular cancer, urothelial carcinoma, bladder cancer, non-small cell lung cancer, small cell lung cancer, sarcoma, colorectal adenocarcinoma, gastrointestinal stromal tumors, gastroesophageal carcinoma, colorectal cancer, pancreatic cancer, kidney cancer, hepatocellular cancer, malignant mesothelioma, leukemia, lymphoma, myelodysplasia syndrome, multiple myeloma, transitional cell carcinoma, neuroblastoma, plasma cell neoplasms, Wilm's tumor, or hepatocellular carcinoma.

134. The method of clause 132 or 133, wherein the cancer is a refractory cancer.

135. The method of clause 130, wherein the compound is administered in combination with one or more additional cancer therapies.

136. The method of clause 135, wherein the one or more additional cancer therapies comprises surgery, radiotherapy, chemotherapy, toxin therapy, immunotherapy, cryotherapy or gene therapy, or a combination thereof.

137. The method of clause 136, wherein chemotherapy comprises administering one or more additional chemotherapeutic agents.

138. The method of clause 137, wherein the one or more additional chemotherapeutic agents is selected from an alkylating agent (e.g., cisplatin, carboplatin, mechlorethamine, cyclophosphamide, chlorambucil, ifosfamide and/or oxaliplatin); an anti-metabolite (e.g., azathioprine and/or mercaptopurine); a terpenoid (e.g., a *vinca* alkaloid and/or a taxane; e.g., Vincristine, Vinblastine, Vinorelbine and/or Vindesine Taxol, Paclitaxel and/or Docetaxel); a topoisomerase (e.g., a type I topoisomerase and/or a type 2 topoisomerase; e.g., camptothecins, such as irinotecan and/or topotecan; amsacrine, etoposide, etoposide phosphate and/or teniposide); a cytotoxic antibiotic (e.g., actinomycin, anthracyclines, doxorubicin, daunorubicin, valrubicin, idarubicin, epirubicin, bleomycin, plicamycin and/or mitomycin); a hormone (e.g., a lutenizing hormone releasing hormone agonist; e.g., leuprolidine, goserelin, triptorelin, histrelin, bicalutamide, flutamide and/or nilutamide); an antibody (e.g., Abciximab, Adalimumab, Alemtuzumab, Atlizumab, Basiliximab, Belimumab, Bevacizumab, Bretuximab vedotin, Canakinumab, Cetuximab, Ceertolizumab pegol, Daclizumab, Denosumab, Eculizumab, Efalizumab, Gemtuzumab, Golimumab, Golimumab, Ibritumomab tiuxetan, Infliximab, Ipilimumab, Muromonab-CD3, Natalizumab, Ofatumumab, Omalizumab, Palivizumab, Panitumuab, Ranibizumab, Rituximab, Tocilizumab, Tositumomab and/or Trastuzumab); an anti-angiogenic agent; a cytokine; a thrombotic agent; a growth inhibitory agent; an anti-helminthic agent; and an immune checkpoint inhibitor that targets an immune checkpoint receptor selected from the group consisting of CTLA-4, PD-1, PD-L1, PD-1-PD-L1, PD-1-PD-L2, interleukin-2 (IL-2), indoleamine 2,3-dioxygenase (IDO), IL-10, transforming growth factor-β (TGFβ), T cell immunoglobulin and mucin 3 (TIM3 or HAVCR2), Galectin 9-TIM3, Phosphatidylserine-TIM3, lymphocyte activation gene 3 protein (LAG3), MHC class II-LAG3, 4-1BB-4-1BB ligand, OX40-OX40 ligand, GITR, GITR ligand-GITR, CD27, CD70-CD27, TNFRSF25, TNFRSF25-TL1A, CD40L, CD40-CD40 ligand, HVEM-LIGHT-LTA, HVEM, HVEM-BTLA, HVEM-CD160, HVEM-LIGHT, HVEM-BTLA-CD160, CD80, CD80-PDL-1, PDL2-CD80, CD244, CD48-CD244, CD244, ICOS, ICOS-ICOS ligand, B7-H3, B7-H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86-CD28, CD86-CTLA, CD80-CD28, CD39, CD73 Adenosine-CD39-CD73, CXCR4-CXCL12, Phosphatidylserine, TIM3, Phosphatidylserine-TIM3, SIRPA-CD47, VEGF, Neuropilin, CD160, CD30, and CD155 (e.g., CTLA-4 or PD1 or PD-L1).

139. The method of any one of clauses 130-138, wherein the compound is administered intratumorally.

140. A method of treating cancer, comprising administering to a subject in need of such treatment an effective amount of a compound as defined in any one of clauses 1-121, or a pharmaceutical composition as defined in clause 122.

141. The method of clause 140, wherein the cancer is selected from the group consisting of melanoma, cervical cancer, breast cancer, ovarian cancer, prostate cancer, testicular cancer, urothelial carcinoma, bladder cancer, non-small cell lung cancer, small cell lung cancer, sarcoma, colorectal adenocarcinoma, gastrointestinal stromal tumors, gastroesophageal carcinoma, colorectal cancer, pancreatic cancer, kidney cancer, hepatocellular cancer, malignant mesothelioma, leukemia, lymphoma, myelodysplasia syndrome, multiple myeloma, transitional cell carcinoma, neuroblastoma, plasma cell neoplasms, Wilm's tumor, or hepatocellular carcinoma.

142. The method of clause 140 or 141, wherein the cancer is a refractory cancer.

143. The method of clause 140, wherein the compound is administered in combination with one or more additional cancer therapies.

144. The method of clause 143, wherein the one or more additional cancer therapies comprises surgery, radiotherapy, chemotherapy, toxin therapy, immunotherapy, cryotherapy or gene therapy, or a combination thereof.

145. The method of clause 144, wherein chemotherapy comprises administering one or more additional chemotherapeutic agents.

146. The method of clause 144, wherein the one or more additional chemotherapeutic agents is selected from an alkylating agent (e.g., cisplatin, carboplatin, mechlorethamine, cyclophosphamide, chlorambucil, ifosfamide and/or oxaliplatin); an anti-metabolite (e.g., azathioprine and/or mercaptopurine); a terpenoid (e.g., a *vinca* alkaloid and/or a taxane; e.g., Vincristine, Vinblastine, Vinorelbine and/or Vindesine Taxol, Pacllitaxel and/or Docetaxel); a topoisomerase (e.g., a type I topoisomerase and/or a type 2 topoisomerase; e.g., camptothecins, such as irinotecan and/or topotecan; amsacrine, etoposide, etoposide phosphate and/or teniposide); a cytotoxic antibiotic (e.g., actinomycin, anthracyclines, doxorubicin, daunorubicin, valrubicin, idarubicin, epirubicin, bleomycin, plicamycin and/or mitomycin); a hormone (e.g., a lutenizing hormone releasing hormone agonist; e.g., leuprolidine, goserelin, triptorelin, histrelin, bicalutamide, flutamide and/or nilutamide); an antibody (e.g., Abciximab, Adalimumab, Alemtuzumab, Atlizumab, Basiliximab, Belimumab, Bevacizumab, Bretuximab vedotin, Canakinumab, Cetuximab, Ceertolizumab pegol, Daclizumab, Denosumab, Eculizumab, Efalizumab, Gemtuzumab, Golimumab, Golimumab, Ibritumomab tiuxetan, Infliximab, Ipilimumab, Muromonab-CD3, Natalizumab, Ofatumumab, Omalizumab, Palivizumab, Panitumuab, Ranibizumab, Rituximab, Tocilizumab, Tositumomab and/or Trastuzumab); an anti-angiogenic agent; a cytokine; a thrombotic agent; a growth inhibitory agent; an anti-helminthic agent; and an immune checkpoint inhibitor that targets an immune checkpoint receptor selected from the group consisting of CTLA-4, PD-1, PD-L1, PD-1-PD-L1, PD-1-PD-L2, interleukin-2 (IL-2), indoleamine 2,3-dioxygenase (IDO), IL-10, transforming growth factor-β (TGFβ), T cell immunoglobulin and mucin 3 (TIM3 or HAVCR2), Galectin 9-TIM3, Phosphatidylserine-TIM3, lymphocyte activation gene 3 protein (LAG3), MHC class II-LAG3, 4-1BB-4-1BB ligand, OX40-OX40 ligand, GITR, GITR ligand-GITR, CD27, CD70-CD27, TNFRSF25, TNFRSF25-TL1A, CD40L, CD40-CD40 ligand, HVEM-LIGHT-LTA, HVEM, HVEM-BTLA, HVEM-CD160, HVEM-LIGHT, HVEM-BTLA-CD160, CD80, CD80-PDL-1, PDL2-CD80, CD244, CD48-CD244, CD244, ICOS, ICOS-ICOS ligand, B7-H3, B7-H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86-CD28, CD86-CTLA, CD80-CD28, CD39, CD73 Adenosine-CD39-CD73, CXCR4-CXCL12, Phosphatidylserine, TIM3, Phosphatidylserine-TIM3, SIRPA-CD47, VEGF, Neuropilin, CD160, CD30, and CD155 (e.g., CTLA-4 or PD1 or PD-L1).

147. The method of any one of clauses 140-146, wherein the compound is administered intratumorally.

148. A method of inducing an immune response in a subject in need thereof, the method comprising administering to the subject an effective amount of a compound as defined in any one of clauses 1-121, or a pharmaceutical composition as defined in clause 122.

149. The method of clause 148, wherein the subject has cancer.

150. The method of clause 149, wherein the subject has undergone and/or is undergoing and/or will undergo one or more cancer therapies.

151. The method of clause 149, wherein the cancer selected from the group consisting of melanoma, cervical cancer, breast cancer, ovarian cancer, prostate cancer, testicular cancer, urothelial carcinoma, bladder cancer, non-small cell lung cancer, small cell lung cancer, sarcoma, colorectal adenocarcinoma, gastrointestinal stromal tumors, gastroesophageal carcinoma, colorectal cancer, pancreatic cancer, kidney cancer, hepatocellular cancer, malignant mesothelioma, leukemia, lymphoma, myelodysplasia syndrome, multiple myeloma, transitional cell carcinoma, neuroblastoma, plasma cell neoplasms, Wilm's tumor, or hepatocellular carcinoma.

152. The method of clause any one of clauses 149-151, wherein the cancer is a refractory cancer.

153. The method of clause 148, wherein the immune response is an innate immune response.

154. The method of clause 153, wherein the at least one or more cancer therapies comprises surgery, radiotherapy, chemotherapy, toxin therapy, immunotherapy, cryotherapy or gene therapy, or a combination thereof.

155. The method of clause 154, wherein chemotherapy comprises administering one or more additional chemotherapeutic agents.

156. The method of clause 155, wherein the one or more additional chemotherapeutic agents is selected from alkylating agent (e.g., cisplatin, carboplatin, mechlorethamine, cyclophosphamide, chlorambucil, ifosfamide and/or oxaliplatin); an anti-metabolite (e.g., azathioprine and/or mercaptopurine); a terpenoid (e.g., a *vinca* alkaloid and/or a taxane; e.g., Vincristine, Vinblastine, Vinorelbine and/or Vindesine Taxol, Pacllitaxel and/or Docetaxel); a topoisomerase (e.g., a type I topoisomerase and/or a type 2 topoisomerase; e.g., camptothecins, such as irinotecan and/or topotecan; amsacrine, etoposide, etoposide phosphate and/or teniposide); a cytotoxic antibiotic (e.g., actinomycin, anthracyclines, doxorubicin, daunorubicin, valrubicin, idarubicin, epirubicin, bleomycin, plicamycin and/or mitomycin); a hormone (e.g., a lutenizing hormone releasing hormone agonist; e.g., leuprolidine, goserelin, triptorelin, histrelin, bicalutamide, flutamide and/or nilutamide); an antibody (e.g., Abciximab, Adalimumab, Alemtuzumab, Atlizumab, Basiliximab, Belimumab, Bevacizumab, Bretuximab vedotin, Canakinumab, Cetuximab, Ceertolizumab pegol, Daclizumab, Denosumab, Eculizumab, Efalizumab, Gemtuzumab, Golimumab, Golimumab, Ibritumomab tiuxetan, Infliximab, Ipilimumab, Muromonab-CD3, Natalizumab, Ofatumumab, Omalizumab, Palivizumab, Panitumuab, Ranibizumab, Rituximab, Tocilizumab, Tositumomab and/or Trastuzumab); an anti-angiogenic agent; a cytokine; a thrombotic agent; a growth inhibitory agent; an anti-helminthic agent; and an immune checkpoint inhibitor that targets an immune checkpoint receptor selected from the group consisting of CTLA-4, PD-1, PD-L1, PD-1-PD-L1, PD-1-PD-L2, interleukin-2 (IL-2), indoleamine 2,3-dioxygenase (IDO), IL-10, transforming growth factor-β (TGFβ), T cell immunoglobulin and mucin 3 (TIM3 or HAVCR2), Galectin 9-TIM3, Phosphatidylserine-TIM3, lymphocyte activation gene 3 protein (LAG3), MHC class II-LAG3, 4-1BB-4-1BB ligand, OX40-OX40 ligand, GITR, GITR ligand-GITR, CD27, CD70-CD27, TNFRSF25, TNFRSF25-TL1A, CD40L, CD40-CD40 ligand, HVEM-LIGHT-LTA, HVEM, HVEM-BTLA, HVEM-CD160, HVEM-LIGHT, HVEM-BTLA-CD160, CD80, CD80-PDL-1, PDL2-CD80, CD244, CD48-CD244, CD244, ICOS, ICOS-ICOS ligand, B7-H3, B7-H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86-CD28, CD86-CTLA, CD80-CD28, CD39, CD73 Adenosine-CD39-CD73, CXCR4-CXCL12, Phosphatidylserine, TIM3, Phosphatidylserine-TIM3, SIRPA-CD47, VEGF, Neuropilin, CD160, CD30, and CD155 (e.g., CTLA-4 or PD1 or PD-L1).

157. A method of treatment of a disease in which increased (e.g., excessive) STING signaling contributes to the pathology and/or symptoms and/or progression of the disease, comprising administering to a subject in need of such treatment an effective amount of a compound as defined in any one of clauses 1-121, or a pharmaceutical composition as defined in clause 122.

158. A method of treatment comprising administering to a subject having a disease in which increased (e.g., excessive) STING signaling contributes to the pathology and/or symptoms and/or progression of the disease an effective amount of a compound as defined in any one of clauses 1-121, or a pharmaceutical composition as defined in clause 122.

159. A method of treatment comprising administering to a subject a compound as defined in any one of clauses 1-121, or a pharmaceutical composition as defined in clause 122, wherein the compound or composition is administered in an amount effective to treat a disease in which increased (e.g., excessive) STING signaling contributes to the pathology and/or symptoms and/or progression of the disease, thereby treating the disease.

160. The method of any one of clauses 157-159, wherein the disease is cancer.

161. The method of clause 160, wherein the cancer is selected from the group consisting of melanoma, cervical cancer, breast cancer, ovarian cancer, prostate cancer, testicular cancer, urothelial carcinoma, bladder cancer, non-small cell lung cancer, small cell lung cancer, sarcoma, colorectal adenocarcinoma, gastrointestinal stromal tumors, gastroesophageal carcinoma, colorectal cancer, pancreatic cancer, kidney cancer, hepatocellular cancer, malignant mesothelioma, leukemia, lymphoma, myelodysplasia syndrome, multiple myeloma, transitional cell carcinoma, neuroblastoma, plasma cell neoplasms, Wilm's tumor, or hepatocellular carcinoma.

162. The method of clause 160 or 161, wherein the cancer is a refractory cancer.

163. The method of any one of clauses 160-162, wherein the compound is administered in combination with one or more additional cancer therapies.

164. The method of clause 163, wherein the one or more additional cancer therapies comprises surgery, radiotherapy, chemotherapy, toxin therapy, immunotherapy, cryotherapy or gene therapy, or a combination thereof.

165. The method of clause 164, wherein chemotherapy comprises administering one or more additional chemotherapeutic agents.

166. The method of clause 165, wherein the one or more additional chemotherapeutic agents is selected from an alkylating agent (e.g., cisplatin, carboplatin, mechlorethamine, cyclophosphamide, chlorambucil, ifosfamide and/or oxaliplatin); an anti-metabolite (e.g., azathioprine and/or mercaptopurine); a terpenoid (e.g., a *vinca* alkaloid and/or a taxane; e.g., Vincristine, Vinblastine, Vinorelbine and/or Vindesine Taxol, Paclitaxel and/or Docetaxel); a topoisomerase (e.g., a type 1 topoisomerase and/or a type 2 topoisomerase; e.g., camptothecins, such as irinotecan and/or topotecan; amsacrine, etoposide, etoposide phosphate and/or teniposide); a cytotoxic antibiotic (e.g., actinomycin, anthracyclines, doxorubicin, daunorubicin, valrubicin, idarubicin, epirubicin, bleomycin, plicamycin and/or mitomycin); a hormone (e.g., a lutenizing hormone releasing hormone agonist; e.g., leuprolidine, goserelin, triptorelin, histrelin, bicalutamide, flutamide and/or nilutamide); an antibody (e.g., Abciximab, Adalimumab, Alemtuzumab, Atlizumab, Basiliximab, Belimumab, Bevacizumab, Bretuximab vedotin, Canakinumab, Cetuximab, Ceertolizumab pegol, Daclizumab, Denosumab, Eculizumab, Efalizumab, Gemtuzumab, Golimumab, Golimumab, Ibritumomab tiuxetan, Infliximab, Ipilimumab, Muromonab-CD3, Natalizumab, Ofatumumab, Omalizumab, Palivizumab, Panitumuab, Ranibizumab, Rituximab, Tocilizumab, Tositumomab and/or Trastuzumab); an anti-angiogenic agent; a cytokine; a thrombotic agent; a growth inhibitory agent; an anti-helminthic agent; and an immune checkpoint inhibitor that targets an immune checkpoint receptor selected from the group consisting of CTLA-4, PD-1, PD-L1, PD-1-PD-L1, PD-1-PD-L2, interleukin-2 (IL-2), indoleamine 2,3-dioxygenase (IDO), IL-10, transforming growth factor-β (TGFβ), T cell immunoglobulin and mucin 3 (TIM3 or HAVCR2), Galectin 9-TIM3, Phosphatidylserine-TIM3, lymphocyte activation gene 3 protein (LAG3), MHC class II-LAG3, 4-1BB-4-1BB ligand, OX40-OX40 ligand, GITR, GITR ligand-GITR, CD27, CD70-CD27, TNFRSF25, TNFRSF25-TL1A, CD40L, CD40-CD40 ligand, HVEM-LIGHT-LTA, HVEM, HVEM-BTLA, HVEM-CD160, HVEM-LIGHT, HVEM-BTLA-CD160, CD80, CD80-PDL-1, PDL2-CD80, CD244, CD48-CD244, CD244, ICOS, ICOS-ICOS ligand, B7-H3, B7-H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86-CD28, CD86-CTLA, CD80-CD28, CD39, CD73 Adenosine-CD39-CD73, CXCR4-CXCL12, Phosphatidylserine, TIM3, Phosphatidylserine-TIM3, SIRPA-CD47, VEGF, Neuropilin, CD160, CD30, and CD155 (e.g., CTLA-4 or PD1 or PD-L1).

167. The method of any one of clauses 157-166, wherein the compound is administered intratumorally.

168. A method of treatment of a disease, disorder, or condition associated with STING, comprising administering to a subject in need of such treatment an effective amount of a compound as defined in any one of clauses 1-121, or a pharmaceutical composition as defined in clause 122.

169. The method of clause 168, wherein the disease, disorder, or condition is selected from type I interferonopathies, Aicardi-Goutières Syndrome (AGS), genetic forms of lupus, inflammation-associated disorders, and rheumatoid arthritis.

170. The method of clause 169, wherein the disease, disorder, or condition is a type I interferonopathy (e.g., STING-associated vasculopathy with onset in infancy (SAVI)).

171. The method of clause 170, wherein the type I interferonopathy is STING-associated vasculopathy with onset in infancy (SAVI)).

172. The method of clause 169, wherein the disease, disorder, or condition is Aicardi-Goutières Syndrome (AGS).

173. The method of clause 169, wherein the disease, disorder, or condition is a genetic form of lupus.

174. The method of clause 169, wherein the disease, disorder, or condition is inflammation-associated disorder.

175. The method of clause 174, wherein the inflammation-associated disorder is systemic lupus erythematosus.

176. The method of any one of clauses 123-175, wherein the method further comprises identifying the subject.

177. A combination comprising a compounds defined in any one of clauses 1-121 or a pharmaceutically acceptable salt or tautomer thereof, and one or more therapeutically active agents.

178. A compound defined in any one of clauses 1-121 or a pharmaceutically acceptable salt or tautomer thereof, or a pharmaceutical composition defined in clause 122, for use as a medicament.

179. A compound defined in any one of clauses 1-121 or a pharmaceutically acceptable salt or tautomer thereof, or a pharmaceutical composition defined in clause 122, for use in the treatment of a disease, condition or disorder modulated by STING inhibition.

180. A compound defined in any one of clauses 1-121 or a pharmaceutically acceptable salt or tautomer thereof, or the pharmaceutical composition defined in clause 122, for use in the treatment of a disease mentioned in any one of clauses 123 to 176 (e.g., any one of clauses 128, 130, 132-134, 141-142, 149, 151, 152, 157-162, or 168-175).

181. Use of a compound defined in any one of clauses 1-121 or a pharmaceutically acceptable salt or tautomer thereof, or a pharmaceutical composition defined in clause 122, in the manufacture of a medicament for the treatment of a disease mentioned in in any one of clauses 109 to 162 (e.g., any one of clauses 128, 130, 132-134, 141-142, 149, 151, 152, 157-162, or 168-175).

What is claimed is:
1. A compound of Formula (I):

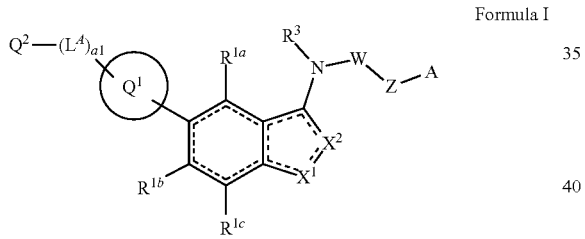

Formula I or a pharmaceutically acceptable salt thereof or a tautomer thereof, wherein:
$X^1$ is $NR^2$;
$X^2$ is $CR^5$;
each ═══ is independently a single bond or a double bond, provided that the five-membered ring comprising $X^1$ and $X^2$ is heteroaryl, and
the 6-membered ring

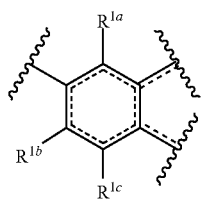

is aromatic;
$R^{1a}$, $R^{1b}$, $R^{1c}$, and $R^5$ are each independently selected from the group consisting of: H; $R^c$; $R^h$; and $-(L^1)_{b1}-R^h$;
each occurrence of $R^2$ is independently selected from the group consisting of: H; $R^d$; $R^g$; and $-(L^2)_{b2}-R^g$;

$Q^1$ is selected from the group consisting of:
heteroarylene of 5-6 ring atoms, wherein 1-3 ring atoms are heteroatoms, each independently selected from the group consisting of N, N(H), N($R^d$), O, and S(O)$_{0-2}$, and wherein the heteroarylene is optionally substituted with 1-4 substituents independently selected from the group consisting of $R^c$ and $R^h$; and
$C_6$ arylene optionally substituted with 1-4 substituents independently selected from the group consisting of $R^c$ and $R^h$;
each $L^A$ is independently selected from the group consisting of: $C_{1-3}$ alkylene optionally substituted with 1-2 $R^a$; —O—; —NH—; —NR$^d$; —S(O)$_{0-2}$; and C(O);
a1 is 0, 1, 2, 3, or 4;
provided that $-(L^A)_{a1}-$ cannot contain bond(s) between O, N, or S(O)$_0$ atoms, unless an N—N bond is further attached to C(O);
$Q^2$ is $R^g$;
$R^3$ is selected from the group consisting of: H; $R^d$; and $R^h$;
W is:
(i) C(═O);
Z and A are defined according to (AA) or (BB) below:
(AA)
Z is —N(H)— or —N($R^d$)—;
A is selected from the group consisting of:
H;
$C_{1-10}$ alkyl which is optionally substituted with 1-6 $R^b$; and
$-(Y^{A1})_{nA}-Y^{A2}$, wherein:
nA is 0 or 1;
$Y^{A1}$ is $C_{1-6}$ alkylene optionally substituted with 1-3 $R^b$, and
$Y^{A2}$ is selected from the group consisting of:
monocyclic $C_{3-8}$ cycloalkyl or $C_{3-8}$ cycloalkenyl, each of which is optionally substituted with 1-4 substituents independently selected from the group consisting of oxo and $R^c$; and
monocyclic heterocyclyl or heterocycloalkenyl of 3-8 ring atoms, wherein 1-3 ring atoms are heteroatoms, each independently selected from the group consisting of N, N(H), N($R^d$), O, and S(O)$_{0-2}$, and wherein the heterocyclyl or heterocycloalkenyl is optionally substituted with 1-4 substituents independently selected from the group consisting of oxo and $R^c$; or
Z and A, taken together, form:

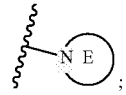

(BB)

and
Ring E is a saturated or partially unsaturated ring of 3-16 ring atoms, wherein 0-3 ring atoms are heteroatoms (in addition to the nitrogen atom already present), each independently selected from the group consisting of N, N(H), N($R^d$), O, and S(O)$_{0-2}$, and wherein the ring is optionally substituted with 1-4 substituents independently selected from the group consisting of: oxo, $R^c$, $R^h$, and $-(L^g)_{bg}-R^h$;
each occurrence of $R^a$ and $R^b$ is independently selected from the group consisting of: —OH; -halo; —NR$^e$R$^f$; $C_{1-4}$ alkoxy; $C_{1-4}$ haloalkoxy; —C(═O)O($C_{1-4}$ alkyl); —C(═O)($C_{1-4}$ alkyl); —C(═O)OH; —CONR'R"; —S(O)$_{1-2}$NR'R"; —S(O)$_{1-2}$($C_{1-4}$ alkyl); and cyano;

each occurrence of $R^c$ is independently selected from the group consisting of: halo; cyano; $C_{1-10}$ alkyl which is optionally substituted with 1-6 independently selected $R^a$; $C_{2-6}$ alkenyl; $C_{2-6}$ alkynyl; $C_{1-4}$ alkoxy; $C_{1-4}$ haloalkoxy; —S(O)$_{1-2}$(C$_{1-4}$ alkyl); —S(O)(=NH)(C$_{1-4}$ alkyl); —NR$^e$R$^f$; —OH; —S(O)$_{1-2}$NR'R"; —C$_{1-4}$ thioalkoxy; —NO$_2$; —C(=O)(C$_{1-10}$ alkyl); —C(=O)O(C$_{1-4}$ alkyl); —C(=O)OH; —C(=O)NR'R"; and —SF$_5$;

each occurrence of $R^d$ is independently selected from the group consisting of: $C_{1-6}$ alkyl optionally substituted with 1-3 independently selected $R^a$; —C(O)(C$_{1-4}$ alkyl); —C(O)O(C$_{1-4}$ alkyl); —CONR'R"; —S(O)$_{1-2}$NR'R"; —S(O)$_{1-2}$(C$_{1-4}$ alkyl); —OH; and $C_{1-4}$ alkoxy;

each occurrence of $R^e$ and $R^f$ is independently selected from the group consisting of: H; $C_{1-6}$ alkyl optionally substituted with 1-3 substituents each independently selected from the group consisting of NR'R", —OH, and $R^i$; —C(O)(C$_{1-4}$ alkyl); —C(O)O(C$_{1-4}$ alkyl); —CONR'R"; —S(O)$_{1-2}$NR'R"; —S(O)$_{1-2}$(C$_{1-4}$ alkyl); —OH; and $C_{1-4}$ alkoxy;

each occurrence of $R^g$ is independently selected from the group consisting of:
  $C_{3-12}$ cycloalkyl or $C_{3-12}$ cycloalkenyl, each of which is optionally substituted with 1-4 substituents independently selected from the group consisting of oxo, $R^c$, $R^h$, and -(L$^g$)$_{bg}$-R$^h$;
  heterocyclyl or heterocycloalkenyl of 3-12 ring atoms, wherein 1-3 ring atoms are heteroatoms, each independently selected from the group consisting of N, N(H), N(R$^d$), O, and S(O)$_{0-2}$, and wherein the heterocyclyl or heterocycloalkenyl is optionally substituted with 1-4 substituents independently selected from the group consisting of oxo, $R^c$, $R^h$, and -(L$^g$)$_{bg}$-R$^h$;
  heteroaryl of 5-12 ring atoms, wherein 1-3 ring atoms are heteroatoms, each independently selected from the group consisting of N, N(H), N(R$^d$), O, and S(O)$_{0-2}$, and wherein the heteroaryl is optionally substituted with 1-4 substituents independently selected from the group consisting of $R^c$, $R^h$, and -(L$^g$)$_{bg}$-R$^h$; and
  $C_{6-10}$ aryl optionally substituted with 1-4 substituents independently selected from the group consisting of $R^c$, $R^h$, and -(L$^g$)$_{bg}$-R$^h$;

each occurrence of $R^h$ is independently selected from the group consisting of:
  $C_{3-8}$ cycloalkyl or $C_{3-8}$ cycloalkenyl, each of which is optionally substituted with 1-4 $R^i$;
  heterocyclyl or heterocycloalkenyl of 3-8 ring atoms, wherein 1-3 ring atoms are heteroatoms, each independently selected from the group consisting of N, N(H), N(R$^d$), O, and S(O)$_{0-2}$, and wherein the heterocyclyl or heterocycloalkenyl is optionally substituted with 1-4 $R^i$;
  heteroaryl of 5-6 ring atoms, wherein 1-3 ring atoms are heteroatoms, each independently selected from the group consisting of N, N(H), N(R$^d$), O, and S, and wherein the heteroaryl is optionally substituted with 1-4 $R^i$; and
  $C_6$ aryl optionally substituted with 1-4 $R^i$, each occurrence of $R^i$ is independently selected from the group consisting of: $C_{1-6}$ alkyl; $C_{1-4}$ haloalkyl; $C_{1-4}$ alkoxy; $C_{1-4}$ haloalkoxy; and halo;

each occurrence of $L^1$, $L^2$, and $L^g$ is selected from the group consisting of: —O—, —NH—, —NR$^d$, —S(O)$_{0-2}$, C(O), and $C_{1-3}$ alkylene optionally substituted with 1-3 $R^a$;

b1, b2, and bg are each independently 1, 2, or 3; and each occurrence of R' and R" is independently selected from the group consisting of: H; —OH; and $C_{1-4}$ alkyl.

2. The compound of claim 1, wherein $Q^1$ is:
(ii) heteroarylene of 5-6 ring atoms, wherein 1-3 ring atoms are heteroatoms, each independently selected from the group consisting of N, N(H), N(R$^d$), O, and S, and wherein the heteroarylene is optionally substituted with 1-3 substituents independently selected from the group consisting of $R^c$ and $R^h$.

3. The compound of claim 1, wherein $Q^1$ is:
(i) heteroarylene of 5 ring atoms, wherein 1-3 ring atoms are heteroatoms, each independently selected from the group consisting of N, N(H), N(R$^d$), O, and S, and wherein the heteroarylene is optionally substituted with 1-2 $R^c$;
(ii) pyrazolylene which is optionally substituted with 1-2 $R^c$;
(iii)

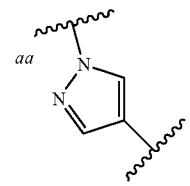 [SMILES: *c1cnn(*)c1]

which is optionally substituted with 1-2 $R^c$, wherein aa represents point of attachment to -(L$^A$)$_{a1}$-Q$^2$; or
(iv)

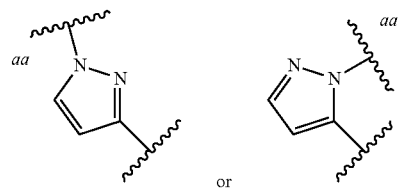

each of which is optionally substituted with 1-2 $R^c$, wherein aa represents point of attachment to -(L$^A$)$_{a1}$-Q$^2$.

4. The compound of claim 1, wherein $Q^1$ is:
(i) $Q^1$ is heteroarylene of 6 ring atoms, wherein 1-3 ring atoms are ring nitrogen atoms, and wherein the heteroarylene is optionally substituted with 1-3 substituents independently selected from the group consisting of $R^c$ and $R^h$;
(ii) $C_6$ arylene optionally substituted with 1-4 substituents independently selected from the group consisting of $R^c$ and $R^h$; or
(iii) phenylene which is optionally substituted with 1-3 substituents independently selected from the group consisting of $R^c$ and $R^h$.

5. The compound of claim 1, wherein a1 is 0.

6. The compound of claim 1, wherein a1 is 1; and optionally $L^A$ is CH$_2$.

7. The compound of claim 1, wherein $Q^2$ is:
(ii) a moiety selected from the group consisting of:
heteroaryl of 5-6 ring atoms, wherein 1-3 ring atoms are heteroatoms, each independently selected from the group consisting of N, N(H), N($R^d$), O, and S, and wherein the heteroaryl is optionally substituted with 1-4 $R^c$; and
$C_6$ aryl optionally substituted with 1-4 $R^c$.

8. The compound of claim 1, wherein $Q^2$ is phenyl or pyridyl, each optionally substituted with 1-2 $R^c$.

9. The compound of claim 1, wherein $Q^2$ is:
(i) $C_{3-12}$ cycloalkyl or $C_{3-12}$ cycloalkenyl, each of which is optionally substituted with 1-4 substituents independently selected from the group consisting of oxo and $R^c$;
(i) $C_{3-6}$ cycloalkyl, which is optionally substituted with 1-4 substituents independently selected from the group consisting of oxo and $R^c$; or
(ii) cyclopropyl or cyclopentyl each of which is optionally substituted with 1-2 $R^c$.

10. The compound of claim 1, wherein $Q^2$ is:
(i) heterocyclyl or heterocycloalkenyl of 3-12 ring atoms, wherein 1-3 ring atoms are heteroatoms, each independently selected from the group consisting of N, N(H), N($R^d$), O, and $S(O)_{0-2}$, and wherein the heterocyclyl or heterocycloalkenyl is optionally substituted with 1-4 substituents independently selected from the group consisting of oxo and $R^c$;
(ii) heterocyclyl of 4-8 ring atoms, wherein 1-3 ring atoms are heteroatoms, each independently selected from the group consisting of N, N(H), N($R^d$), O, and $S(O)_{0-2}$, and wherein the heterocyclyl is optionally substituted with 1-4 substituents independently selected from the group consisting of oxo and $R^c$; or
(iii)

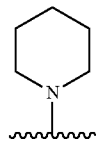

optionally substituted with 1-2 $R^c$.

11. The compound of claim 1, wherein $R^{1a}$ is —H; $R^{1b}$ is —H; and $R^{1c}$ is —H.

12. The compound of claim 1, wherein:
(ii) $X^1$ is NH; and $X^2$ is CH.

13. The compound of claim 1, wherein Z and A are defined according to (AA).

14. The compound of claim 1, wherein A is $C_{1-10}$ alkyl which is optionally substituted with 1-6 $R^b$.

15. The compound of claim 1, wherein A is unsubstituted $C_{1-6}$ alkyl.

16. The compound of claim 1, wherein A is methyl, ethyl, propyl, isopropyl, or isobutyl.

17. The compound of claim 1, wherein A is $C_{1-6}$ alkyl which is substituted with 1-6 substituents each independently selected from the group consisting of: —OH; -halo; —$NR^eR^f$; $C_{1-4}$ alkoxy; $C_{1-4}$ haloalkoxy; —C(=O)O($C_{1-4}$ alkyl); —C(=O)($C_{1-4}$ alkyl); and cyano.

18. The compound of claim 1, wherein A is $C_{1-6}$ alkyl substituted with 1-6 independently selected halo.

19. The compound of claim 1, wherein A is —$CH_2CF_3$, —$CH_2CHF_2$, or —$CH_2CH_2CF_3$.

20. The compound of claim 1, wherein A is $C_{1-6}$ alkyl substituted with —OH, $C_{1-4}$ alkoxy, or $C_{1-4}$ haloalkoxy.

21. The compound of claim 1, wherein A is

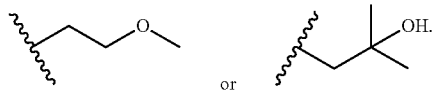

22. The compound of claim 1, wherein A is $-(Y^{A1})_{nA}-Y^{A2}$.

23. The compound of claim 1, wherein $Y^{A2}$ is monocyclic $C_{3-8}$ cycloalkyl or $C_{3-8}$ cycloalkenyl, each of which is optionally substituted with 1-4 substituents independently selected from the group consisting of oxo and $R^c$.

24. The compound of claim 1, wherein $Y^{A2}$ is monocyclic $C_{3-8}$ cycloalkyl which is optionally substituted with 1-2 substituents independently selected from the group consisting of oxo and $R^c$.

25. The compound of claim 1, wherein $Y^{A2}$ is selected from the group consisting of cyclopropyl; cyclobutyl; and cyclopentyl, each of which is optionally substituted with 1-2 $R^c$.

26. The compound of claim 1, wherein $Y^{A2}$ is monocyclic heterocyclyl or heterocycloalkenyl of 3-8 ring atoms, wherein 1-3 ring atoms are heteroatoms, each independently selected from the group consisting of N, N(H), N($R^d$), O, and $S(O)_{0-2}$, and wherein the heterocyclyl or heterocycloalkenyl is optionally substituted with 1-4 substituents independently selected from the group consisting of oxo and $R^c$.

27. The compound of claim 1, wherein $Y^{A2}$ is monocyclic heterocyclyl of 3-8 ring atoms, wherein 1-3 ring atoms are heteroatoms, each independently selected from the group consisting of N, N(H), N($R^d$), O, and $S(O)_{0-2}$, and wherein the heterocyclyl is optionally substituted with 1-2 substituents independently selected from the group consisting of oxo and $R^c$.

28. The compound of claim 1, wherein $Y^{A2}$ is oxetanyl, tetrahydrofuranyl, or pyrrolidinyl, each of which is optionally substituted with 1-2 $R^c$, and the pyrrolidinyl is optionally substituted with $R^d$ at a ring nitrogen atom.

29. The compound of claim 1, wherein Z and A are defined according to (BB).

30. The compound of claim 1, wherein Z and A, taken together, form:

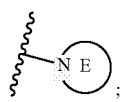

and
Ring E is a saturated or partially unsaturated ring of 3-8 ring atoms, wherein 0-2 ring atoms are heteroatoms (in addition to the ring nitrogen atom already present), each independently selected from the group consisting of N, N(H), N($R^d$), O, and $S(O)_{0-2}$, and wherein the ring is optionally substituted with 1-4 substituents independently selected from the group consisting of: oxo, $R^c$, $R^h$, and $-(L^g)_{bg}-R^h$.

31. The compound of claim 1, wherein the compound is a compound of Formula (Ia):

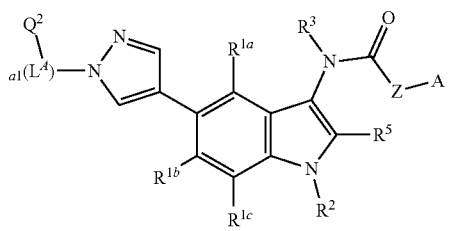

Formula Ia or a pharmaceutically acceptable salt thereof, wherein:
$L^A$ is —CH$_2$—;
a1 is 0 or 1;
$Q^2$ has the following formula:

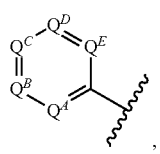

wherein $Q^A$, $Q^B$, $Q^C$, $Q^D$, and $Q^E$ are each independently selected from the group consisting of CH, CR$^{cq2}$, and N, provided that no more than 2 of $Q^A$-$Q^E$ are N, and no more than 2 of $Q^A$-$Q^E$ are CR$^{cq2}$, wherein each R$^{cq2}$ is independently R$^c$, Z and A are as defined according to (AA), wherein A is:
(i) C$_{1-10}$ alkyl which is optionally substituted with 1-6 R$^b$; or
(ii) Y$^{A2}$ or —CH$_2$-Y$^{A2}$, wherein Y$^{A2}$ is selected from the group consisting of:
monocyclic C$_{3-6}$ cycloalkyl, which is optionally substituted with 1-2 substituents independently selected from the group consisting of oxo and R$^c$; and
monocyclic heterocyclyl of 4-6 ring atoms, wherein 1-2 ring atoms are heteroatoms, each independently selected from the group consisting of N, N(H), N(R$^d$), O, and S(O)$_{0-2}$, and wherein the heterocyclyl is optionally substituted with 1-2 substituents independently selected from the group consisting of oxo and R$^c$; and
optionally wherein each R$^{cq2}$ is independently selected from the group consisting of: halo; cyano; C$_{1-6}$ alkyl; C$_{1-6}$ alkyl substituted with 1-6 substituents each independently selected from the group consisting of -halo, C$_{1-3}$ alkoxy, and —OH; C$_{1-4}$ alkoxy; C$_{1-4}$ haloalkoxy; and —C$_{1-4}$ thioalkoxy.

32. The compound of claim 31, wherein R$^{1a}$ is —H; R$^{1b}$ is —H; and R$^{1c}$ is —H.

33. The compound of claim 31, wherein R$^2$ is H; R$^3$ is H; and R$^5$ is H.

34. The compound of claim 1, wherein the compound is selected from the group consisting of or a pharmaceutically acceptable salt thereof:

| Compound No. | Structure |
|---|---|
| 101 | 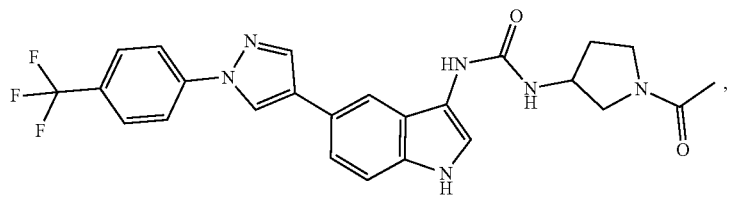 [SMILES: CC(=O)N1CCC(NC(=O)Nc2c[nH]c3ccc(-c4cnn(-c5ccc(C(F)(F)F)cc5)c4)cc23)C1] |
| 102 | 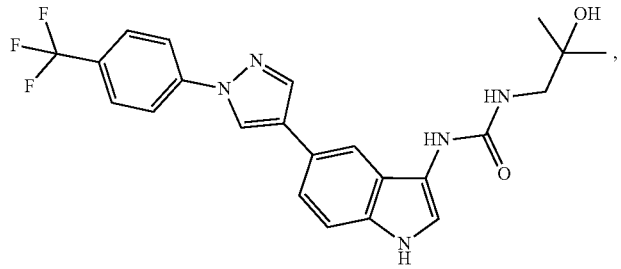 [SMILES: CC(C)(O)CNC(=O)Nc1c[nH]c2ccc(-c3cnn(-c4ccc(C(F)(F)F)cc4)c3)cc12] |
| 103 | 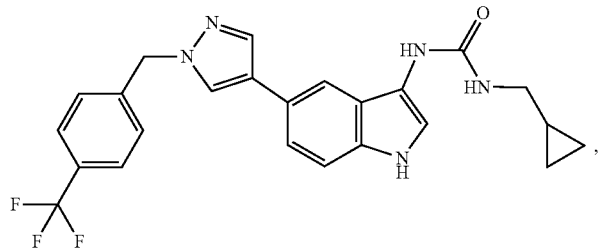 [SMILES: O=C(NCC1CC1)Nc1c[nH]c2ccc(-c3cnn(Cc4ccc(C(F)(F)F)cc4)c3)cc12] |

-continued
| Compound No. | Structure |
|---|---|
| 104 | 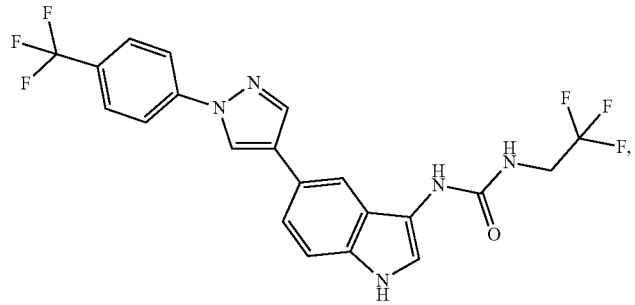 [SMILES: O=C(NCC(F)(F)F)Nc1c[nH]c2ccc(-c3cnn(-c4ccc(C(F)(F)F)cc4)c3)cc12] |
| 105 | 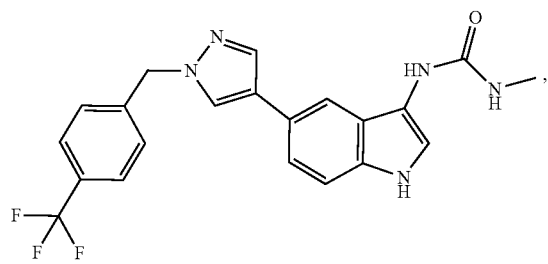 [SMILES: CNC(=O)Nc1c[nH]c2ccc(-c3cnn(Cc4ccc(C(F)(F)F)cc4)c3)cc12] |
| 106 | 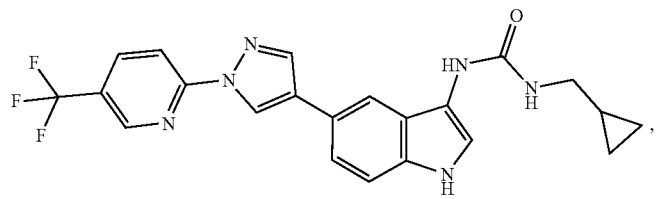 [SMILES: O=C(NCC1CC1)Nc1c[nH]c2ccc(-c3cnn(-c4ccc(C(F)(F)F)cn4)c3)cc12] |
| 107 | 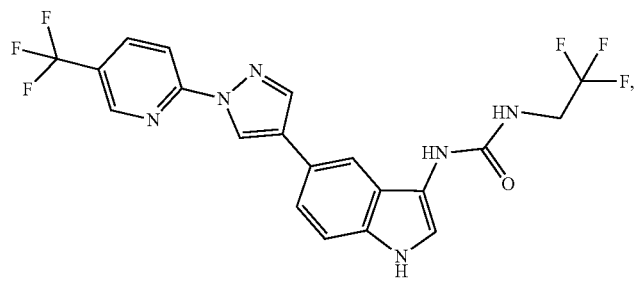 [SMILES: O=C(NCC(F)(F)F)Nc1c[nH]c2ccc(-c3cnn(-c4ccc(C(F)(F)F)cn4)c3)cc12] |
| 108 | 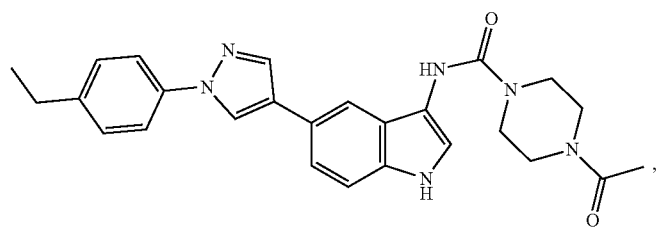 [SMILES: CCc1ccc(-n2cc(-c3ccc4[nH]cc(NC(=O)N5CCN(C(C)=O)CC5)c4c3)cn2)cc1] |
| 109 | 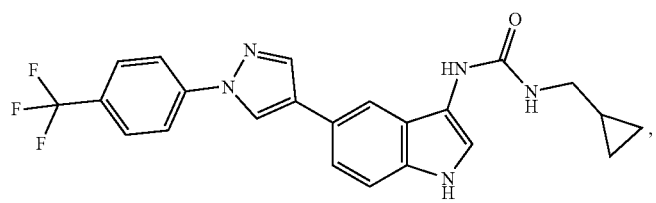 [SMILES: O=C(NCC1CC1)Nc1c[nH]c2ccc(-c3cnn(-c4ccc(C(F)(F)F)cc4)c3)cc12] |

| Compound No. | Structure |
|---|---|
| 110 | 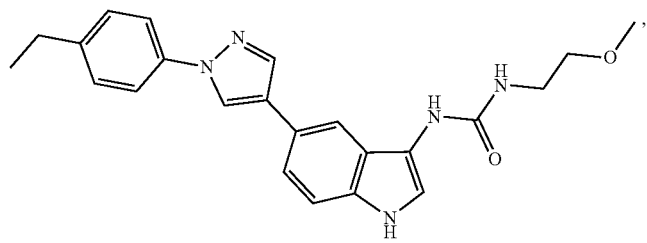 [SMILES: CCc1ccc(-n2cc(-c3ccc4[nH]cc(NC(=O)NCCOC)c4c3)cn2)cc1] |
| 111 | 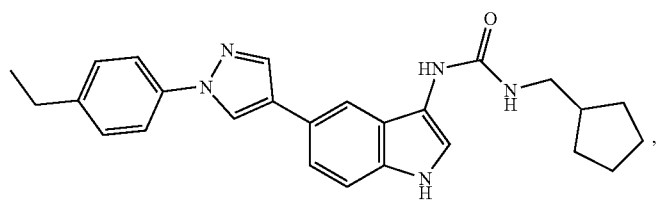 [SMILES: CCc1ccc(-n2cc(-c3ccc4[nH]cc(NC(=O)NCC5CCCC5)c4c3)cn2)cc1] |
| 112 | 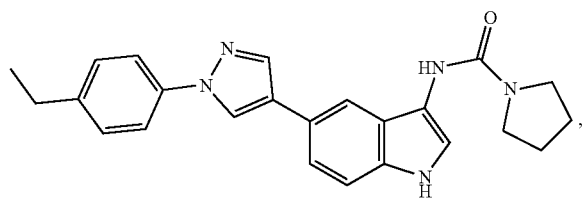 [SMILES: CCc1ccc(-n2cc(-c3ccc4[nH]cc(NC(=O)N5CCCC5)c4c3)cn2)cc1] |
| 113 | 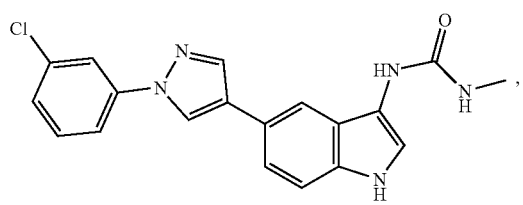 [SMILES: CNC(=O)Nc1c[nH]c2ccc(-c3cnn(-c4cccc(Cl)c4)c3)cc12] |
| 114 | 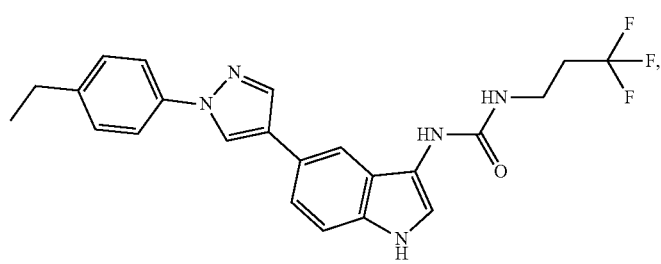 [SMILES: CCc1ccc(-n2cc(-c3ccc4[nH]cc(NC(=O)NCCC(F)(F)F)c4c3)cn2)cc1] |
| 115 | 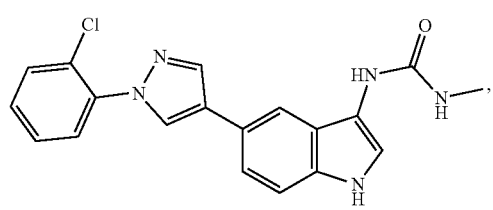 [SMILES: CNC(=O)Nc1c[nH]c2ccc(-c3cnn(-c4ccccc4Cl)c3)cc12] |
| 116 | 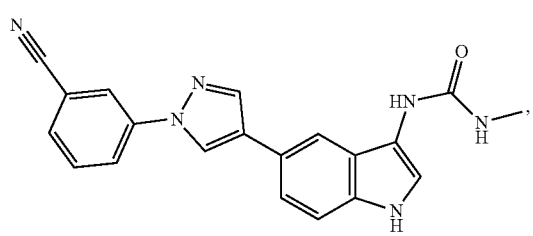 [SMILES: CNC(=O)Nc1c[nH]c2ccc(-c3cnn(-c4cccc(C#N)c4)c3)cc12] |

| Compound No. | Structure |
|---|---|
| 118 | 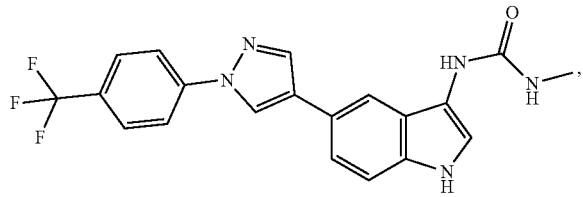 [SMILES: CNC(=O)Nc1c[nH]c2ccc(-c3cnn(-c4ccc(C(F)(F)F)cc4)c3)cc12] |
| 119 | 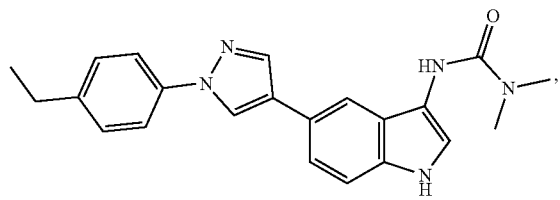 [SMILES: CCc1ccc(-n2cc(-c3ccc4[nH]cc(NC(=O)N(C)C)c4c3)cn2)cc1] |
| 120 | 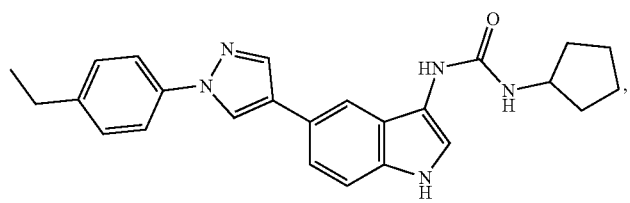 [SMILES: CCc1ccc(-n2cc(-c3ccc4[nH]cc(NC(=O)NC5CCCC5)c4c3)cn2)cc1] |
| 123 | 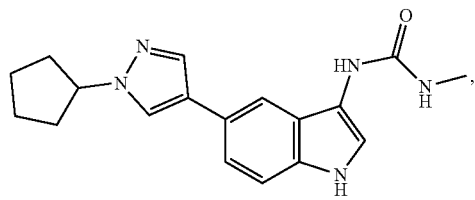 [SMILES: CNC(=O)Nc1c[nH]c2ccc(-c3cnn(C4CCCC4)c3)cc12] |
| 124 | 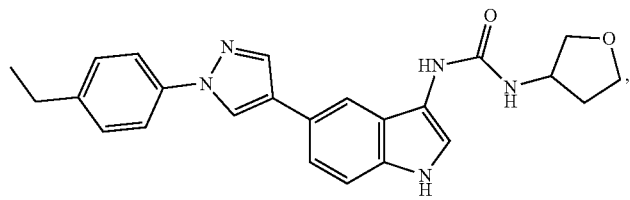 [SMILES: CCc1ccc(-n2cc(-c3ccc4[nH]cc(NC(=O)NC5CCOC5)c4c3)cn2)cc1] |
| 125 | 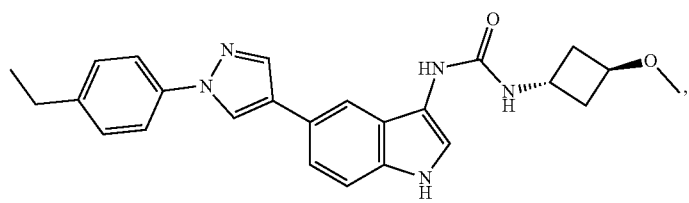 [SMILES: CCc1ccc(-n2cc(-c3ccc4[nH]cc(NC(=O)N[C@H]5C[C@H](OC)C5)c4c3)cn2)cc1] |

| Compound No. | Structure |
|---|---|
| 126 | 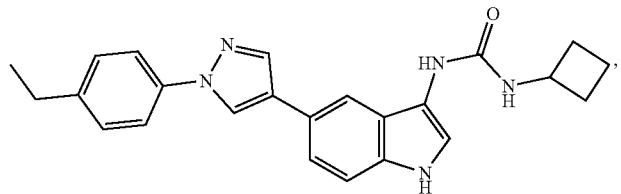 [SMILES: CCc1ccc(-n2cc(-c3ccc4[nH]cc(NC(=O)NC5CCC5)c4c3)cn2)cc1] |
| 127 | 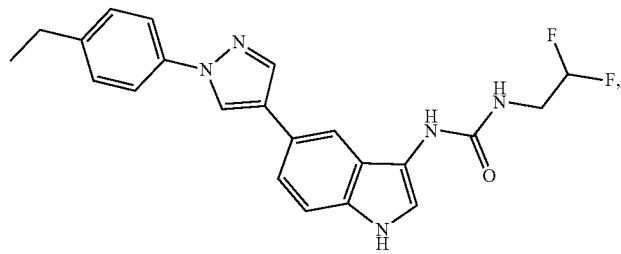 [SMILES: CCc1ccc(-n2cc(-c3ccc4[nH]cc(NC(=O)NCC(F)F)c4c3)cn2)cc1] |
| 128 | 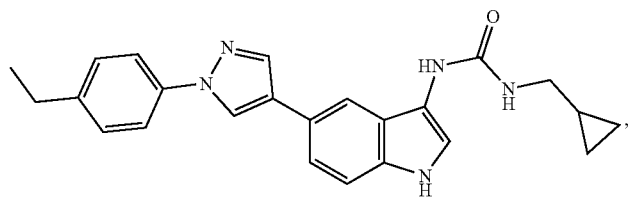 [SMILES: CCc1ccc(-n2cc(-c3ccc4[nH]cc(NC(=O)NCC5CC5)c4c3)cn2)cc1] |
| 129 | 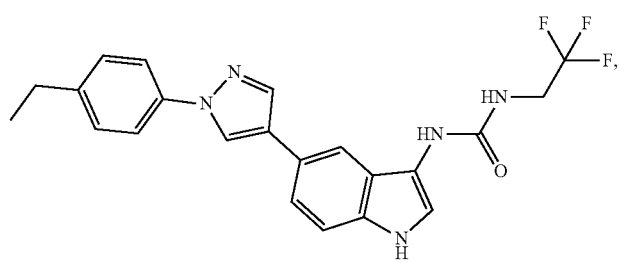 [SMILES: CCc1ccc(-n2cc(-c3ccc4[nH]cc(NC(=O)NCC(F)(F)F)c4c3)cn2)cc1] |
| 130 | 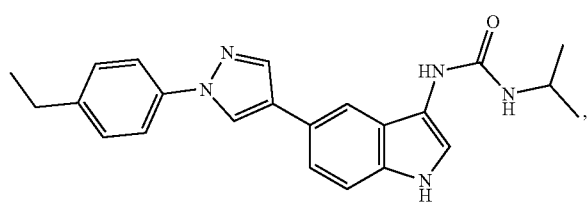 [SMILES: CCc1ccc(-n2cc(-c3ccc4[nH]cc(NC(=O)NC(C)C)c4c3)cn2)cc1] |
| 131 | 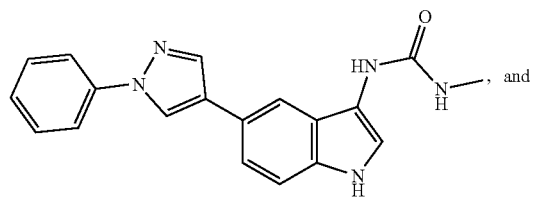 [SMILES: CNC(=O)Nc1c[nH]c2ccc(-c3cnn(-c4ccccc4)c3)cc12] and |
| 132 | 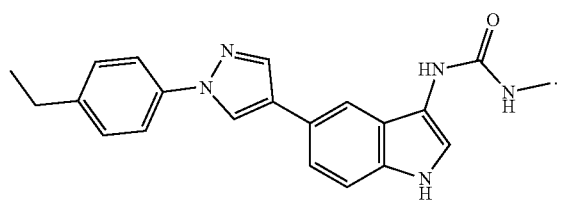 [SMILES: CCc1ccc(-n2cc(-c3ccc4[nH]cc(NC(=O)NC)c4c3)cn2)cc1] |

35. A pharmaceutical composition comprising a compound of claim 1, or a pharmaceutically acceptable salt thereof, and one or more pharmaceutically acceptable excipients.

36. A method for inhibiting STING activity, the method comprising contacting STING with a compound as claimed in claim 1, or a pharmaceutically acceptable salt thereof; or a pharmaceutical composition as claimed in claim 35.

* * * * *